(12) United States Patent
Littman et al.

(10) Patent No.: US 6,391,567 B1
(45) Date of Patent: May 21, 2002

(54) IDENTIFYING COMPOUNDS INHIBITING DC-SIGN FACILITATION OF HIV INTO CELLS

(75) Inventors: Dan R. Littman, New York; Douglas Kwon, Long Island City, both of NY (US); Yvette Van Kooyk; Teunis Geijtenbeek, both of Nijmegen (NL)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/517,605

(22) Filed: Mar. 2, 2000

(51) Int. Cl.[7] .......................... G01N 33/53; C12Q 1/02; C12N 15/00; C12N 5/00; C12N 5/02
(52) U.S. Cl. ..................... 435/7.2; 435/320.1; 435/325; 435/29
(58) Field of Search ............................. 435/325, 4, 3, 435/8, 9, 11, 13, 18, 320.1, 29, 7.2; 800/3, 8, 9, 11, 13, 18

(56) References Cited

PUBLICATIONS

Nath et. al.; The chaimpanzee and other non–human–primate models in HIV–1 vaccine research, 2000, Trends in Microbiology vol. 8, No. 9: 426–431.*
Romano et. al.; Gene Transfer Technology in Therapy: Current Applications and Future Goals, 1999, Stem Cells 17: 191–202.*
Ayehunie et al., 1997, *Blood*, 90(4):1379–1386.
Barratt–Boyes et al., 1997, *J. Immunol.*, 158:4543–7.
Blauvelt et al., 1997, *J. Clin. Invest.*, 100:2043–2053.
Cameron et al., 1992, *Science*, 257:383–387.
Cameron et al., 1994, *J. Leukoc. Biol.*, 56(3):257–265.
Cameron et al., 1996, *J. Leukoc. Biol.*, 59(2):158–171.
Canque et al., 1999, *Blood*, 93(11):3866–3875.
Chan et al., 1997, *Cell*, 89:263–273.
Curtis et al., 1992, *Proc. Natl. Acad. Sci. U.S.A.*, 89:8536–8360.
Geijtenbeek et al., 1999, *Blood*, 94(2):754–64.
Geijtenbeek et al., 2000, *Cell*, 100:587–97.
Granelli–Piperno et al., 1996, *J. Exp. Med.*, 184:2433–2438.
Granelli–Piperno et al., 1999, *Curr. Biol.*, 9:21–29.
Grouard and Clark, 1997, *Curr. Opin. Immunol.*, 9:563–567.
Harouse et al., 1991, *Science*, 253:320–323.
Hladik et al., *J. Virol.*, 73(7):5833–42.
Kwong et al., 1998, *Nature*, 393:648–659.
Lee et al., 1997, *J. Virol.*, 71(8):6037–6043.
Littman, 1998, *Cell*, 93:677–80.
Rowland–Jones, S.L. et al., 1999, *Curr. Biol.*, 9:547–50.
Rubbert et al., 1998, *J. Immunol.*, 160:3933–3941.
Speck et al. 1999, *Curr. Biol.*, 9:547–50.
Stahl–Hennig et al., 1999, *Science*, 285:1261–1265.
Steinman and Inaba, 1999, *J. Leukoc. Biol.*, 66:205–208.
Weis et al., 1998, *Immunol. Rev.*, 163:19–34.
Weissman et al., 1995, *Proc. Natl. Acad. Sci U.S.A.*, 92:826–830.

* cited by examiner

*Primary Examiner*—Deborah Crouch
*Assistant Examiner*—Thaian N. Ton
(74) *Attorney, Agent, or Firm*—Klauber & Jackson; Valeta Gregg

(57) ABSTRACT

The present invention demonstrates that a receptor, named DC-SIGN, is specifically expressed on dendritic cells, and facilitates infection of T lymphocytes with HIV. Assays for identifying compounds that modulate the interaction of DC-SIGN and HIV and/or T cells and macrophage are provided. Compounds so identified are also part of the present invention.

13 Claims, 15 Drawing Sheets

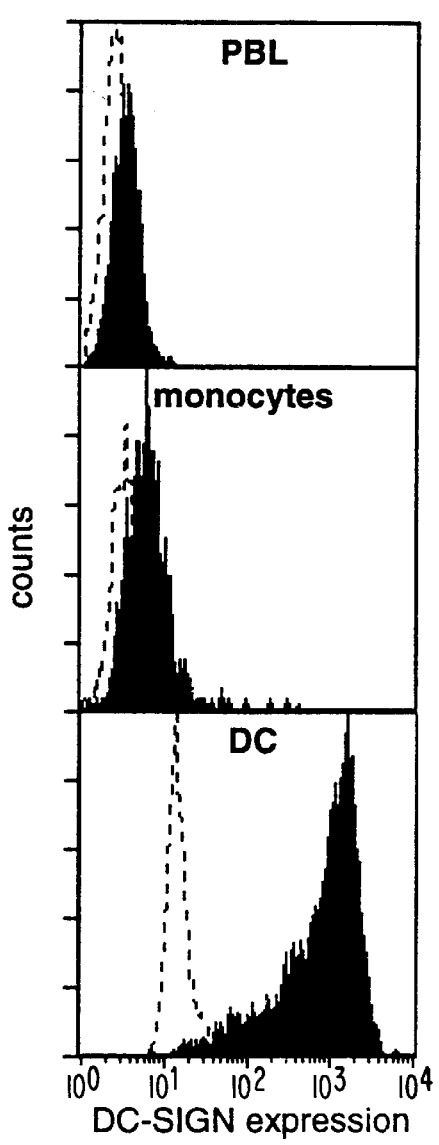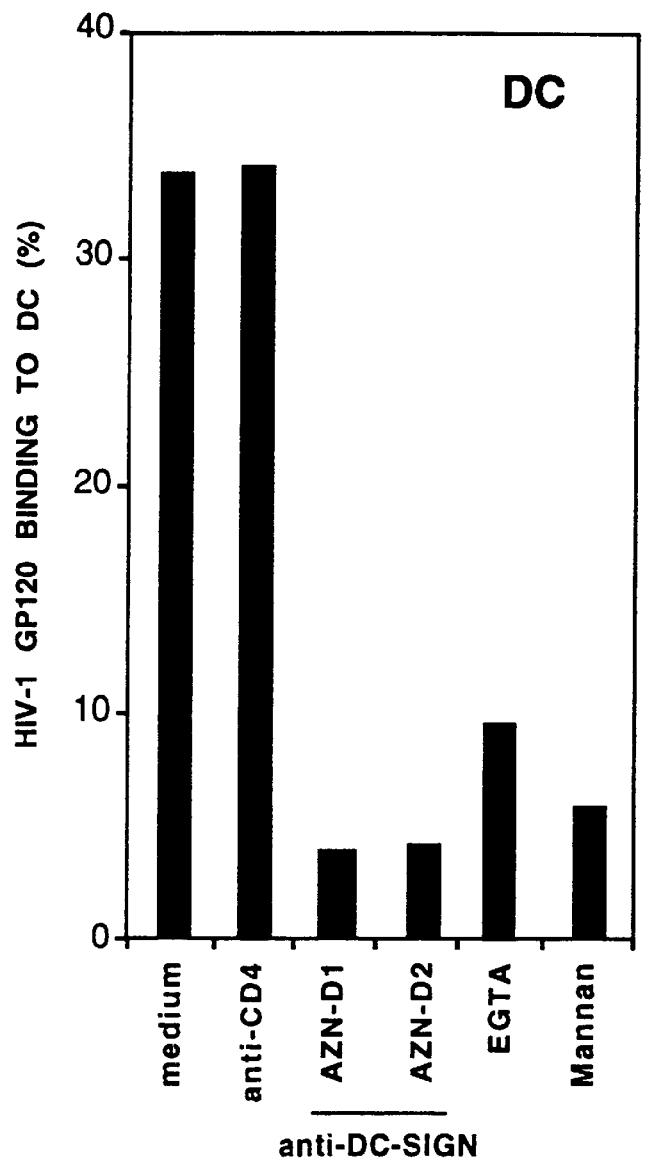

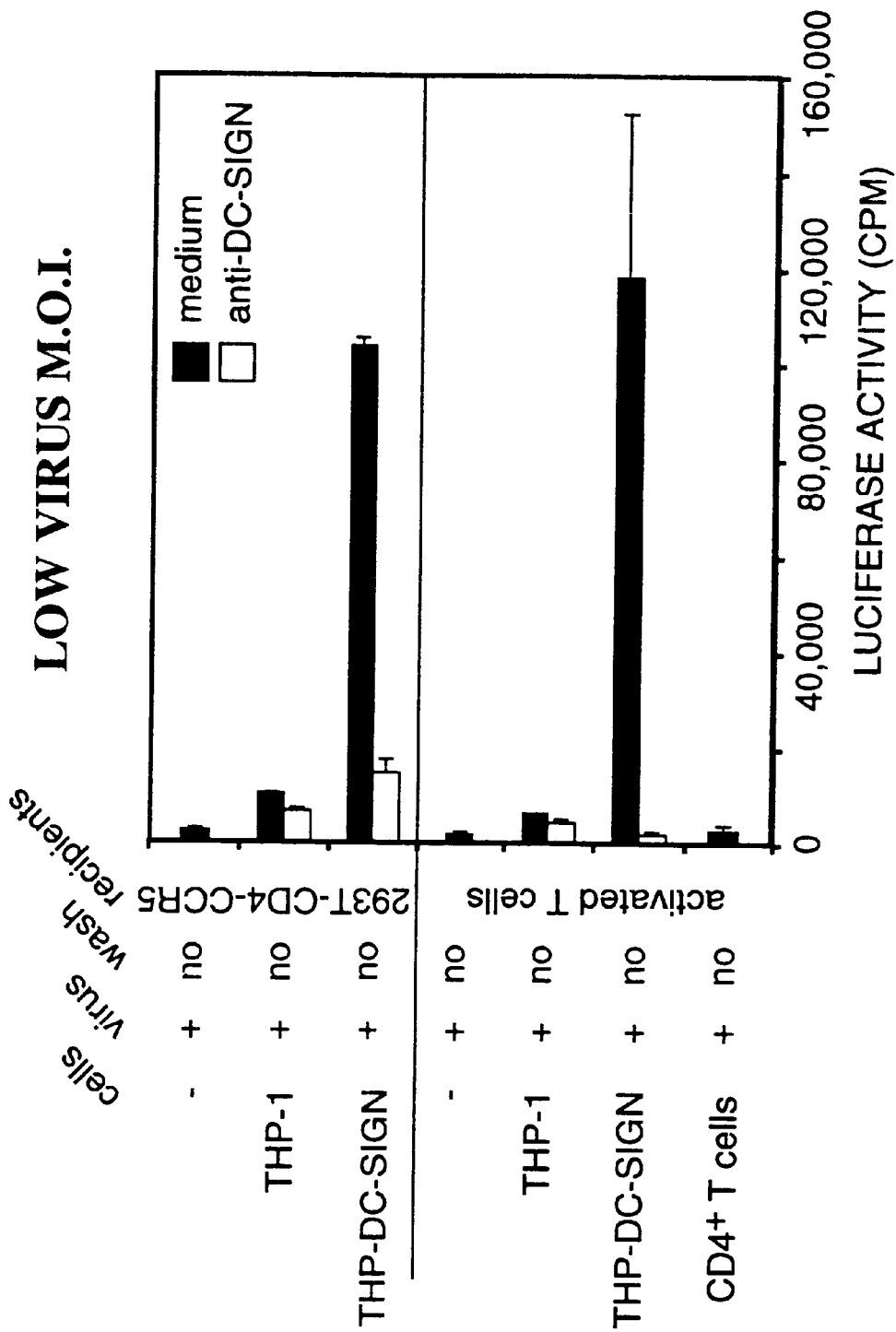

FIG. 6A
FIG. 6B
FIG. 6C
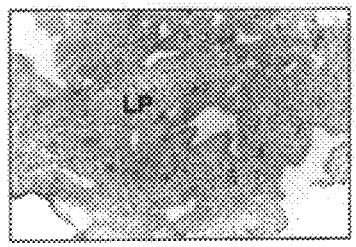  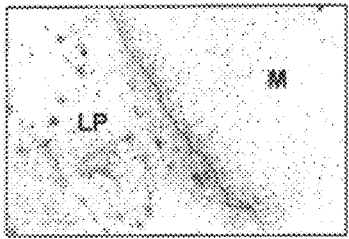
FIG. 6D
FIG. 6E
FIG. 6F
DC-SIGN
CD4
CCR5
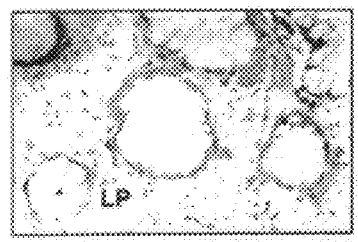  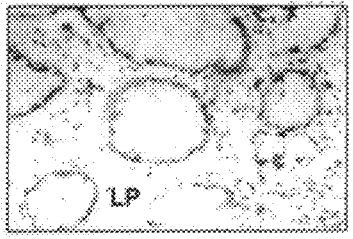
  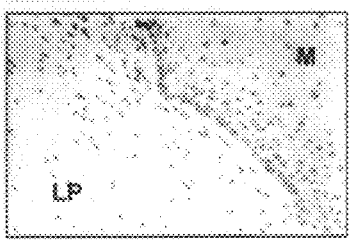
FIG. 6G
FIG. 6H
FIG. 6I

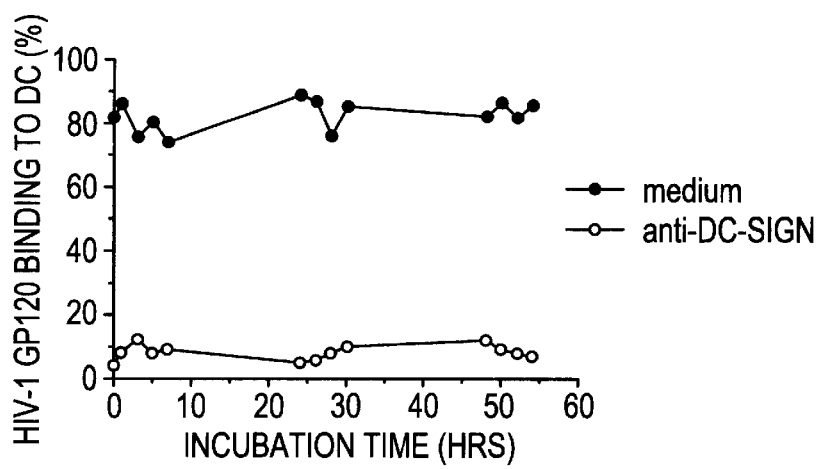
FIG. 7A
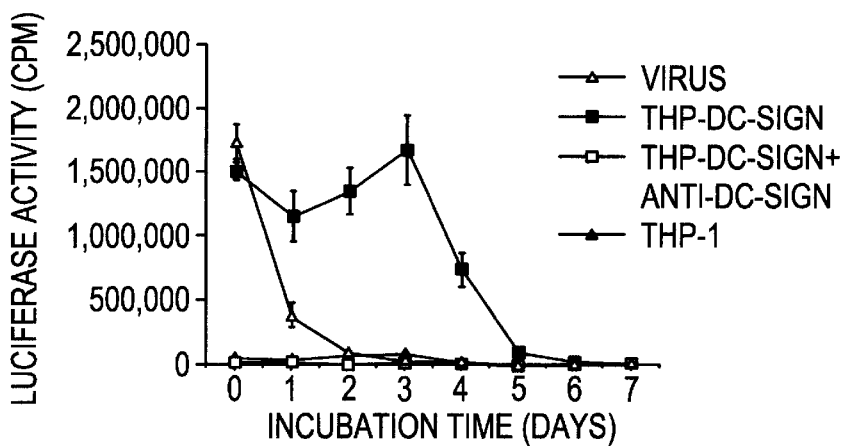
FIG. 7B
FIG. 7C
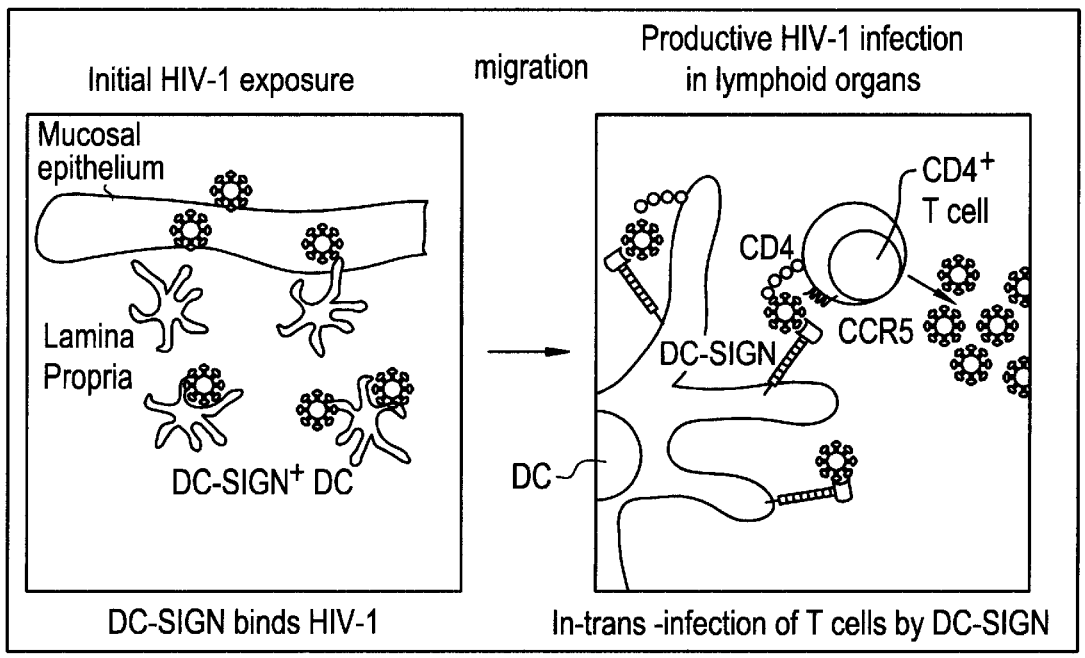

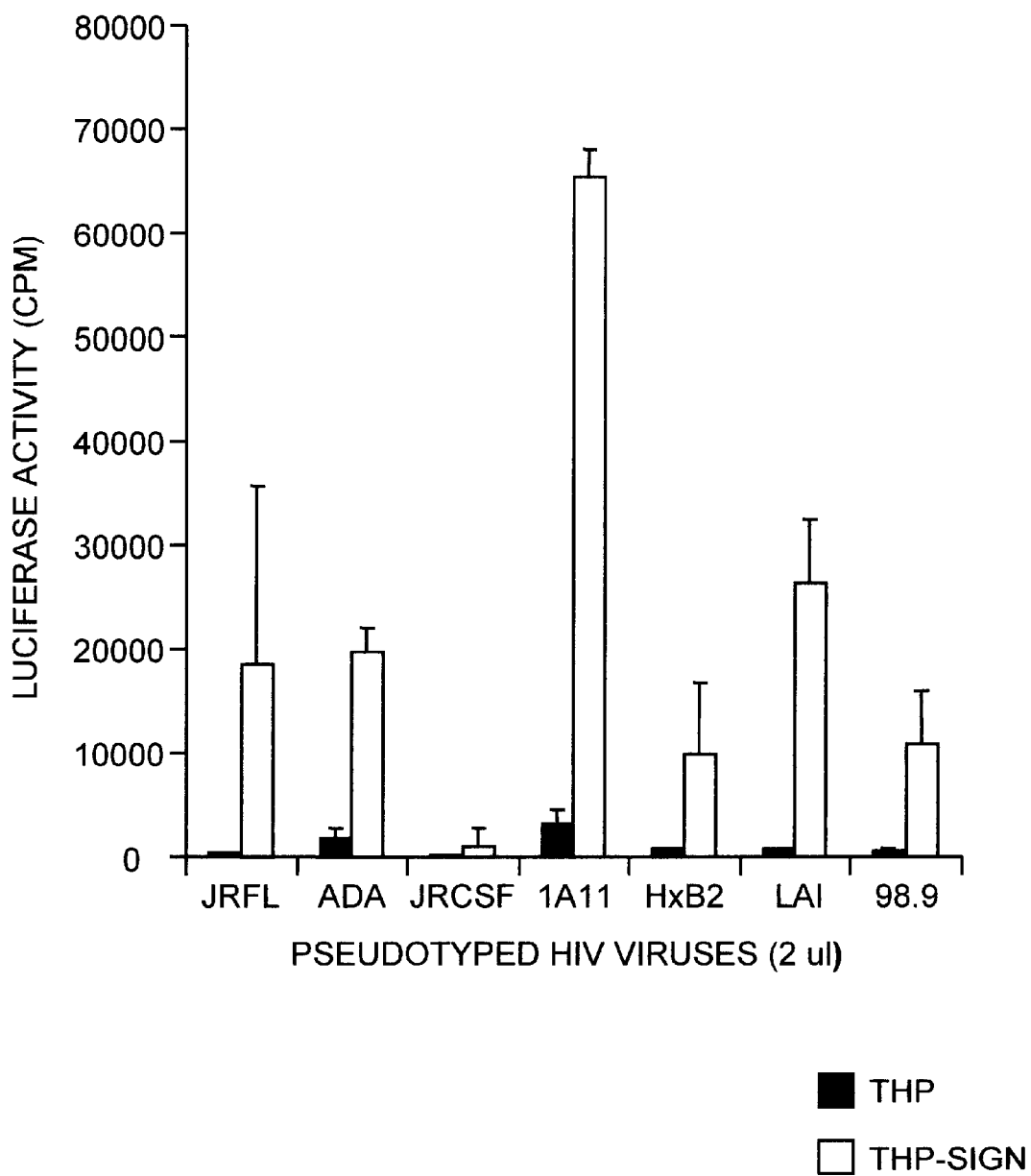

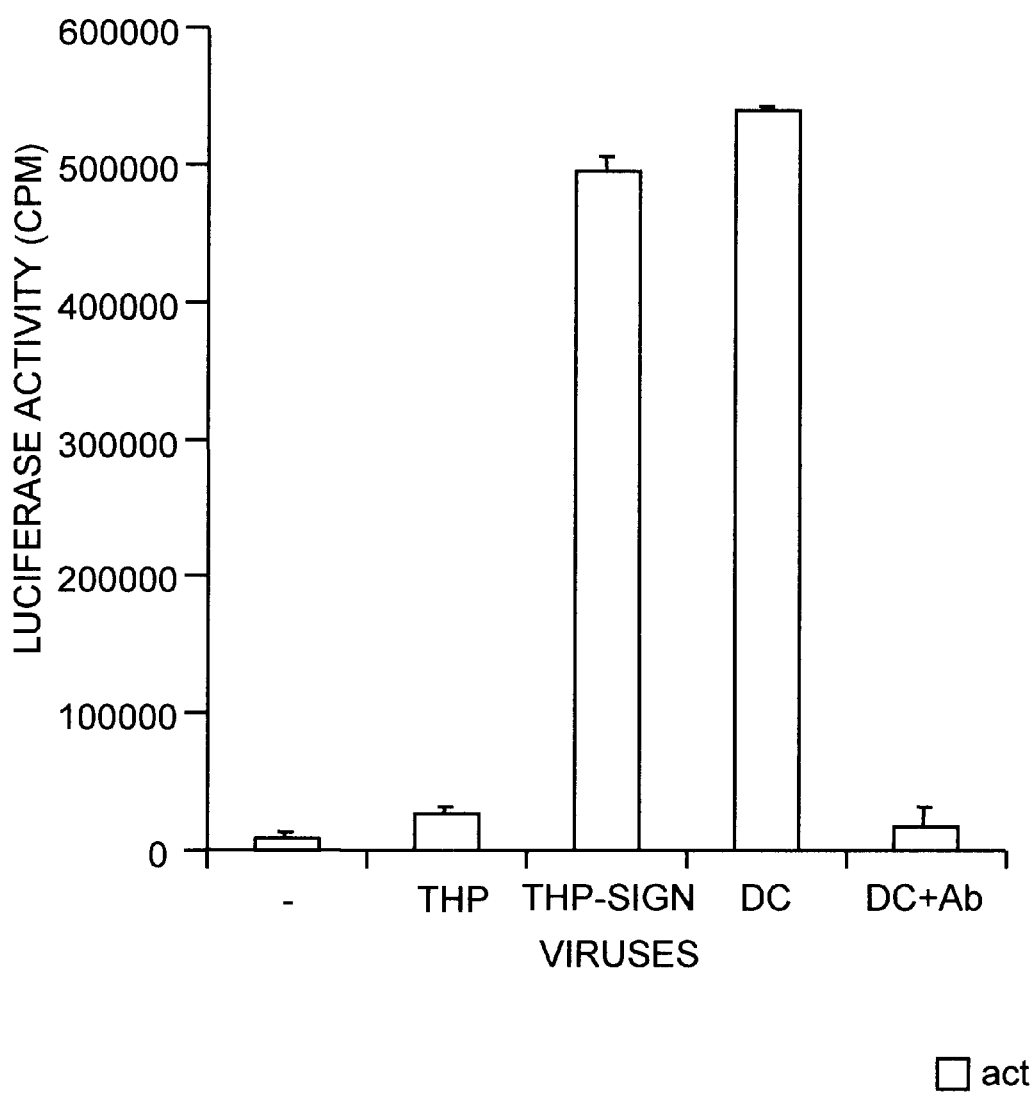

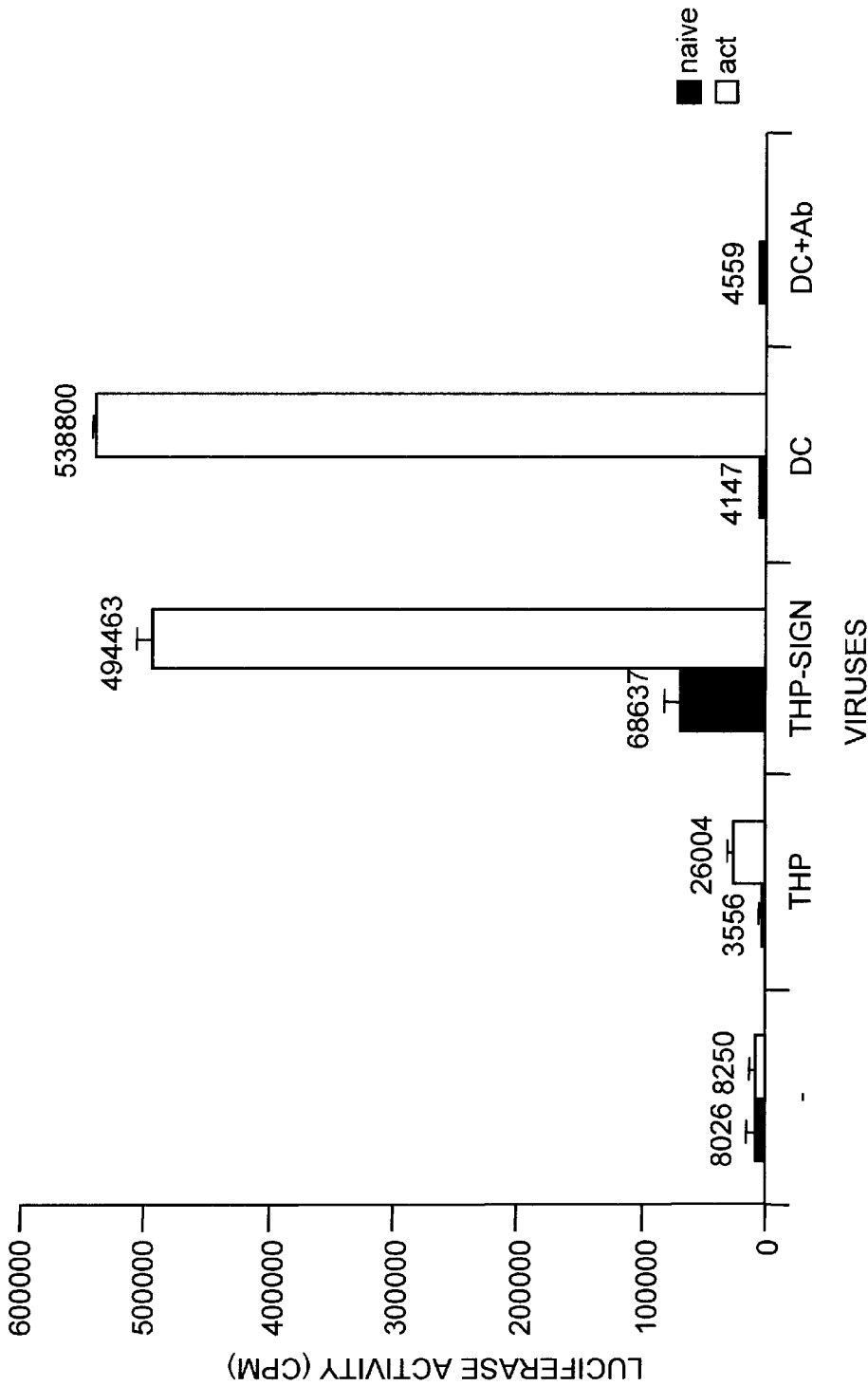

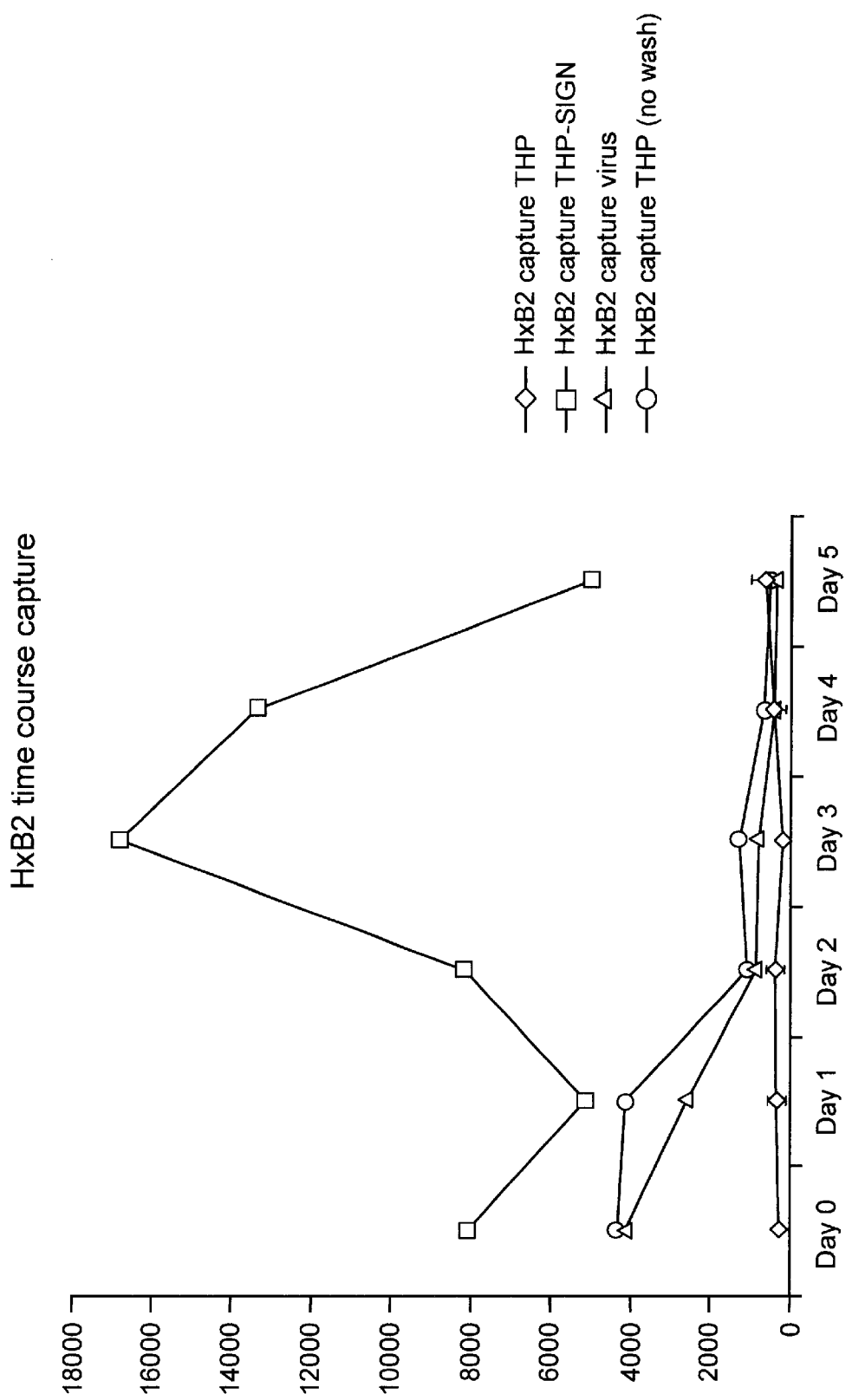

IDENTIFYING COMPOUNDS INHIBITING DC-SIGN FACILITATION OF HIV INTO CELLS

GOVERNMENTAL SUPPORT

The research leading to the present inventions was funded in part by Grant No. AI 33856 from the National Institutes of Health. The government may have certain rights in the invention.

TECHNICAL FIELD OF THE INVENTION

The present invention relates generally to the binding, transport and infection of cells by retroviruses including HIV-1, and HIV-2. Methods of identifying agents that modulate such processes, the agents themselves and therapeutic uses of such agents are also provided. Related diagnostic methods are also included.

BACKGROUND OF THE INVENTION

The human immunodeficiency viruses infect $CD4^{30}$ macrophages and T helper cells. Although HIV-1 entry requires cell surface expression of CD4, to which the viral envelope glycoproteins bind, several studies have suggested that it is not sufficient for fusion of the viral envelope to the cellular plasma membrane. Early studies have shown that while human cells expressing a transfected CD4 gene were permissive for virus entry, murine cells expressing human CD4 were not. These findings led to the suggestion that there is a species-specific cell surface cofactor required in addition to CD4 for HIV-1 entry. Subsequent studies have shown that strains of HIV-1 that had been adapted for growth in transformed T-cell lines (T-tropic strains) could not infect primary monocytes or macrophages; in contrast, primary viral strains were found to infect monocytes and macrophages, but not transformed T cell lines. This difference in tropism was found to be a consequence of specific sequence differences in the gp120 subunit of the envelope glycoprotein, suggesting that multiple cell type-specific cofactors may be required for entry in addition to CD4.

The nature of the cofactors required for HIV entry proved elusive until it was recently discovered that the principal receptor for entry of macrophage-tropic (M-tropic) HIV-1 strains was CCR5, whereas the principal receptor for entry of T-cell line-tropic (T-tropic) strains was CXCR4. On the other hand, both M-tropic and T-tropic strains of simian immunodeficiency virus (SIV) can be mediated by CCR5, but not CXCR4 [Chew et al., *J. Virol*, 71:2705–2714 (1997); Marcon et al., *J. Virol*, 71:2522–2527 (1997); and Edinger et al., *Proc. Natl. Acad. Sci. U.S.A.*, 94:4005–4010 (1997)]. More importantly, SIV strains were also found to infect $CD4^{30}$ cells that lack CCR5 [Chen et al., *J. ViroL.*, 71:2705–2714 (1997); and Edinger et al, *Proc. Natl. Acad. Sci. U.S.A.*, 94:4005–4010 (1997)].

In humans, CCR5-tropic viruses are primarily involved in transmission, while viruses with broader tropism, particularly for CXCR4, emerge during progression to immunodeficiency [Fauci, *Nature*, 384:529–534 (1996)]. It is not yet known whether appearance of CXCR4-tropic viruses is a consequence or the cause of immune system decline. Insight into this key problem of virus evolution is likely to require experimental manipulation in animal models. Infection of non-human primates with SIV is remains the only good animal model for studying pathogenesis of the immunodeficiency viruses [Desrosiers, *Annu Rev Immunol*, 8:557–578 (1990)]. Moreover, different species of non-human primates vary widely in their responses to SIV infection. For example, Rhesus macaques succumb to immunodeficiency that closely resembles AIDS in humans, but sooty mangabeys and African green monkeys can sustain infection with little evidence of immune system damage [Kestler, *Science*, 248:1109–1112 (1990)]. These interspecies differences provide important clues for understanding and combating disease progression in HIV-infected humans.

Transmission of Human Immunodeficiency Virus Type 1 (HIV-1) infection in humans requires the dissemination of virus from sites of infection at mucosal surfaces to T cell zones in secondary lymphoid organs, where extensive viral replication occurs in $CD4^{30}$ T-helper cells and macrophages [Fauci, *Nature*, 384(6609):529–534 (1996)]. These cells express both CD4 and the chemokine receptor CCR5, which together form the receptor complex required for entry by the R5 viral isolates that are prevalent early after infection [Littman, *Cell*, 93:677–680 (1998); Lu et al., *Proc. Natl. Acad. Sci. U.S.A.*, 94(12):6426–6431 (1997); Dragic et al, *Nature*, 381:667–673 (1996); U.S. Pat. No: 5,939,320, Issued Aug. 17, 1999; and U.S. patent application 09/116, 498, Filed Jul. 7, 1998, the contents of which are hereby incorporated by reference in their entireties]. Viruses with tropism for other chemokine receptors, particularly CXCR4, are rarely transmitted, and generally appear only late in infection. Such CXCR4-tropic isolates replicate poorly in macrophages, and it has hence been proposed that infection of macrophages is a requisite component of viral transmission.

The mechanism of early viral dissemination remains vague, but based on anatomical distribution of different hematopoietic lineage cells and on in vitro infectivity studies it has been inferred that immature dendritic cells (DC) residing in the skin and at mucosal surfaces are the first cells targeted by HIV-1. DC are the most potent antigen-presenting cells in vivo [Banchereau and Steinman, *Nature*, 392:245–252 (1998); Valitutti et al., *Nature*, 375:148–151 (1995)]. Immature DC in peripheral tissues capture antigens efficiently and have a unique capacity to subsequently migrate to the T cell areas of secondary lymphoid organs. As the cells travel, they mature and alter their profile of expression of cell surface molecules, including chemokine receptors, lose their ability to take up antigen, and acquire competence to attract and activate resting T cells in the lymph nodes [Banchereau and Steinman, *Nature*, 392:245–252 (1998); Adema et al., *Nature*, 387(6634) :713–717 (1997)]. HIV-1 is thought to subvert the trafficking capacity of DC to gain access to the $CD4^+$to T cell compartment in the lymphoid tissues [Steinman and Inaba, *J. Leukoc. Biol.*, 66(2):205–208 (1999); Rowland-Jones, S. L., *Curr. Biol.*, 9(7):R248–R250 (1999); and Grouard and Clark, *Curr. Opin. Immunol.*, 9(4):563–567 (1997)].

Immature DC express CD4 and CCR5, albeit at levels that are considerably lower than on T cells [Granelli-Pipemo et al., *J. Exp. Med.*, 184:2433–2438 (1996); Rubbert et al, *J. Immunol.*, 160(8):3933–3941 (1998)], and they have been reported to be injectable with R5 strains of HIV-1. In contrast, immature DC do not express CXCR4 and are resistant to infection with CXCR4-tropic isolates of HIV-1 [Granelli-Pipemo et al., *J. Virol.*, 72:2733–2737 (1998); Blauvelt et al., *J. Clin. Invest.*, 100:2043–2053 (1997); and Weissman et al., *Proc. Natl. Acad. Sci. U.S.A.*, 92:826–830 (1995)]. Entry of HIV-1 into immature DC has also been reported to proceed through a CD4-independent mechanism [Blauvelt et al., *J. Clin. Invest.*, 100:2043–2053 (1997)], suggesting that receptors other than CD4 could be involved. There have been conflicting reports regarding the significance of HIV-1 replication within DC [Canque et al., *Blood*, 93(11):3866–3875 (1999); Ayehunie et al., *Blood*, 90(4):1379–1386 (1997); Cameron et al., *J. Leukoc. Biol.*, 56(3):257–265 (1994)]. Although replication can be observed in some circumstances, it has also been reported that, in immature DC, replication is incomplete and that only early HIV-1 genes are transcribed.

It has been proposed that virus-infected immature DC migrate to the draining lymph nodes where they initiate both a primary anti-viral immune response and a vigorous productive infection of T cells, allowing systemic distribution of HIV-1 [Cameron et al., *Science*, 257(5068):383–387 (1992); Weisman et al., *Proc. Natl. Acad. Sci. U.S.A.*, 92:826–830 (1995)]. However, in a non-human primate model of mucosal infection with the simian immunodeficiency virus, it has been difficult to demonstrate productive infection of DC despite rapid dissemination of virus [Stahl-Henning et al., *Science*, 285(5431):1261–1265 (1999)]. Other efforts to model primary HIV-1 infection in vitro by exposing DC derived from skin or blood to HIV-1 have indicated that these cells are poorly infected. Nevertheless, only DC, and not other leukocytes including monocytes, macrophages, B cells and T cells were able to induce high levels of infection upon co-culture with mitogen-activated CD4[30] T cells after being pulsed with HIV-1 [Cameron et al., *Science*, 257(5068):383–387 (1992); Granelli-Pipemo et al., *Curr. Biol.*, 9:21–29 (1999); Weissman et al., *Proc. Natl. Acad. Sci. U.S.A.*, 92:826–830 (1995); Blauvelt et al., *J. Clin. Invest.*, 100:2043–2053 (1997); Cameron et al., *J. Leukoc. Biol.*, 59(2):158–171 (1996)]. In an early study, Cameron et al. [*Science*, 257(5068):383–387 (1992)] proposed that DC have a unique ability to "catalyze" infection of T cells with HIV, but do not become infected themselves.

Therefore, there is a need to identify the protein or proteins involved in the mediation of HIV from the mucosal surfaces to the T cell areas of secondary lymphoid organs.

Further, there is a need to design methods of identifying agents that will interfere with this mediation.

The citation of any reference herein should not be construed as an admission that such reference is available as "Prior Art" to the instant application.

SUMMARY OF THE INVENTION

The present invention provides the missing link between viral breach of host mucosal defense and infection of T cells in the lymphatic organs by demonstrating that a membrane-bound receptor that is specifically expressed on dendritic cells, DC-SIGN, and which has the amino acid sequence of SEQ ID NO:2, facilitates infection of T lymphocytes by HIV. The present invention further provides new intervention strategies and novel approaches towards prevention, preventive vaccination and therapy against HIV infection based, at least in part, on this finding.

The present invention therefore provides an antibody that is specific for an antigenic fragment of gp120. In one embodiment the antigenic fragment is obtained from a portion of gp120 that binds to DC-SIGN. In another embodiment the antigenic fragment is obtained from the portion of gp120 that is exposed upon gp120 binding of DC-SIGN due to the concomitant conformational change that occurs upon DC-SIGN binding gp120. The present invention also provides antibodies to the portion of DC-SIGN that interacts with T cells and/or macrophages. In a preferred embodiment the antibody is specific for the DC-SIGN-gp120 binding complex. The antibodies of the present invention preferably interfere with dendritic cells facilitating the trans-enhancement of HIV entry into T cells or macrophages.

In a particular embodiment the antibody is a polyclonal antibody. In another embodiment the antibody is a monoclonal antibody. In still another embodiment the antibody is a chimeric antibody. In one such embodiment the antibody is a humanized antibody. The present invention also provides immortal cell lines that produce the monoclonal antibodies of the present invention.

The present invention also provides vaccines and immunogenic compositions. Such vaccines and immunogenic compositions preferably comprise adjuvants. One such immunogenic composition comprises an adjuvant and an antigenic fragment obtained from a portion of gp120 that binds to DC-SIGN. In another embodiment the immunogenic composition comprises an adjuvant and an antigenic fragment obtained from the portion of gp120 that is exposed upon gp120 binding of DC-SIGN due to the concomitant conformational change that occurs upon DC-SIGN binding gp120. In yet another embodiment the immunogenic composition comprises an adjuvant and an antigenic fragment of DC-SIGN that interacts with T cells and/or macrophages. In still another embodiment the immunogenic composition comprises an adjuvant and the DC-SIGN-gp120 binding complex or fragment thereof.

The present invention further provides a soluble form of human DC-SIGN. The soluble form of human DC-SIGN can be used in drag assays or in a pharmaceutical composition further comprising a pharmaceutically acceptable carrier.

In addition, the present invention provides a mammalian cell that is transfected with a vector encoding human DC-SIGN. Preferably this cell can facilitate the trans-enhancement of HIV entry into a T cell or macrophage. More preferably, the cell lacks the translocation promoting agent and/or CD4 required for HIV entry. In a particular embodiment the mammalian cell is not a dendritic cell. In a preferred embodiment the mammalian cell is a human cell. In particular embodiment, the cell is attached to a solid support matrix.

The present invention further provides methods of filtering a biological fluid to remove a virus expressing an HIV envelope glycoprotein that binds DC-SIGN. In one embodiment the method comprises passing the biological fluid through a solid support comprising DC-SIGN. A related embodiment comprises passing the biological fluid through a solid support comprising a mammalian cell that is transfected with a vector encoding human DC-SIGN. In another embodiment the biological fluid is contacted with a mammalian cell that is transfected with a vector encoding human DC-SIGN and then the cell is removed. In still another embodiment the biological fluid is contacted with a dendritic cell and then the dendritic cell is removed.

The present invention further provides transgenic non-human mammals. In one embodiment the transgenic non-human mammal comprises DNA constructs encoding CD4, one or more translocation promoting agents, and DC-SIGN. Preferably the CD4, the translocation promoting agent(s), and the DC-SIGN are human proteins. In a preferred embodiment, the transgenic non-human mammal is capable of/susceptible to mucosal uptake of HIV, transport of the HIV to lymphatic organs and infection of a target T cell and/or macrophage by HIV. More preferably the infection with HIV (or suitable vector analog) is greatly enhanced relative to a transgenic non-human mammal that does not contain a DNA construct encoding DC-SIGN. In a preferred embodiment the transgenic non-human mammal further comprises a DNA construct encoding cyclin T (which is preferably human cyclin T).

In one embodiment the human translocation promoting agent is CCR3. In another embodiment the hum an translocation promoting agent is CXCR4. In yet another embodiment the human translocation promoting agent is CCR4b. In still another embodiment the human translocation promoting agent is Bob. In yet another embodiment the human translocation promoting agent is Bonzo. In a preferred embodiment the human translocation promoting agent is CCR5.

The transgenic non-human mammal can be any mammal including a primate or rodent including rabbits, rats or monkeys and chimpanzees. In a preferred embodiment the transgenic non-human mammal is a mouse.

The present invention further provides methods of treating or preventing HIV infection by inhibiting dendritic cells from facilitating the trans-enhancement of HIV entry into a cell. One such embodiment comprises administering a humanized form of an antibody of the present invention to the subject. Another embodiment comprises administering a soluble form of DC-SIGN of the present invention to the subject. Yet another embodiment comprises administering a compound identified through an assay of the present invention to the subject. In a preferred embodiment, the cell for which the trans-enhancement of HIV entry is inhibited is a T cell or macrophage.

The present invention further provides methods of identifying a compound that interferes with the trans-enhancement of HIV entry into a cell. In one such embodiment, the compound interferes with viral capture. One such embodiment comprises contacting a first cell with a vector in the presence of a test compound. The vector comprises a viral envelope protein that binds DC-SIGN, whereas the first cell expresses DC-SIGN. A DC-SIGN-viral envelope protein complex forms between the first cell and the vector in the absence of the test compound and the effect of the test compound on the formation of the complex is thus being tested. The unbound vector is separated from the first cell (preferably so is the test compound) and the first cell is next contacted with a second cell. The second cell is susceptible to entry of vectors comprising the viral envelope protein. The amount of vector that has entered the second cell is determined. A test compound is identified as a compound that interferes with the trans-enhancement of HIV entry into a cell when the amount of vector entry determined is less for the case when the test compound was present during the incubation with the first cell and the vector, than when the test compound was absent.

In a particular embodiment removal of the unbound vector (and the test compound) from first cell comprises washing the unbound vector (and the test compound) away from the first cell. In a particular embodiment the second cell is a T cell or macrophage. In another embodiment the second cell expresses human CD4 and a human translocation promoting agent. In one embodiment the human translocation promoting agent is CCR3. In another embodiment the human translocation promoting agent is CXCR4. In yet another embodiment the human translocation promoting agent is CCR2b. In still another embodiment the human translocation promoting agent is Bob. In yet another embodiment the human translocation promoting agent is Bonzo. In a preferred embodiment the human translocation promoting agent is CCR5.

In a particular embodiment the human translocation promoting agent is CCR5 and the viral envelope glycoprotein is JRFL. In another embodiment the vector contains a marker protein. In one such embodiment the amount of vector that has entered the second cell is determined by detecting the amount of marker protein expressed in the cell. In a particular embodiment the marker protein is luciferase. In another embodiment the marker protein is green fluorescent protein. The present invention further provides the compounds identified by these methods.

The present invention also provides an assay for identifying an agent for use in the treatment or prevention of HIV infection using a transgenic non-human mammal of the present invention. One such method comprises administering a test compound to the transgenic non-human mammal and infecting the transgenic non-human mammal with a virus or viral vector having an HIV envelope glycoprotein. The ability of the transgenic non-human mammal to resist the infection is then determined or measured. A test compound is identified as an agent for use in the treatment or prevention of HIV infection when the measured ability of the transgenic mammal to resist the infection is statistically greater in the presence of the test compound than in the absence of the test compound. Again the compounds identified by this method are also part of the present invention.

The present invention further provides a method of identifying a compound that interferes with the trans-enhancement of HIV entry into a cell. One such embodiment comprises contacting a first cell, a vector and a second cell in the presence of a test compound. The vector comprises a viral envelope protein that binds DC-SIGN, the first cell expresses DC-SIGN, and a DC-SIGN-viral envelope protein complex forms between the first cell and the vector in the absence of the test compound. In addition, the second cell is susceptible to entry of vectors comprising the viral envelope protein. The amount of vector that has entered the second cell is then determined. A test compound is identified as a compound that interferes with the trans-enhancement of HIV entry into a cell when the amount of vector entry is less in the presence of the test compound than in its absence. In a particular embodiment the second cell is a T cell or macrophage. In another embodiment the second cell expresses human CD4 and a human translocation promoting agent. In one embodiment the human translocation promoting agent is CCR3. In another embodiment the human translocation promoting agent is CXCR4. In yet another embodiment the human translocation promoting agent is CCR2b. In still another embodiment the human translocation promoting agent is Bob. In yet another embodiment the human translocation promoting agent is Bonzo. In a preferred embodiment the human translocation promoting agent is CCR5.

In a particular embodiment the human translocation promoting agent is CCR5 and the viral envelope glycoprotein is JRFL. In another embodiment the vector contains a marker protein. In one such embodiment the amount of vector that has entered the second cell is determined by detecting the amount of marker protein expressed in the cell. In a particular embodiment the marker protein is luciferase. In another embodiment the marker protein is green fluorescent protein. The present invention further provides the compounds identified by these methods. Accordingly, it is a principal object of the present invention to provide compounds that can be used in the treatment of AIDS.

It is a further object of the present invention to provide assays for identifying new compounds in the treatment of HIV infection.

It is a further object of the present invention to provide soluble fragments of DC-SIGN.

It is a further object of the present invention to generate a soluble form of DC-SIGN that inhibits trans-enhancement of HIV entry into T cells that is facilitated by DC-SIGN.

It is a further object of the present invention to identify DC-SIGN polymorphisms that do enable dendritic cells to facilitate trans-enhancement of HIV entry in T cells.

It is a further object of the present invention to provide methods of identifying drugs that can treat HIV infection.

It is a further object of the present invention to provide methods for making a transgenic animal model for AIDS.

It is a further object of the present invention to provide a vaccine to prevent or retard the onset of AIDS.

These and other aspects of the present invention will be better appreciated by reference to the following drawings and Detailed Description.

BRIEF DESCRIPTION OF THE DRAWINGS

FIGS. 1A–1D show that DC-SIGN is a dendritic cell (DC) specific receptor for HIV-1 gp120. FIG. 1A shows that DC-SIGN is expressed specifically by DC. Immature DC, cultured from monocytes in the presence of GM-CSF and IL-4, express high levels of DC-SIGN, whereas resting peripheral blood lymphocytes or monocytes do not express DC-SIGN. Expression of DC-SIGN (AZN-D1) was determined by FACScan analysis. One representative experiment out of 3 is shown. FIG. 1B shows that DC-SIGN, but not CD4, mediates binding of HIV-1 gp120 to DC. DC were allowed to bind HIV-1 gp120-coated fluorescent beads. Adhesion was blocked by anti-DC-SIGN antibodies (20 μg/ml), mannan (20 μg/ml) and EGTA (5 mM) and not by neutralizing anti-CD4 antibodies (20 μg/ml). One representative experiment out of 3 is shown. FIGS. 1C–1D show immature DC (FIG. 1D) express low levels of CD4 (RPA-T4) and CCR5 (2D7/CCR5) and high levels of DC-SIGN (AZN-D1). THP-1 cells stably transfected with DC-SIGN (THP-DC-SIGN, FIG. 1C) express high levels of DC-SIGN (AZN-D1) while CD4 and CCR5 are not expressed (filled histograms). Antibodies against CD4 and DC-SIGN were isotype matched and the appropriate isotype controls are represented by dotted lines.

FIG. 2A shows that antibodies against DC-SIGN inhibit HIV-1 infection as measured in a DC-T cell co-culture. DC($50\times10^3$) were pre-incubated for 20 min at room temperature with blocking mAb against CD4 (RPA-T4) or DC-SIGN (AZN-D1 and AZN-D2) (20 μg/ml) or with a combination of CCR5-specific chemokines (CCR5 trio: RANTES, MIP-1α and MIP1β; 500 ng/ml). Pre-incubated immature DC were pulsed for 2 hours with HIV-1 (M-tropic HIV-$1_{Ba-L}$ strain) and unbound virus particles and mAb were washed away. Subsequently, DC were co-cultured with activated PBMC ($50\times10^3$) for 9 days. Co-culture supernatants were collected and p24 antigen levels were measured by ELISA. One representative experiment of 2 is shown. FIG. 2B shows the inhibition of HIV-1 infection in a DC-T cell co-culture by blocking DC-SIGN, CD4 and CCR5. HIV-1 replication in the DC-T cell co-culture at day 5 of the experiment is described in FIG. 5A. The results of day 5 are representative for day 6, 7 and 9 of DC-T cell co-culture. DC were also pre-incubated with mnAb against DC-SIGN together with anti-CD4 and CCR5 specific chemokines. p24 values represent mean ±SD of triplicate cultures. One representative experiment out of 2 is shown. FIG. 2C shows the DC-SIGN interactions with ICAM-3 are not involved in the transmission of DC-bound-HIV-1 to T cells. DC $50\times10^3$) were pulsed for 2 hours with HIV-1 (M-tropic HIV-$1_{Ba-L}$ strain), washed and co-cultured with activated PBMC $50\times10^3$) for 9 days in the presence of the CCR5 specific chemokines (CCR5 trio: RANTES, MIP-1α and MIP1β; 500 ng/ml) or mnAb against CD4 (RPA-T4) and DC-SIGN (AZN-D1 and AZN-D2) (20 μg/ml). Antibodies were added post HIV-1 infection of DC, prior to the addition of PBMC. One representative experiment out of 2 is shown.

FIG. 3A shows the results from 293T cells that were transfected with DC-SIGN or CD4 and CCR5 and pulsed for 2 hour with HIV-1 (CCR5-tropic HIV-$1_{Ba-L}$ strain). Subsequently, cells were cultured for 9 days. Supernatants were collected and p24 antigen levels were measured by ELISA. One representative experiment of 2 is shown. FIG. 3B shows the results from 293T cells and 293T cells stably expressing either CD4, CCR5 or CD4 and CCR5 that were transiently transfected with DC-SIGN and subsequently infected with pseudotyped CCR5-tropic HIV-$1_{ADA}$ virus in the presence of polybrene (20 μg/ml). Luciferase activity was evaluated after 2 days. One representative experiment out of 3 is shown. FIG. 4A shows that DC-SIGN captures HIV-1 and facilitates infection of HIV-1 permissive cells in trans. THP-1 transfectants ($100\times10^3$) were pre-incubated for 20 min at room temperature with blocking mAb against DC-SIGN (AZN-D1 and AZN-D2; 20 μg/ml). The THP-DC-SIGN cells were infected with HIV-luciferase virus pseudotyped with R5 strain HIV-$1_{ADA}$ Env. Alternatively activated T cells were infected with pseudotyped HIV-$1_{ADA}$ virus. After 2 hours at 37° C. the infected cells were extensively washed and added to either 293T-CD4-CCR5 cells or activated primary T cells $100\times10^3$). HIV-1 infection was determined after 2 days by measuring the luciferase activity. One representative experiment out of 3 is shown. FIG. 4B shows that DC-SIGN is able to mediate capture of HIV-1 viruses pseudotyped with M-tropic HIV-1 envelopes from different primary isolates. DC-SIGN mediated capture was performed as described in FIG. 4A on 293T-CD4-CCR5 cells with HIV-luciferase viruses pseudotyped with the CCR5-specific HIV-1 envelopes from JRFL, JRCSF and from primary viruses 92U.S.715.6, 92BR020.4 and 93TH966.8. One representative experiment out of 2 is shown. FIG. 4C shows that activated T cells are infected by HIV-1 in the T cell/THP-DC-SIGN co-culture. THP-DC-SIGN cells were incubated with HIV-eGFP viruses pseudotyped with M-tropic HIV-$1_{ADA}$ and subsequently co-cultured with activated T cells. The CD3-negative THP-DC-SIGN cells were not infected by HIV-1 whereas the CD3-positive T cells were infected. T cells, gated by staining for CD3 (tricolor), were positive for GFP, whereas CD3-negative THP-DC-SIGN that initially captured HIV-GFP did not express GFP. One representative experiment out of 2 is shown.

FIGS. 5A–5B show that DC-SIGN enhances HIV-1 infection of T cells by acting in trans. At a low virus load, DC-SIGN in trans is crucial for the infection of HIV-1 permissive cells. THP-1 transfectants $100\times10^3$) were pre-incubated for 20 min at room temperature with blocking mAb against DC-SIGN (AZN-D1 and AZN-D2; 20 μg/ml). The THP-1 were infected by low amounts of pseudotyped HIV-$1_{ADA}$ virus (FIG. 5A) or other R5 isolates of HIV-1 (5B), i.e. at the threshold of detection in a single round infection assay. After 1 hour at 37° C. the cell/virus suspension was directly added to either 293T-CD4-CCR5 or activated T cells 100×10³). The infectivity was determined after 2 days by measuring the luciferase activity. One representative experiment out of 2 is shown.

FIGS. 6A–6I show that DC-SIGN is expressed on DC present in mucosal tissue that do not express CCR5. Immunohistochemical analysis of DC-SIGN expression on mucosal tissue sections. FIGS. 6A–6C show different tissue sections that were stained with anti-DC-SIGN mAb: cervix (FIG. 6A) rectum (FIG. 6B) and uterus (FIG. 6C) (original magnification: 200×). All mucosal tissues contain DC-SIGN positive cells in the lamina propria. Staining of serial sections demonstrate that these DC-SIGN positive cells do not express CD3, CD20, CD14 and CD68. FIGS. 6D–6I show the immunohistochemical staining of serial sections of rectum (FIGS. 6D–6F) and uterus (FIGS. 6G–6I) with antibodies against DC-SIGN (FIGS. 6A and 6D), CD4 (FIGS. 6B and 6E) or CCR5 (FIGS. 6C and 6F).

FIGS. 7A–7C show that DC-SIGN captures HIV-1 and retains long-term infectivity FIG. 7A shows the time course of HIV-1$_{MN}$ gp120 binding to THP-DC-SIGN. DC-SIGN positive cells were incubated with gp120 coated beads. Beads bound for more than 60 hrs as determined by FAC-Scan analysis. FIG. 7B shows that DC-SIGN binds HIV-1 and retains for more than four days virus that infects T cells in trans. THP/THP-SIGN cells were pulsed for 4 hours with HIV-1 pseudotyped virus in the presence or absence of anti-DC-SIGN antibodies (AZN-D1 and AZN-D2, 20 μg/ml). After washing the HIV-1 pulsed cells were cultured at 37° C. for several days. As a control identical amounts of virus were incubated at 37° C. in medium without cells. Every day aliquots of the HIV-1 pulsed cells were added to HIV-1 permissive 293T-CD4-CCR5 cells in order to measure infectivity. Lysates to examine luciferase activity were obtained after 2 days of co-culture. FIG. 7C depicts a model of HIV-1 co-opting DC-SIGN as a trans-receptor after initial exposure. DC are the primary cells targeted by HIV-1 during mucosal exposure and are DC-SIGN-positive. HIV-1 adheres to DC-SIGN via a high affinity interaction, and the immature DC carrying HIV-1 migrates to the lymphoid tissues. Upon arrival, DC will cluster with T cells and DC-SIGN enhances HIV-1 infection of T cells in trans leading to a productive and sustained infection.

FIG. 8 shows that DC-SIGN mediates capture of SIV and R5, X4, and dual tropic HIV. Viruses encoding the reporter gene luciferase were pseudotyped with envelopes from the CCR5 tropic strains JRFL, ADA, and JRCSF; the CXR4 tropic strains HxB2 and LAI; the dual tropic strain 89.6; and SIV 1A11. THP or THP-DCSIGN cells were pulsed with these viruses, washed, and then added to target cells. Luciferase activity was measured as an indicator of viral infection of targets.

FIG. 10 shows the enhancement of CXR4 tropic HIV infection of activated T cells. THP, THP-DCSIGN cells, DC (dendritic cells), or DC preincubated with anti DCSIGN antibody, were incubated with HxB2 pseudotyped virus encoding the luciferase reporter gene, followed by addition of activated T cell targets.

FIG. 11 shows the enhancement of CXR4 tropic HIV infection of unactivated T cells. (See FIG. 10 for assay conditions; the same assay was performed except unactivated T cells were examined).

FIG. 12 shows that binding to DC-SIGN extends the longevity of HxB2. THP or THP-DCSIGN cells were pulsed with HxB2, washed, and then added to target cells at different time points as indicated following the viral pulse. "HxB2 capture virus" refers to virus in medium alone.

DETAILED DESCRIPTION OF THE INVENTION

Figure 1E:
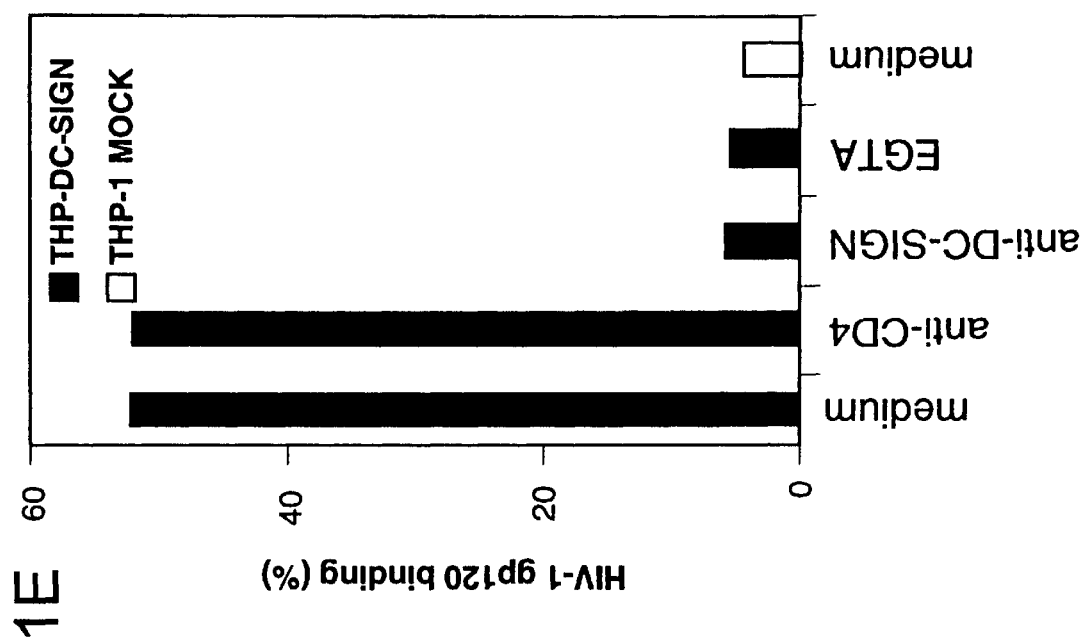
FIG. 1E shows DC-SIGN transfectants (THP-DC-SIGN) bind HIV-1 gp120. THP-DC-SIGN and mock transfectants were allowed to bind HIV-1 gp120 coated fluorescent beads. Adhesion was blocked by anti-DC-SIGN antibodies (20 μg/ml) and EGTA (5 mM) and not by neutralizing anti-CD4 (RPA-T4) antibodies (20 μg/ml). One representative experiment out of 3 is shown.

The present invention provides the properties of a dendritic cell-specific C-type lectin, DC-SIGN, that is highly expressed on dendritic cells (DC) present in mucosal tissues and binds to the HIV-1 envelope glycoprotein gp120. DC-SIGN does not function as a receptor for viral entry into DC, but instead promotes efficient infection in trans of cells that express CD4 and chemokine receptors. Indeed, DC-SIGN, which is highly expressed on DC present at mucosal sites, specifically captures HIV-1 and promotes infection in trans of target cells that express CD4 and an appropriate chemokine receptor(s). These findings demonstrate that during transmission of HIV-1, the virus initially binds to mucosal DC by way of DC-SIGN, allowing subsequent transport to secondary lymphoid organs and highly efficient infection of CD4⁺ T cells by a novel trans infection mechanism.

These results predict a model in which DC-SIGN efficiently captures HIV-1 in the periphery, facilitates its transport to sites in secondary lymphoid organs rich in T cells, and enhances infection in trans of these target cells. These studies indicate that the interaction between DC-SIGN and gp120 is an important target for therapeutic intervention and vaccine development.

The present invention therefore provides a greater understanding of the mechanism through which HIV and SIV gain entrance into target cells. It has been known that the virus binds to CD4 with the aid of a chemokine receptor (such as CCR5 or CXCR4) and that cyclin T is involved. Now, with the present disclosure it is possible to describe the biochemical events involved from the initial contact of the virus with the peripheral mucosal tissues through to the initiation of fusion between the viral envelope and the cellular plasma membrane. This, in turn, allows the construction of drug screening assays to identify compounds that can interfere with these processes and thereby prevent or treat AIDS. These findings also now allow the development of small animal models for HIV infection, thus providing a better understanding of the pathogenesis of AIDS as well as a system for testing potential therapies. Indeed, such animal models, which heretofore have not been available, allow testing of drugs in an animal system prior to human trials.

The inhibition of HIV-1 infection observed in the presence of anti-DC-SIGN antibodies indicates that interfering with the gp120-DC-SIGN interaction either during the capture phase of DC in the mucosa or during DC-T cell interactions in lymphoid organs could inhibit dissemination of the virus. Small molecule inhibitors, potentially carbohydrate-based, that block the ability of gp120 to bind to DC-SIGN may be effective in prophylaxis or therapeutic intervention. Vaccine strategies aimed at eliciting mucosal antibodies that inhibit gp120 binding to DC-SIGN may also be efficacious in preventing early establishment of infection. The efficacy of gp120 vaccines has been measured as a function of the levels of neutralizing antibodies that inhibit HIV entry through CD4 and CCR5. The present results indicate that levels of antibodies that block virus binding to DC-SIGN or the DC-SIGN-mediated enhancement of infection could also be predictive of protection.

Various terms are used in the specification, which are defined as follows:

The term "translocation promoting agent" is used herein interchangeably with the terms "translocating promoter", "translocating promoting agent" and "translocating promoting protein", and refer to receptor proteins found on, or in membranes of CD4+cells that interact with and/or in conjunction in "cis" with CD4 (the human protein having the amino acid sequence of SEQ ID NO:3) in HIV and/or SIV translocation into the cell. Two translocation promoting agents exemplified in the present invention are CXCR4 (the human protein having the amino acid sequence of SEQ ID NO:4) and CCR5 (the human protein having the amino acid sequence of SEQ ID NO:5). There are at least six "known" members of the chemokine receptor family that have been shown to function in HIV-1 entry in cis with CD4 (i.e., known human translocation promoting agents) CCR5, CXCR4, CCR2b, CCR3, Bonzo (SEQ ID NO:9) and BOB (SEQ ID NO:10).

As used herein a factor that acts with a second factor to aid in the entry of HIV into a cell is said to act in "cis" when the factor is in the same membrane as the other factor, whereas a factor that acts with a second factor to aid in the entry of HIV into a cell is said to act in "trans" when the factor is in a different membrane than the other factor. Thus CD4 and CCR5 are both present in the T cell membrane and act in "cis", whereas DC-SIGN is present in the dendritic cell membrane and therefore acts in "trans" relative to either CD4 or CCR5.

As used herein, and unless otherwise specified, the terms "agent", "potential drug", "compound", "test compound" or "potential compound" are used interchangeably, and refer to chemicals which potentially have a use as an inhibitor of HIV infection and/or for use in a treatment/prevention of AIDS. Therefore, such "agents", "potential drugs", "compounds" and "potential compounds" may be used, as described herein, in drug assays and drug screens and the like.

As used herein a "small organic molecule" is an organic compound, including a peptide [or organic compound complexed with an inorganic compound (e.g., metal)] that has a molecular weight of less than 3 Kilodaltons. Such small organic molecules can be included as agents, etc. as defined above.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the term "about" means within 20%, preferably within 0%, and more preferably within 5%.

Nucleic Acids and Proteins

The present invention contemplates the use of the nucleic acids encoding DC-SIGN e.g., encoding the human protein having the amino acid sequence of SEQ ID NO:2) and encoding fragments thereof including chimeric/fusion proteins. In a preferred embodiment the nucleic acid encodes a soluble form/portion of DC-SIGN. Similarly, the present invention also contemplates the use of the nucleic acids encoding the translocating promoters, cyclin T (e.g., encoding the human protein having the amino acid sequence of SEQ ID NO:6) and CD4. These nucleic acids can be used for example, to make transgenic animals that contain the human homologs of such proteins, thereby making a transgenic animal susceptible to HIV infection. The use of the proteins, fragments thereof including chimeric/fusion proteins are also part of the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [.I. Freshney, ed. (1986)]; *Immobilized Cells And Enzymes* [IRL Press, (1986)]; B. Perbal, A *Practical Guide To Molecular Cloning* (1984); F. M. Ausubel et al. (eds.), Current *Protocols in Molecular Biology*, John Wiley & Sons, Inc. (1994).

Therefore, if appearing herein, the following terms shall have the definitions set out below.

A "vector" is a replicon, such as plasmid, phage, virus, or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adeno sine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the MRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5×or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 18 nucleotides; preferably at least about 36 nucleotides; and more preferably the length is at least about 48 nucleotides. Such nucleic acids can be used as primers or nucleic acid probes for the nucleic acids encoding the translocation promoting agents of the present invention.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" as used herein refers to one method of inserting a foreign DNA sequence of a vector into chromosome. The vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be secreted or expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

A "heterologous nucleotide sequence" as used herein is a nucleotide sequence that is added to the nucleotide sequence of a nucleic acid of the present invention by recombinant methods to form a nucleic acid which is not naturally formed in nature. Such nucleic acids can encode fusion (e.g. chimeric) proteins. Thus the heterologous nucleotide sequence can encode peptides and/or proteins which contain regulatory and/or structural properties. In another such embodiment the heterologous nucleotide sequence can encode a protein or peptide that functions as a means of detecting the protein or peptide encoded by the nucleotide sequence of the present invention after the recombinant nucleic acid is expressed. In still another embodiment the heterologous nucleotide sequence can function as a means of detecting a nucleotide sequence of the present invention. A heterologous nucleotide sequence can comprise non-coding sequences including restriction sites, regulatory sites, promoters and the like.

As used herein the terms "fusion protein" and "fusion peptide" are used interchangeably and encompass "chimeric proteins and/or chimeric peptides" and fusion "intein proteins/peptides". A fusion protein comprises at least a portion of a particular protein of the present invention such as DC-SIGN joined via a peptide bond to at least a portion of another protein or peptide in a chimeric fusion protein. In a particular embodiment the portion of the DC-SIGN is antigenic. For example fusion proteins can comprise a marker protein or peptide, or a protein or peptide that aids in the isolation and/or purification of DC-SIGN.

In a specific embodiment, two DNA sequences are "substantially homologous" or "substantially similar" when at least 50% (preferably at least 75%, and most preferably at least 90 to 95%) of the nucleotides match over the defined length of the DNA coding sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 75% of the amino acids are identical, or preferably greater than about 90% are identical. Preferably, the similar or homologous sequences are identified by alignment using, for example, the GCG (Genetics Computer Group, Program Manual for the GCG Package, Version 7, Madison, Wis.) pileup program using the default parameters.

The term "corresponding to" is used herein to refer similar or homologous sequences, more preferably substantially similar or substantially homologous sequences, whether the exact position is identical or different from the molecule to which the similarity or homology is measured. The term "corresponding to" refers to the sequence similarity, and not the numbering of the amino acid residues or nucleotide bases.

Expression of Nucleic Acids/Recombinant Proteins

A nucleic acid encoding DC-SIGN, or a translocation promoting agent, or CD4, or cyclin T, or antigenic fragment, derivative or analog thereof, including a chimeric protein, thereof, can be inserted into an appropriate expression vector, i.e., a vector which contains the necessary elements for the transcription and translation of the inserted protein-coding sequence. Such elements include a "promoter." Such a nucleic acid can be operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the protein and/or its flanking regions.

The present invention also relates to nucleic acids encoding analogs and derivatives of the DC-SIGN. The production and use of derivatives and analogs are within the scope of the present invention. In a specific embodiment, the derivative or analog is a soluble fragment of DC-SIGN that is capable of inhibiting the HIV gp120-DC-SIGN interaction.

Derivatives of DC-SIGN can be made by altering nucleic acids encoding DC-SIGN by substitutions, additions or deletions that provide for functionally modified molecules. Preferably, derivatives are made that interfere with HIV infection. Such derivatives may encode soluble fragments of the extracellular domain of DC-SIGN that retain an affinity for an HIV or SIV envelope protein. Such soluble derivatives may be potent inhibitors of HIV or SIV binding.

Due to the degeneracy of nucleotide coding sequences, other DNA sequences which encode substantially the same amino acid sequence as DC-SIGN may be used in the practice of the present invention. These include but are not limited to allelic genes, homologous genes from other species, and nucleotide sequences comprising all or portions of DC-SIGN which are altered by the substitution of different codons that encode the same amino acid residue within the sequence, thus producing a silent change. Likewise, DC-SIGN derivatives of the invention include, but are not limited to, those containing, as a primary amino acid sequence, all or part of the amino acid sequence of DC-SIGN including altered sequences in which functionally equivalent amino acid residues are substituted for residues within the sequence resulting in one or more conservative amino acid substitutions. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. Such substitutions are defined herein as conservative substitutions. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $NH_2$ can be maintained.

Nucleic acids encoding DC-SIGN derivatives and analogs of the invention can be produced by various methods known in the art. The manipulations which result in their production can occur at the gene or protein level. For example, the cloned DC-SIGN sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the nucleic acid encoding a derivative or analog of DC-SIGN care should be taken to ensure that the modified nucleic acid remains within the same translational reading frame uninterrupted by translational stop signals, in the region where the desired activity is encoded.

Additionally, a nucleic acid encoding DC-SIGN can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations diminish the ability of dendritic cells to transport HIV. Any technique for mutagenesis known in the art can be used, including but not limited to, in vitro site-directed mutagenesis [Hutchinson, et al., *J. Biol. Chem.* 253:6551 (1978); Zoller and Smith, *DNA* 3:479–488 (1984); Oliphant et al., *Gene* 44:177 (1986); Hutchinson et al, *Proc. Natl. Acad. Sci. U.S.A.* 83:710 (1986)], use of TAB® linkers (Pharmacia), etc. PCR techniques are preferred for site directed mutagenesis [see Higuchi, "Using PCR to Engineer DNA", in *PCR Technology: Principles and Applications for DNA Amplification*, H. Erlich, ed., Stockton Press, Chapter 6, pp. 61–70 (1989)]. The identified and isolated nucleic acid can then be inserted into an appropriate cloning vector. Any of a large number of vector-host systems known in the art may be used. Potential chimeric partners for DC-SIGN can include other transmembrane domains, or a domain for modification with a phospholipid anchor. Indeed, all of the proteins/fragments of the present invention can be modified by being placed in a fusion or chimeric peptide or protein, or labeled e.g., to have an N-terminal FLAG-tag, or H6 tag. In a particular embodiment DC-SIGN can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant protein of the present invention, or fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid is cultured in an appropriate cell culture medium under conditions that provide for expression of the protein by the cell. Any of a number of methods may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a nucleic acid of the present invention may be controlled by any promoter/enhancer element known in the art, but these regulatory elements must be functional in the host selected for expression. In one embodiment a translocation promoting agent is under the control of the CD4 enhancer/promoter/silencer, as described [Killeen et al. *EMBO* 12:1547–1553 (1993)].

A wide variety of host/expression vector combinations may be employed in expressing the DNA sequences of this invention. In addition, a host cell strain may be chosen which modulates the expression of the inserted sequences, or modifies and processes the gene product in the specific fashion desired. Different host cells have characteristic and specific mechanisms for the translational and post-translational processing and modification of proteins, e.g., glycosylation, or cleavage of a signal sequence for example. Appropriate cell lines or host systems can be chosen to ensure the desired modification and processing of the foreign protein expressed. For example, expression in a bacterial system can be used to produce an nonglycosylated core protein product. However, DC-SIGN expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, translocation promoting activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

DC-SIGN expressed as an integral membrane protein can be isolated and purified by standard methods. Generally, the integral membrane protein can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins. Soluble forms of the gp120 binding portion of DC-SIGN can also be obtained through proteolysis and/or expression of the extracellular domain minus the transmembrane domains.

A consequence of the present results is that mutations in DC-SIGN could result in either loss of binding of gp120 or in loss of a conformational change in envelope glycoprotein after binding (such that fusogenic activity of gp120 would be compromised) would protect an individual from transmission of infection or from progression to disease. Therefore, the present invention provides a test for polymorphisms in the DC-SIGN gene to predict an individual's predisposition to infection and disease progression. The polymorphisms that are protective are also part of the present invention (see PCT/US97/13946, Landau et al., where such a CCR5 variant was identified).

Therefore, the present invention includes mutations in the DC-SIGN gene that protect individuals from HIV infection as well as the means of detecting these variants. Methods of screening for such mutations can be performed either by genetic approaches or by cellular approaches. One genetic approach uses PCR-based analysis to amplify a segment of the DC-SIGN gene. The amplified nucleic acid can then be sequenced or analyzed using gel mobility (which can detect single strand conformational polymorphisms). The results obtained are then compared to the same segment from a wild-type gene. Amplification of any of the 7 coding exons and the flanking intron/exon borders, of the 5' non-coding and 3' non-coding exons of the gene encoding DC-SIGN and/or of the promoter will identify such mutant alleles.

Alternatively, a cellular approach is to obtain peripheral blood mononuclear cells from individuals. These cells are then cultured for 2–6 days in GM-CSF and IL-4 so as to differentiate into immature dendritic cells. The dendritic cells can then be (i) stained with anti-DC-SIGN antibody; (ii) stained with a combination of soluble gp120 and labeled anti-gp120 antibody or soluble CD4; and/or (iii) applied to the capture/enhancement assays described herein with reporter virus and target cells. In the first case, (i) cells that lack DC-SIGN will not stain with a detectable anti-DC-SIGN antibody, whereas, cells either lacking DC-SIGN or encoding a mutant DC-SIGN can be identified for lack of binding to gp120 (ii) or inability to capture/enhance HIV infectivity (iii).

One of the models suggested by the present results is based on the clustering of DC-SIGN being required for its activity in enhancing T cell infection. Therefore, even if the virus binds to DC-SIGN there needs to be appropriate clustering of the receptor on the surface of the dendritic cell. Selected compounds could block the clustering activity, even if binding of virus could still occur. Such compounds would therefore be agents that block infection of T cells and monocytes.

In addition, compounds can be identified that block DC-SIGN processing of HIV-1 to permit persistence of virus (protection from decay in infectivity) and presentation in trans to enhance infection of T cells. The virus is protected from proteases after interaction with dendritic cells or other cells transfected with DC-SIGN. Therefore, compounds that inhibit this protective mechanism of the virus after it binds to DC-SIGN are part of the invention. Such compounds can be identified by using the capture and trans-enhancement assays described herein, with whole cells that express DC-SIGN. With the capture assay, the screen can be for compounds that inhibit infection of target cells that are added to the DC-SIGN expressing cells one or more days after the DC-SIGN cells were pulsed with reporter virus (see the Example below).

The present invention further provides the use of soluble DC-SIGN to block infection in vivo. Certain forms of soluble DC-SIGN (e.g., modified to bind yet also prevent a conformational change) could block HIV infection while other forms could enhance fusion. Such forms of DC-SIGN can be produced by performing mutagenesis to generate DC-SIGN variants that continue to bind gp120 but fail to transmit captured virus to T cells, and/or other target cells and/or to enhance infection of T cells and other target cells in trans. One particular approach is to perform random mutagenesis of the DC-SIGN extracellular domain using standard error-prone PCR, transfect or retrovirally transduce the different mutant clones into an appropriate cell lines such as THP-1, sort for cells that bind gp120, using magnetic beads coated with anti-gp120 antibody or using AC S, and then test individual transfected clones for the ability to transmit virus to appropriate target cells expressing CD4/CCR5 or CD4/CXCR4. Mutant forms of DC-SIGN that cannot enhance entry in trans can be made into soluble or secreted forms by one of the methods described above, and these can be tested for their ability to inhibit trans-enhancement in assays such as those described herein.

Antibodies to Proteins of the Present invention

According to the invention, DC-SIGN, or a translocation promoting agent, or CD4, or cyclin T produced recombinantly or by chemical synthesis, and fragments or other derivatives or analogs thereof, including fusion proteins, may be used as an immunogen to generate antibodies that recognize the protein or a particular epitope of the protein. Such antibodies include but are not limited to polyclonal, monoclonal, chimeric, single chain, Fab fragments, and an Fab expression library. The antibodies of the invention may be cross reactive, e.g., they may recognize antigens from different species. Polyclonal antibodies have greater likelihood of cross reactivity. Alternatively, an antibody of the invention may be specific for a single form of a protein, such as the being specific for human DC-SIGN, or an epitope thereof.

In a particular embodiment, the site on gp120 that binds to DC-SIGN can be used as the basis for an immunogen to elicit antibodies that prevent binding to DC-SIGN. A vaccine that elicits mucosal antibody responses as well as generalized humoral responses against gp120 can prevent binding of HIV to DC-SIGN and, therefore, limit infection of T-cells. Antibodies that prevent HIV binding to DC-SIGN or DC-SIGN-mediated enhancement of target cell infection are therefore part of the invention. Such antibodies would preferably inhibit across viral clades and inhibit broadly within viral clades. These antibodies are in contract to antibodies that are neutralizing (i.e., inhibit infection of target cells with high concentrations of HIV) and which have not been shown to be broadly neutralizing in humans. Vaccine vectors that preferentially elicit mucosal antibody responses (e.g., recombinant salmonella vectors) would constitute one approach, particularly if the site on gp120 required for binding to DC-SIGN does not require glycosylation.

One particular approach is to deliver fragments of gp120 that contain the DC-SIGN binding site to mucosal surfaces in appropriate adjuvants. In addition, a DC-SIGN-altered form of envelope protein can be used as a candidate vaccine for eliciting humoral responses (i.e., a novel form of a fusion-competent envelope vaccine). Thus, the present invention provides a complex of DC-SIGN with monomeric gp120 or gp140 oligomers as an immunogen to elicit broadly-neutralizing antibodies that will bind to DC-SIGN-induced epitopes on the envelope glycoprotein and thus block the trans-enhancement of infection. Antibodies raised by such means are more likely to inhibit DC-SIGN-enhanced infection of target cells than DC-SIGN-independent infection.

DC-SIGN can also be used as an immunogen to elicit anti-DC-SIGN antibodies that block binding of HIV. A soluble form of DC-SIGN, which has been modified to prevent its ability to enhance viral entry (due to loss of binding to gp120 or to loss of trans-enhancement function after binding to gp120), can be used as the inununogen.

In a specific embodiment, an antibody of the invention is specific for a masked epitope on gp120 that is exposed on binding to DC-SIGN. In another embodiment, an antibody of the invention is specific for an epitope created by the binding of DC-SIGN and HIV to a translocation promoting agent and/or CD4. For example, the binding of HIV envelope protein to CD4 induces a conformational change in gp120 or gp130, which results in an increased affinity of gp120 or gp130 for the translocating promoter, and possibly a concomitant unmasking of a translocating promoter epitope. Similarly, the binding of DC-SIGN to gp120 or gp130 also has the same effect. Such antibodies can be selected on the basis of binding under conditions of HIV or SIV binding to DC-SIGN, e.g., at 4° C. to inhibit binding, and screened for non-binding to free DC-SIGN.

Various procedures known in the art may be used for the production of polyclonal antibodies to DC-SIGN for example, or derivative or analog thereof. For the production of antibody, various host animals can be immunized by injection with DC-SIGN for example, or a derivative (e.g., fragment or fusion protein) thereof, including but not limited to rabbits, mice, rats, sheep, goats, etc. In one embodiment, DC-SIGN or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward DC-SIGN for example, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A*. 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing technology described in [PCT/US90/02545]. In fact, according to the invention, techniques developed for the production of "chimeric antibodies" [Morrison et al., *J. Bacteriol*. 159:870 (1984); Neuberger et al., *Nature* 312:604–608 (1984); Takeda et al., *Nature* 314:452–454 (1985)] by splicing the genes from a mouse antibody molecule specific for DC-SIGN, for example, together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce DC-SIGN-specific single chain antibodies for example. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a translocation promoting protein, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, inununoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of DC-SIGN, for example, one may assay generated hybridomas for a product which binds to a translocation promoting agent fragment containing such epitope. For selection of an antibody specific to a DC-SIGN from a particular species of animal, one can select on the basis of positive binding with DC-SIGN expressed by or isolated from cells of that species of animal.

The foregoing antibodies can be used in methods known in the art relating to the localization and activity of DC-SIGN, e.g., for Western blotting, imaging DC-SIGN in situ, measuring levels thereof in appropriate physiological samples, etc. using any of the detection techniques mentioned above or known in the art.

Suitable labels for antibodies (as well as for the other proteins, peptides and nucleic acids of the present invention) include enzymes, fluorophores (e.g., fluorescene isothiocyanate (FITC), phycoerythrin (PE), Texas red (TR), rhodamine, free or chelated lanthanide series salts, especially $Eu^{3+}$ green fluorescent protein, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker. In the instance where a radioactive label, such as the isotopes $^{3}H$, $^{14}C$, $^{32}P$, $^{35}S$, $^{59}Fe$, $^{90}Y$, $^{125}I$, $^{131}I$, and $^{186}Re$ are used, known currently available countins procedures may be utilized. In the instance where the label is a protein, e.g., an enzyme or fluorescent protein, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al (U.S. Pat. No. 4,703,017). Other direct labels include a radionucleotide, a fluorescent moiety or a luminescent moiety including proteins comprising such moieties such as green fluorescent protein. In addition to these direct labeling devices, indirect labels comprising enzymes can also be used according to the present invention.

Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419–439, (1980) and in U.S. Pat. No. 4,857,453. Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $_{32}P$, e.g., as described in European Patent No. 0372707 (Application No. 89311108.8) by Sidney Pestka, or U.S. Pat. No. 5,459,240, issued Oct. 17, 1995 to Foxwell et al.

Proteins, including antibodies, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^{3}H$]-amino acids (with the tritium substituted at non-labile positions).

In a specific embodiment, antibodies that agonize or antagonize the activity of DC-SIGN can be generated. Such antibodies, when conjugated with a toxin or radioactive element, can be used to target HIV-facilitative cells for destruction. Thus, cells harboring HIV, particularly in its dormant phase, can be destroyed with antibodies, e.g., conjugated to a toxin such as ricin or a radioisotope such as $^{32}P$ or $^{125}I$, when such antibodies are specific for the DC-SIGN HIV gp120 complex.

Vaccination and Passive Immune Therapy

Active immunity against a virus such as HIV can be induced by immunization (vaccination) with an adjuvant and a protein of the present invention, and/or protein complex of the present invention, and/or antigenic fragment thereof, and/or derivative thereof. For example, either an immunogenic amount of a portion of gp120 that is required for binding DC-SIGN or an immunogenic amount of a portion of gp120 that is exposed upon gp120 binding of DC-SIGN due to the concomitant conformational change (herein referred to collectively as particular gp120 epitopes) can serve as the antigenic component of the vaccine.

For example,the particular gp120 epitope alone or conjugated to a capsule or capsules cannot cause AIDS, and the active immunity elicited by vaccination with the particular gp120 epitope according to the present invention can result in both an immediate immune response and in immunological memory, and thus provide long-term protection against infection by HIV, particularly when the particular gp120 epitope is a conserved region of gp120. The particular gp120 epitope, or derivatives thereof, can be prepared in an admixture with an adjuvant to prepare a vaccine. Preferably, the particular gp120 epitope or derivative or fragment thereof, used as the antigenic component of the vaccine is an antigen common to all or many strains of HIV. The antigenic component of the vaccine is therefore preferably a common antigen.

Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

An alternative to a traditional vaccine comprising an antigen and an adjuvant involves the direct in vivo introduction of DNA encoding the antigen into tissues of a subject for expression of the antigen by the cells of the subject's tissue. Such vaccines are termed herein "nucleic acid-based vaccines." The expression vector can be engineered to contain an autologous signal sequence. For example, a naked DNA vector (see, e.g., Ulmer et al., 1993, Science 259:1745–1749), a DNA vector transporter (e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990), or a viral vector containing a nucleic acid encoding a particular gp120 epitope can be injected into tissue. Suitable viral vectors include retroviruses that are packaged in cells with amphotropic host range (see Miller, 1990, Human Gene Ther. 1:5–14; Ausubel et al., *Current Protocols in Molecular Biology*, §9), and attenuated or defective DNA virus, such as but not limited to herpes simplex virus (HSV) (see, e.g., Kaplitt et al., 1991, Molec. Cell. Neurosci. 2:320–330), papillomavirus, Epstein Barr virus (EBV), adenovirus (see, e.g., Stratford-Perricaudet et al., 1992, J. Clin. Invest. 90:626–630), adeno-associated virus (AAV) (see, e.g., Samulski et al., 1987, *J. Virol.* 61:3096–3101;

Samulski et al., 1989, *J. Virol.* 63:3822–3828), and the like. Defective viruses, which entirely or almost entirely lack viral genes, are preferred. Defective virus is not infective after introduction into a cell.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.* 267:963–967 (1992); Wu and Wu, *J.h Biol. Chem.* 263:14621–14624 (1988); Hartmut et al., Canadian Patent Application No. 2,012,311, filed Mar. 15, 1990)].

Any vaccine of the invention, e.g., a vaccine comprising a particular gp120 epitope antigen or antigenic derivative or fragment thereof, or the corresponding nucleic acid vaccine, can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen.

Passive immunity can be conferred to an animal subject suspected of suffering from, or particular susceptible to a viral infection, preferably a retrovirus, and more preferably HIV infection, by administering antiserum, polyclonal antibodies, or a neutralizing monoclonal antibody against a particular gp120 epitope of the invention to the patient. Although passive immunity does not confer long term protection, it can be a valuable tool for the treatment of a subject who has not been vaccinated. Preferably, the antibodies administered for passive immune therapy are autologous antibodies. For example, if the subject is a human, preferably the antibodies are of human origin or have been "humanized, " in order to minimize the possibility of an immune response against the antibodies.

An analogous therapy to passive immunization is administration of an amount of solubilized DC-SIGN sufficient to inhibit the transport of HIV by dendritic cells to T cells. The required amount can be determined by one of ordinary skill using standard techniques.

The active or passive vaccines of the invention, or the administration of soluble DC-SIGN, can be used to protect an animal subject from viral infection, preferably retrovirus invention, and more preferably, AIDS. Thus, a vaccine of the invention can be used in birds, such as chickens, turkeys, and pets; in mammals, preferably a human, although the vaccines of the invention are contemplated for use in other mammalian species, including but not limited to domesticated animals (canine and feline); farm animals (bovine, ovine, equine, caprine, porcine, and the like); rodents; and undomesticated animals. In the case of AIDS, vaccination, of course, envisioned to be in humans.

Methods for Screening Drug Libraries for Compounds Useful in the Treatment and/or Prevention of HIV Infection The present invention includes assays that are based on trans-enhancement of viral infection. Such assays can be used to screen for compounds including antibodies that inhibit the ability of DC-SIGN to enhance infection of target cells in trans. The assays can also be developed into test kits to monitor responses for preventive or therapeutic vaccines. Such assays can utilize:

(i) any of a variety of cell lines as target cells that express CD4 and a translocation promoting agent, including but not limited to CCR5 or CXCR4;

(ii) a source of DC-SIGN, either on the surface of cells in membrane vesicles or soluble recombinant material; and (iii) a recombinant form of HIV that encodes a reporter genes; e.g., luciferase or green fluorescent protein to permit a determination of the effective infection of the target cells.

Examples of appropriate cell lines include, but are not limited to murine 3T3 cells, human HeLa, U87MG, HOS, and 293 cells that are transgenically manipulated to express CD4. Additional human cell lines that do not normally express either CXCR4 or CKR-5 (such as SCL) can also be used. Furthermore, cell lines included in the Example, below can also be used.

Cell lines transfected with DC-SIGN can be used in assays to capture gp120 or infectious HIV particles. Cells expressing DC-SIGN can be pulsed with the reporter virus, washed and incubated with the target cells. Reporter activity can then be assayed in the cultured cells. In certain assays dendritic cells can be utilized as cells that express DC-SIGN.

Cell lines transfected with DC-SIGN can be used in assays to enhance target cell infection in trans. Mixtures of cells that express DC-SIGN and target cells can be incubated with appropriate titers of reporter virus, and reporter activity will then be measured. As controls for background infection, cells that do not express DC-SIGN are used.

Membrane vesicles containing DC-SIGN can also be used with target cells to capture reporter virus or to enhance infection of target cells in trans with reporter virus. One embodiment uses lipid monolayers to anchor DC-SIGN on a solid support. Reporter virus is then added. In a particular embodiment of this type, the membranes are then washed. In either case, the target cells then added.

In another embodiment the anchored solid phase DC-SIGN is treated with soluble gp120 or gp140, washed, and then screened for antibodies that bind specifically to the DC-SIGN-gp120 or go140 complex. In a preferred embodiment of this type, the antibody does not bind to either DC-SIGN or gp120/140 alone. Antibodies identified in this matter can then be used to screen for compounds that block the binding of these antibodies to solid phase DCS/gp120 or gp140 complexes. These antibodies are also part of the invention.

Soluble or secreted forms of DC-SIGN also can be used in the capture or enhancement assays disclosed herein. These forms of DC-SIGN can be prepared in bacteria or in eukaryotic expression systems including mammalian cell lines and insect cells using recombinant baculovirus. One means of preparing these forms of DC-SIGN is to link a signal peptide sequence to an epitope tag and to the N-terminal amino acid residue of the ectodomain (most membrane-proximal) and express this in mammalian cell lines. Another approach is to make a fusion protein with DC-SIGN and an extracellular domain of a transmembrane protein; e.g., CD8-alpha, such that a protease cleavage site (e.g., recognized by thrombin) separates that domain from an epitope-tagged form of DC-SIGN ectodomain. After purification on an anti-CD8 affinity column, this protein can be cleaved with thrombin to yield the soluble forms of DC-SIGN. The resulting protein can be used as a monomer in the trans-enhancement assay or in multimeric form, possibly bound to beads or other solid support, in the capture and enhancement assays and in drug screens as described above with the membrane vesicles.

HIV and SIV vectors include, but are not limited to HIV or SIV-luciferase, HIV or SIV-alkaline phosphatase, HIV or SIV-CD24 and HIV or SIV-2 LTR-Green Fluorescent Protein. In such vectors, the env gene can be inactivated by frame shifting, and the reporter gene is then inserted to replace the Nef open reading frame. Additional vectors can be made for easier screening in murine cells, in which expression of HIV-LTR-driven reporters is only about 1% of the level in human cells. Such vectors are based on the HIV-gpt prototype, such that the reporter, e.g. luciferase is placed under control of the SV40 promoter within the env gene, ensuring high level expression following integration.

HIV-1 envelope glycoproteins whose tropism for CCRs and CXR4 that have been determined can be appropriate for screening. For example, CCR5-tropic envelope glycoproteins ADA and YU-2, (which can also use CCR3) 92US715, and 91US005 and one dual tropic for CXCR4 and CXCR5 (92HT593) are also able to infect cells tranfected with BOB. Two of the envelope proteins for primary HIV-1 strains (the dual tropic 92HT539 and CR5-tropic 92BRO25) also use Bonzo. In addition T-tropic envelope glycoproteins include HXB2, 92UG021, and 92HT599 also use BOB or Bonzo. Other CCR5-tropic envelope glycoproteins include BaL, 92UG975, 93HT966, 92RWO20, 93TH976, 92BRO20, and 93MW965. JRFL is a CCR5-tropic envelope glycoprotein that uses BOB only weakly. Envelope glycoproteins of SIV such as Mac1A11-Agm TY01, or Mac 239 can also be used to screen for receptors that are used by SIV.

Identification of Antagonists of HIV Infection

Identification of the role that DC-SIGN plays in HIV infection provides a unique set of protocols to identify specific agents that inhibit HIV infection. Accordingly, the present invention contemplates methods for identifying agonists and antagonists of HIV entry using various screening assays known in the art. In one embodiment, such agonists or antagonists competitively inhibit HIV binding, or more particularly, an HIV or SIV envelope protein binding to DC-SIGN.

In one such embodiment, cell lines expressing CD4 and one or more translocating promoters, can be infected with an HIV-reporter virus or SIV-reporter virus that is pseudotyped with one or more selected envelope glycoproteins in the presence of DC-SIGN. Compound libraries can be assayed for their ability to inhibit infection of the cells by the pseudotyped virus. Candidate compounds are selected and then can be counter-screened for non-specific effects on infection with virus pseudotyped with non-HIV or non-SIV envelope proteins such as MLV amphotropic env or with VSV-G env for example.

Any screening technique known in the art can be used to screen for antagonists of DC-SIGN-gp120 association. The present invention contemplates screens for small organic compounds, as well as screens for natural ligands that bind to and antagonize such activity in vivo. For example, natural products libraries can be screened using assays of the invention for molecules that antagonize HIV-DC-SIGN association.

Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued Dec. 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. U.S.A. 90:10700–4 (1993); Ohlmeyer et al., Proc. Natl. Acad. Sci. U.S.A. 90:10922–10926 (1993); Lam et al., International Patent Publication No. WO 92/00252; Kocis et al., International Patent Publication No. WO 9428028, each of which is incorporated herein by reference in its entirety], and the like can be used to screen for inhibitors of DC-SIGN mediated HIV entry into T cells according to the present invention.

The screening can be performed with recombinant cells that express DC-SIGN, or alternatively, using purified and preferably soluble protein, e.g. produced recombinantly, as described above. For example, the ability of a labeled, soluble or solubilized DC-SIGN that includes the gp120-binding portion of the molecule, to bind gp120 can be used to screen libraries such as random phage libraries or chemical libraries, as described herein. Any of the numerous assays well known in the art and/or exemplified herein may be used.

The present invention includes compounds that interfere with the binding of gp120 to DC-SIGN (DCS). These can be small organic compounds potentially but not exclusively based on oligosaccharide structures; or they can be antibodies specific for DC-SIGN or they could be antibodies specific for gp120, particularly conserved regions that are required for interacting with DC-SIGN. Such compounds interfere with infection, particularly with infection of cells that do not express DC-SIGN.

The present invention therefore also includes compounds that interfere with the binding of gp120 to DC-SIGN (DCS). In a particular embodiment the compound is has a structure based on that of a oligosaccharide. Alternatively, the compound can be an antibody specific for DC-SIGN or an antibody specific for particularly conserved regions of gp120 that are required for interacting with DC-SIGN. Such compounds interfere with infection, particularly with infection of cells that do not express DC-SIGN.

The present invention also provides compounds that interfere with DC-SIGN-dependent enhancement of HIV-target cell fusion. Such compounds include antibodies that bind to DC-SIGN and interfere with the trans-enhancement of HIV entry by way of CD4 and CCR5/CXCR4 on the target cell. Preferably such compounds or antibodies do not block the binding of gp120 to DC-SIGN.

Based on the results disclosed herein, it appears that interaction of gp120 with DC-SIGN results in a conformational change in envelope glycoprotein which would enhance fusogenic activity. Therefore compounds including antibodies that specifically interact with such an altered form of the envelope glycoprotein (gp120/gp41) induced by DC-SIGN binding and that, hence, block viral entry are also provided. Such small organic compounds or antibodies can be identified by screening for drugs in a trans-enhancement assay or by using complexes of DC-SIGN and gp120 or oligomers of soluble gp140. For example, soluble DC-SIGN/gp120 can be used to elicit monoclonal antibodies that will bind specifically only to a complex of these proteins or to a conformational epitope on gp120. Such complexes can also be used to screen for compounds that bind specifically to DC-SIGN/gp120 or DC-SIGN/gp140 or to the novel conformations of the envelope glycoproteins.

Administration of Antagonists of HIV Infection

According to the invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of an antagonist to the DC-SIGN -gp120 complex is administered to prevent or treat AIDS, it may be introduced by injection into the blood. The antagonist may be a specific antibody raised against a particular epitope of the DC-SIGN -gp120 complex or a mimic to DC-SIGN, including a soluble form of DC-SIGN that competitively competes with DC-SIGN for the gp120.

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing an antagonist to DC-SIGN- gp120 binding.

In yet another embodiment, the therapeutic compound can be delivered in a controlled release system. For example, an antibody as described above, may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of a therapeutic target, e.g., the brain, thus requiring only a fraction of the systemic dose [see, e.g., Goodson, in *Medical Applications of Controlled Release*, supra, vol. 2, pp. 115–138 (1984)].

Other controlled release systems are discussed in the review by Langer [*Science* 249:1527–1533 (1990)].

Thus, the antagonist can be delivered by intravenous, intraarterial, intraperitoneal, intramuscular, or subcutaneous routes of administration. Alternatively, the antagonist, properly formulated, can be administered by nasal or oral administration. A constant supply of the antagonist can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of the antagonist is an effective therapeutic regiment for AIDS is preferably a human, but can be a primate with a related viral condition. Thus, as can be readily appreciated by one of ordinary skill in the art, the methods and pharmaceutical compositions of the present invention are particularly suited to administration to any primate.

Transgenic Vectors and Inhibition of Expression

In one embodiment, a gene encoding a soluble DC-SIGN, or antisense or ribozyme specific for DC-SIGN mRNA (termed herein an "antigene") is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus macrophage can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

In another embodiment the gene or antigene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 10 5,124,263; International Patent Publication No. WO 95/07358, published Mar. 16, 1995, by Dougherty et al.; and Kuo et al., 1993, Blood 82:845.

In one embodiment, specific PBMCs are removed from an HIV-positive subject animal (e.g., a human) and the gene encoding DC-SIGN, for example, is replaced by a modified DC-SIGN gene that retains its natural activity, binds ICAM-3 but cannot facilitate the entry of HIV into T cells. The subject animal is depleted of its corresponding PBMCs (e.g., if the gene modification was performed in a macrophage or T-cell, then the macrophages or T-cell are depleted) and the modified PBMCs are reintroduced into the subject animal. Such an animal subject should then have macrophages or T-cells, which are capable of responding to the appropriate natural ligand for DC-SIGN, but which are no longer capable of facilitating the entry of HIV into a cell. In a related embodiment, a translocation promoting agent gene (such as CC-CKR5 or CXCR4) is also modified to more fully block HIV translocation/infection.

Targeted gene delivery is described in International Patent Publication WO 95/28494, published Oct. 1995.

Alternatively, the vector can be introduced in vivo by lipofection [Felgner, et. al., *Proc. Natl. Acad. Sci. U.S.A.*

84:7413–7417 (1987); see Mackey, et al., *Proc. Natl. Acad. Sci. U.S.A.* 85:8027–8031 (1988); Felgner and Ringold, *Science* 337:387–388 (1989)]. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

As noted above, the present invention extends to the preparation of antisense nucleotides and ribozymes that may be used to interfere with the expression of DC-SIGN at the translational level. This approach utilizes antisense nucleic acid and ribozymes to block translation of a specific mRNA, either by masking that mRNA with an antisense nucleic acid or cleaving it with a ribozyme. Such antisense or ribozyme nucleic acids may be produced chemically, or may be expressed from an "antigen."

Antisense nucleic acids are DNA or RNA molecules that are complementary to at least a portion of a specific mRNA molecule [see Marcus-Sekura, *Anal. Biochem.* 172:298 (1988)]. In the cell, they hybridize to that mRNA, forming a double stranded molecule. The cell does not translate an mRNA in this double-stranded form. Therefore, antisense nucleic acids interfere with the expression of MRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., *J. Exp. Med.* 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.* 260:3030 (1988)]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding the DC-SIGN can be used to prepare antisense molecules against and ribozymes that cleave mRNAs encoding DC-SIGN, thus inhibiting expression of the gene encoding the DC-SIGN, which can reduce the level of HIV entry in macrophages and T cells.

Cells on Solid Supports

Solid supports include glass beads, sugar beads (SEPHADEX, SEPHAROSE, Agarose, SEPHACEL etc.) magnetic beads, and dowex-type materials. Biological materials may be passed through cells bound to solid supports by common methods know to any person skilled in the art including but not limited by batchwise, by centrifugation, pressure-membrane filtration (e.g. Amicon or Millipore filtration) and through various types of columns.

Transgenic Animals

T lymphocytes from mice transgenic for human CD4 and CCR5 can be infected in vitro with various strains of HIV but are not infected when virus is injected into the animals. The expression of human DC-SIGN in the murine dendritic cells permits mucosal uptake of virus by these cells, transport of virus to lymphatic organs and subsequent in vivo infection of the cells that express human CD4 and CCR5.

The transgenic mice of the present application can be produced as detailed previously [Killeen et al. *EMBO* 12:1547–1553 (1993)], which is hereby incorporated by reference. The construction of the human $CD4^+$ murine CD4− mice have been described [Killeen et al. *EMBO* 12:1547–1553 (1993)].

Generation of transgenic mice thus serve as a model system for HIV pathogenesis for development of vaccines and new therapeutics. Such mice express various combinations of human CD4 (SEQ ID NO:3), CCR5 (SEQ ID NO:5) or CXCR4 (SEQ ID NO:4) and cyclin T [SEQ ID NO:6; GenBank accession AF045161, Wei et al., *Cell*, 92(4) :452–462 (1998)] in all of their T cells, subsets of T cells and/or macrophages and monocytes. These types of animals have been generated using the CD4 regulatory sequences to direct expression in these types of cells. In addition, the mice express human DC-SIGN on the surface of their dendritic cells. This can be achieved by using a CD11c promoter to direct expression in this subset of cells [Dziennis et al, *Blood*, 85(2):310–329 (1995)]. Another approach is to use homologous recombination to introduce the DC-SIGN cDNA into the site for the murine CX3CR1 coding region. The latter gene is expressed in dendritic cells, which allows for specific expression in dendritic cells of genes targeted to this site. A third method to achieve specific expression of human DC-SIGN in dendritic cells is to use homologous recombination to replace the murine DC-SIGN gene with human DC-SIGN cDNA; a similar approach has been used to replace murine CXCR4 with the human CXCR4. Another method is to use the human DC-SIGN promoter consisting 30 of sequences of up to 5 kb 5' to the first exon to drive expression in dendritic cells. This promoter is generated by cloning the sequence 5' to "GAGTTCTGGACACTGGGG-GAGAGTGGGGTGACAT" (SEQ ID NO:13).

Additional Uses of the Invention

Since the present disclosure demonstrates that DC-SIGN binds gp120 with a high affinity and thereby HIV tightly, there are multiple ancillary uses provided by the present invention. For example, DC-SIGN or gp120 binding fragment thereof, either alone, on a solid support or in the membrane of a cell can be used to bind HIV and similar viruses. Such binding can be used with electroporesis for example to filter blood products. Alternatively, a DC-SIGN derived product, as enumerated above, could be used in a vaginal prophylactic cream to prevent the transmission of virions, including HIV.

In addition, since DC-SIGN expressing cells are shown herein to not only facilitate viral transport to T cells but to also extend the longevity of virions, cells expressing DC-SIGN can be used in conjunction with viral vectors such as retroviral vectors (e.g., HIV) to enhance the effect of viral vectors during gene therapy, particularly in protocols in which the gene transfer is to be performed in T cells.

Indeed, the present invention relates to the discovery that DC-SIGN binds and captures HIV virus, particularly through interaction or binding with the HIV gp120 in trans. This unique ability to capture HIV, particularly infectious HIV, and sequester the virus in vivo or in vitro can be utilized in a variety of methods, applications and uses wherein capture of HIV is relevant or required. It is therefore contemplated that DC-SIGN can be utilized to capture HIV viruses from a patient or in a patient sample. This could effectively concentrate virus for the purpose of further study, including but not limited to: evaluation of the infectivity of the isolated HIV; assessment of the drug sensitivity of the isolated HIV; analysis of the DNA sequence of the isolated HIV, specific HIV genes or encoded polypeptide to determine or assess, for instance genetic drift and viral mutations; and other characterization of the HIV population in a patient. In addition, the DC-SIGN mediated capture methods can be utilized in purifying or removing HIV which is presumed or possibly present in a sample, particulary wherein such sample comprises a biologic/therapeutic material or compound or will be utilized in the preparation or isolation of a biologic/therapeutic material or compound. Biological/therapeutic materials or compounds isolated or purified from blood or blood components are a particular example, including Factor VIII, other coagulation factors, and blood cell components, wherein presumed or possible HIV, or other such blood-borne viruses must be removed or inactivated.

The DC-SIGN-mediated trans capture of HIV can be accomplished by providing DC-SIGN in trans in any form, medium or source wherein DC-SIGN is capable of binding to HIV to form a DC-SIGN-HIV complex or association and wherein the DC-SIGN-HIV complex or association can thereby be isolated or captures. For instance, any of the following sources of DC-SIGN can be utilized, including cells or cell lines expressing DC-SIGN, DC-SIGN in membrane vescicles or synthetic lipid or lipophilic carriers, soluble DC-SIGN, and DC-SIGN attached to a surface, separation material or medium (including for instance resins, beads and columns) directly or using lipid monolayers or lipid moieties to anchor DC-SIGN.

Isolation of Peptides Mimicking Carbohydrate

A major obstacle in the investigation of biological functions of carbohydrates is the availability of these compounds. They can often be isolated from biological sources in only minute amounts. A possible solution to this problem, is to mimic the carbohydrate by other compounds that are easier to prepare, e.g. peptides. A promising way to find such peptides is by use of the random peptide phage display technology. Peptides which mimic the DC-SIGN lectin ligand or otherwise block DC-SIGN-mediated interactions or binding may be useful in the HIV prophylaxis, prevention or therapy. Peptide ligands identified by phage display screening frequently interact with natural binding site(s) on the target molecule, and often resemble the target's natural ligand(s). Peptides mimicking carbohydrate epitopes or ligands have been isolated and work directed towards using peptide mimics in place of carbohydrate antigens has been reviewed by Kieber-Emmons and colleagues [Kieber-Emmons. et al *Immunologic Res* 17:95–108 (1998)]. The demonstrated ability of a peptide to mimic a carbohydrate determinant indicates that, although mimicry is accomplished using amino acids in place of sugars, the specificity pattern can be reproduced.

Screening phage-displayed random peptide libraries offers a rich source of molecular diversity and represents a powerful means of identifying peptide ligands that bind a receptor molecule of interest (Cwirla et al. *PNAS* 86:637–682 (1990); Devlin et al. *Science* 249:404–406 (1990); Cortese et al. *Current Opin Biotech* 6:73–80 (1995)]. Phage expressing binding peptides are selected by affinity purification with the target of interest. Since each infectious phage encodes the random sequence expressed on its surface, a particular phage, when recovered from an affinity matrix, can be amplified by another round of infection. Thus, selector molecules immobilized on a solid support or other capture means can be used to select peptides that bind to them. With regard to the present invention, DC-SIGN or gp120 may be utilized as a selector molecule in such systems. This procedure reveals a number of peptides that bind to the selector and that often display a common consensus amino acid sequence. Biological amplification of selected library members and sequencing allows the determination of the primary structure of the peptide(s).

Peptides that mimic glycosphingolipids have been found using a phage peptide library. Two monoclonal antibodies that recognize lactotetraosylceramide (Lc4Cer) and its isomer neolactotetraosylceramide (nLc4Cer) were used to find peptides that mimic the carbohydrate moieties of the two glycosphingolipids. It was also shown that the peptides are biologically active, in that they could modulate the activity of β-galactosidase [Taki et al. *FEBS Lett* 418:219–223 (1997)]. The cell wall of the bacterial pathogen Shigellaflexneri contains repeated saccharide units forming the O-antigen carbohydrate moiety of the capsular lipopolysaccharide. Peptide mimics of the carbohydrate epitope were isolated using phage display technology and could act as immunogenic mimics and were capable of inducing specific anti-carbohydrate antibodies [Phalipon et al. Eur *J Immunol* 27:2620–2625 (1997)]. Peptides that mimic HIV-associated carbohydrate forms have also been reported. Mouse antisera were generated against peptides that mimic a mucin-related carbohydrate epitope expressed on HIV. The authors showed that immunization with the peptide-mimics induces antibodies that cross-reacted with native HIV envelope proteins. The sera containing these antibodies could neutralise HIV-1 cell-free infection in vitro as well as the sera from patients infected with HIV-1 whereas normal human sera were ineffective in this viral neutralisation assay [Agadjanyan et al. *Nature Biotech* 15:547–551 (1997)]. Further such studies include: (a) a peptide mimic of a carbohydrate epitope of the Lewis Y antigen has been reported and contains the residues PWLY, which were shown to be critical for peptide binding to an antibody specific for the Lewis Y antigen [Hoess et al. *Gene* 128:43–49 (1993)]; (b) peptides that mimic the capsular polysaccharide of *Neisseria meningitidis* serogroup C generated an immune response that was able to protect mice against infection with a lethal dose of the encapsulated bacteria [Westerink et al. (1995) *PNAS* 92); and (c) the carbohydrate binding site of the lectin concanavalin A was investigated and peptides that mimic the binding of methyl α-D-mannopyranoside to ConA were identified by screening a phage-displayed random hexa- or decapeptide library [Scott et al. *PNAS* 89:5398–402 (1992); Oldenburg et al. *PNAS* 89:5393–97 (1992)].

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

DC-SIGN A DENDRITIC CELL-SPECIFIC HIV-1 BINDING PROTEIN ENHANCES TRANS-INFECTION OF T CELLS

Introduction

Dendritic cells (DC) capture microorganisms that enter peripheral mucosal tissues and then migrate to secondary lymphoid organs, where they present these in antigenic form to resting T cells and thus initiate adaptive immune responses. The mechanism by which DC capture HIV-1 and promote infection of CD4+ T cells has not been elucidated, and it has been unclear whether there is specificity in the interaction of DC with virus. Indeed heretofore, no specific dendritic cell receptor had been identified that was involved in HIV infection of T cells.

Methods

Antibodies: The antibodies (mAb) used are 2D7 (anti-CCR5; Becton and Dickinson & Co., Oxnard, Calif.) and anti-CD4 (RPA-T4; PharMingen, San Diego, Calif.). Anti-DC-SIGN mAb AZN-D1 and AZN-D2 were obtained by screening hybridoma supernatants of human DC-immunized BALB/c mice for the ability to block adhesion of DC to ICAM-3, as measured by the fluorescent bead adhesion assay.

Cells: Immature dendritic cells (DC) were cultured from monocytes in the presence of IL4 and GM-CSF (500 and 1000 U/ml, respectively; Schering-Plough, Brussels, Belgium) [Sallusto and Lanzavecchia, *J. Exp. Med.*, 179:1109–1118 (1994) and Romani et al. *J. Exp. Med.*, 180:83–93 (1994)]. At day 7 the phenotype of the cultured DC was confirmed by flowcytometric analysis. The DC express high levels of MHC class I and II, αMβ2 (CD11b), αXβ2 (CD11c) and ICAM-1, moderate levels of LFA-1 and CD80, and low levels of CD14. Stable K562 transfectants expressing ICAM-3 (K562-ICAM-3) were generated by co-transfection of K562 with 10 μg PCRII ICAM-3 plasmid and 2 μg PGK-hyg vector [te Riele et al., *Nature* 348:649–651 (1990)] by electroporation as described [Lub et al., *Mol. Biol. Cell*, 8:719–728 (1997)]. Stable TBP-1 transfectants expressing DC-SIGN were generated by transfection of TIP-1 cells with pRc/CMV-DC-SIGN by electroporation similarly as described above for K562-ICAM-3.

Isolation and expression of the cDNA encoding DC-SIGN: Immunoprecipitated DC-SIGN was identified by peptide sequencing. Tryptic digestion, purification of the resulting peptides and sequence analysis was performed by Eurosequence BV (Groningen, The Netherlands). The cDNA encoding the placenta gp120 binding C-type lectin was amplified by RT-PCR on total RNA from DC. PCR primers were based on the nucleotide sequence of the placenta gp120 binding C-type lectin [accession no. M98457, Curtis et al., *Proc. Natl. Acad. Sci. U.S.A.*, 89:8456–8360 (1992)] and the nucleotide sequences (5' to 3') are as follows:

```
XF29:    AGAGTGGGGTGACATGAGTG    (SEQ ID NO:11)
XR1265:  GAAGTTCTGCTACGCAGGAG    (SEQ ID NO;12)
```

The nucleotide sequence of the cloned cDNA was identical to that of the placenta gp120 C-type [Curtis et al., *Proc. Natl. Acad. Sci. U.S.A.*, 89:8456–8360 (1992)]. The cDNA was subsequently cloned into the eukaryotic expression vector pRc/CMV (pRc/CMV-DC-SIGN). Stable THP-1 transfectants expressing DC-SIGN were generated by transfection of THP-1 cells with pRc/CMV pRc/CMV-DC-SIGN by electroporation similarly as described above for K562-ICAM-3.

Fluorescent bead adhesion assay: Carboxylate-modified TransFluorSpheres (488/645 mn, 1.0 μm; Molecular Probes, Eugene, OR) were coated with either ICAM-3-Fc or M-tropic HIV-1$_{MN}$ envelope glycoprotein gp120 by standard methodology [Geijtenbeek et al, *Blood*, 94(2):754–64 (1999)]. The fluorescent beads adhesion assay was performed as described by Geijtenbeek et al. [*Blood*, 94(2):754–64 (1999)]. Briefly, cells were resuspended in adhesion buffer (20 mM Tris-HCl pH 8.0, 150 mM NaCl, 1 mM CaCl$_2$, 2 mM MgCl$_2$, 0.5% BSA) at a final concentration of 5×10$^6$ cells/ml. 50,000 cells were pre-incubated with mAb (20 μg/ml) for 10 min at room temperature (RT). Ligand-coated fluorescent beads (20 beads/cell) were added and the suspension was incubated for 30 min at 37° C. Adhesion was determined by measuring the percentage of cells, which have bound fluorescent beads, by flowcytometry using the FACScan (Becton and Dickinson & Co., Oxnard, Calif.). For the M-tropic HIV-1$_{MN}$ envelope glycoprotein gp120 beads, streptavidin was covalently coupled to the TransFluorSpheres as described previously [Geijtenbeek et al., *Blood*, 94(2):754–64 (1999)]. Streptavidin-coated beads were incubated with biotinylated F(ab')2 fragment rabbit anti-sheep IgG (6 μg/ml; Jackson Immunoresearch) followed by an overnight incubation with sheep-anti-gp120 antibody D7324 (Aalto Bio Reagents Ltd, Dublin, Ireland) at 4° C. The beads were washed and incubated with 250 μg/ml purified HIV-1 gp120 (provided by Immunodiagnostics, Inc through the NIH AIDS Research and Reference Reagent Program) overnight at 4° C. The fluorescent beads adhesion assay was again performed as described by Geijtenbeek et al. [*Blood*, 94(2):754–64 (1999)].

Heterotypic cell clustering and DC-induced T cell proliferation: DC and ICAM-3 expressing cells (2×10$^6$ cells/ml) were labeled respectively with sulfluorescein (Molecular Probes; 50 μg/ml) and hydroethidine (Molecular Probes; 40 μg/ml) for 1 hour at 37° C. DC and the ICAM-3 expressing cells were mixed (50×10$^3$ cells each) and incubated at 37° C. At different time points the cells were fixed with paraformaldehyde (0.5%) and heterotypic cell clustering was measured by flowcytometry. Clustering between DC with resting T cells was assessed by a different method. DC (50×10$^3$ cells) were pre-incubated with/without the anti-DC-SIGN mAb AZN-D1 and AZN-D2 (10 μg/ml) for 10 min. at RT. Allogeneic PBL (1×10$^6$cells), labeled with the fluorescent dye Calcein-A (Molecular Probes; 25 μg/10$^6$ cells/ml for 30 min. at 37°), were added and the cell mixture was incubated at 37° C. The clustering was determined by measuring percentage of DC which have bound fluorescent T cells by flowcytometry. Allogeneic responder T-lymphocytes (100× 10³) were added to DC (1.5×10³) in the presence of blocking mAb (20 µg/ml). The cells were cultured for 4 days. On day 4 the cells were pulsed for 16h with [³H]methyl-thymidine 1.52 TBq/mmol, 0.5 µCi/well; Amersham) and thymidine incorporation was quantified.

HIV-1 infection of both DC and DC-SIGN transfectants: The M-tropic strain HIV-1$_{Ba-L}$ was grown to high titer in monocyte-derived macrophages (MDM). Seven days after titration of the virus stock on MDM, TCID$_{50}$ was determined with a p24 antigen ELISA (Diagnostics Pasteur, Marnes la Coquette, France) and estimated as 10⁴/ml. DC (50×10³), pre-incubated with mAb against DC-SIGN (AZN-D1 and AZN-D2) or CD4 (RPA-T4) (20 µg/ml) or a combination of CCR5 specific chemokines (RANTES, MIP-1α, MIP-1β; each 500 ng/ml) for 20 min. at RT, were pulsed for 2 hours with HIV-1$_{Ba-L}$ (at a multiplicity of infection of 10³ infectious units per 10⁵ cells), washed and co-cultured with activated PBMC 50×10³). No DC-T cell syncytium formation was observed. The post-infection experiment was performed similarly except that the mAb or chemokines were added after the washing step of the HIV-1 pulse, together with the activated PBMC. Culture supernatants were collected at day 5, 6, 7, and 9 after DC-T cell co-culture and p24 antigen levels, as a measure of HIV-1 production were determined by a p24 antigen ELISA. P BMC were activated by culturing them in the presence of IL-2 (10 U/ml) and PHA (10 (g/ml) for 2 days. Pseudotyped viral stocks were generated by calcium-phosphate transfections of 293T cells with the proviral plasmid pNL-Luc-E⁻R⁻ (containing a luciferase reporter gene) or the proviral pHIV-eGFP (containing a GEP reporter gene) and expression plasmids for ADA, JRFL and JRCSF gp 160 envelopes. Th e isolation, identification and construction of th e plasmids encoding the primary virus envelopes from 92US715.6, 92DR020.4 and 93TH966.8 has been previously described [Bjorndal et al., *J. Virol.*, 71(10):7478–87 (1997)]. Viral stocks were evaluated by limiting dilution on 293T-CD4-CCR5 cells. HIV-1 pseudotyped with murine leukemia virus (MLV) amphotropic Env and vesicular stomatitis virus glycoprotein (VSV-G) were used to ensure target cell viability.

Immunohistochemical analysis: Cryosections (8 µm) of the tissues were fixed in 100% acetone (10 min), washed with PBS and incubated with the first antibody (10 µg/ml) for 60 min at 37° C. After washing, the final staining was performed with the ABC-AP Vectastain kit (Vector Laboratories, Burlingame, Calif.) according to the manufacturer's protocol. Nuclear staining was performed with hematoxylin.

Results

A screen for molecules that bind to the adhesion molecule ICAM-3, which is expressed constitutively on T lymphocytes, was performed. A dendritic cell-specific C-type lectin that binds with high affinity to ICAM-3 was identified and designated DC-SIGN. Monoclonal antibodies were prepared against dendritic cell surface molecules that blocked binding of ICAM-3 to the dendritic cells (DC). One such antibody was used to purify DC-SIGN and then clone the cDNA. Nucleotide sequence analysis of the cDNA indicated that this molecule is identical to a previously-described HIV-1 gp120-binding C-type lectin that was identified in a screen of a placental cDNA library for HIV gp120-binding cell surface proteins. [Curtis et al., *Proc. Natl. Acad. Sci. U.S.A.*, 89:8456–8360 (1992); International Publication, WO 93/01820] which had a nucleotide sequence of SEQ ID NO:1, and an amino acid sequence of SEQ ID NO:2. A splice variant of this protein has been reported by others that has the nucleotide sequence of SEQ ID NO: 16, and an amino acid sequence of SEQ ID NO:17.

Figures 1C, 1D:
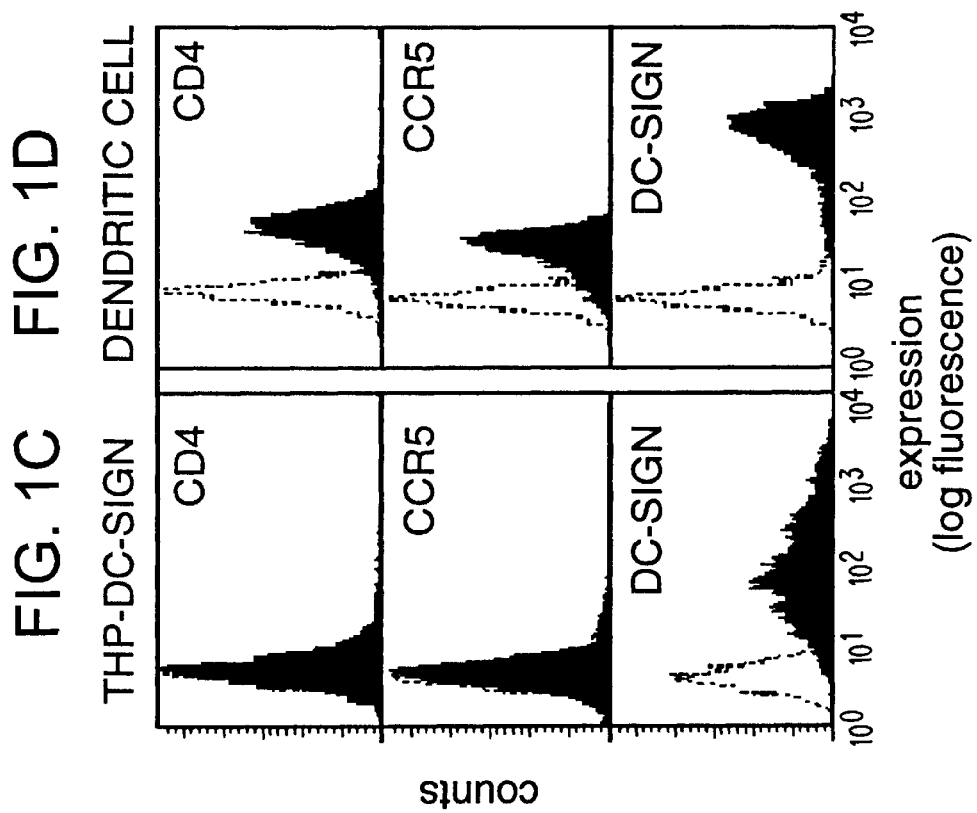

DC-SIGN is a DC-specific HIV-1 bindingprotein: DC-SIGN is now identified as a dendritic cell-specific ICAM-3 adhesion receptor that mediates dendritic cell (DC)-T cell interactions. Flow cytometric analysis of an extensive panel of hematopoietic cells with anti-DC-SIGN antibodies demonstrates that DC-SIGN is preferentially expressed on in vitro cultured DC but not on other leukocytes such as monocytes and peripheral blood lymphocytes (PBL) (FIG. 1A, Table 1). Identification of DC-SIGN by peptide amino acid sequencing of the 44 kD immunopre-cipitated protein revealed it to be 100% identical in its amino acid sequence to the HIV-1 envelope glycoprotein gp120-binding C-type lectin previously isolated from a placental cDNA library [Curtis et al, *Proc. Natl. Acad. Sci. U.S.A.*, 89:8356–8360 (1992), SEQ ID NO:2]. To determine whether this molecule has a role in binding of HIV to DC, a flow cytometric adhesion assay was used [Geijtenbeek et al., *Blood*, 94(2):754–64 (1999)] to examine the ability of HIV-1 gp120-coated fluorescent beads to bind to immature DC (FIG. 1B). The gp120-coated beads bound efficiently to the DC, and the binding was completely blocked by the anti-DC-SIGN antibodies AZN-D1 and AZN-D2. In contrast, neutralizing anti-CD4 antibodies had no effect on gp120 binding to DC. This result indicates that, although the primary HIV-1 receptor CD4 is expressed on DC (FIGS. 1C–1D), HIV-1 gp120 preferentially binds to DC-SIGN. Similarly, the monocytic cell line THP-1, which lacks expression of both CD4 and CCR5, bound the gp120-coated beads after it was transfected with a DC-SIGN expression vector (FIG. 1C).

TABLE 1

Expression level of DC-SIGN on hematopoietic cells as determined by flowcytometric analyses and RT-PCR.

| Cell-type | DC-SIGN expression* | DC-SIGN mRNA** |
|---|---|---|
| monocytes | ≤15 | − |
| immature DC day 7 | 980 | + |
| mature DC day 9‡ | | |
| LPS | 489 | + |
| MCM/PGE2 | 445 | + |
| TNFα | 420 | + |
| PBL | ≤15 | − |
| T cells | ≤15 | − |
| B cells | ≤15 | − |
| thymocytes | ≤15 | − |
| granulocytes | ≤15 | − |
| CD34+ cells | ≤15 | n.d. |
| PBMC (activated#) | ≤15 | − |
| T cell lines† | ≤15 | − |
| monocytic cell lines†† | ≤15 | − |

*mean fluorescence of staining with AZN-D1
**RT-PCR with the DC-SIGN-specific primers XF29 and XR1265 on total RNA isolated from the different cells
‡immature DC were maturated With GM-CSF, IL-4 and either TNFα, LPS or a combination of MCM and prostaglandin E2.
activated with PHA (10 µg/ml) and IL-2 (10 U/ml) for 2 days
†T cell lines: HSB, PEER, CEM and Jurkat
††monocytic cell lines: THP-1, MM6 and U937
n.d., not determined HIV-1 gp120 binding to this cell line, THP-DC-SIGN, was also blocked by anti-DC-SIGN antibodies, but not by anti-CD4 (FIG. 1E). Binding of HIV-1 gp120 to DC-SIGN expressed on DC or THP-DC-SIGN was also inhibited by the carbohydrate mannan or EGTA, consistent with previous findings [Curtis et al., *Proc. Natl. Acad. Sci. U.S.A.*, 89:8356–8360 (1992)] and with the observation that DC-SIGN is homologous to other members of the $Ca^{2+}$ binding mannose-type lectins [Weis et al., *Immunol. Rev.*, 163:19–34 (1998)]. Together, these results demonstrate that DC-SIGN is a specific dendritic cell surface receptor for the HIV-1 envelope glycoprotein.

Figure 2A:
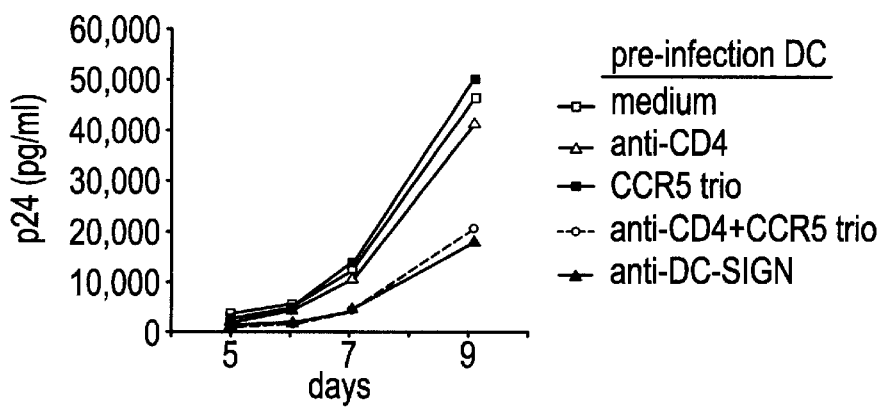
FIGS. 2A–2C show that DC-SIGN mediates HIV-1 infection in a DC-T cell co-culture.
Figure 2B:
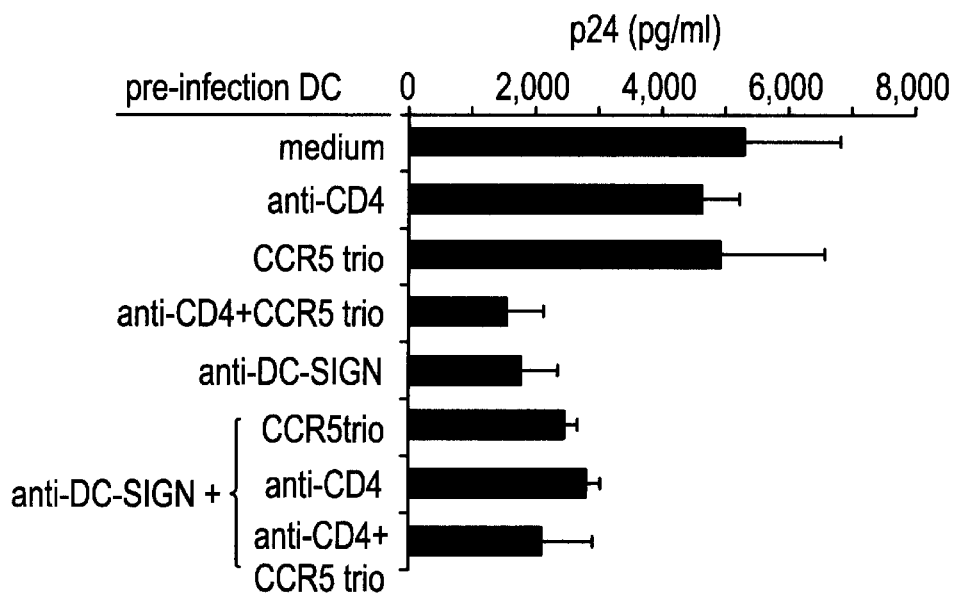

DC-SIGN is required for efficient HIV-1 infection in DC-T cell co-cultures: Because DC-SIGN is exclusively expressed on DC and has high affinity for HIV-1 gp120, it appeared reasonable to assume that it could play an important role in HIV-1 infection of DC or of T cells that make contact with DC. Immature DC, which express low levels of CD4 and CCR5 and abundant DC-SIGN (FIGS. 1C–1D), were pulsed with the R5 isolate $HIV1_{BA-L}$ for 2 hours, washed and cultured in the presence of activated T cells (FIGS. 2A and 2B). To determine the contribution of each of these receptors in this assay system, the effects of antibodies against CD4 and DC-SIGN and of a combination of three CCR5-specific chemokines (RANTES, MIP-1α and MIP-1) were examined. Pre-incubation of the immature DC with antibodies against DC-SIGN prior to infection resulted in significant inhibition of HIV-1 replication (FIG. 2A). Neither anti-CD4 nor the CCR5-specific chemokines inhibited on their own, although a combination of these did block infection of DC as efficiently as anti-DC-SIGN antibodies (FIG. 2A). Activated T cells challenged with the same viral load exhibited a weaker infection than those cultured with virus-pulsed DC.

Figure 2C:
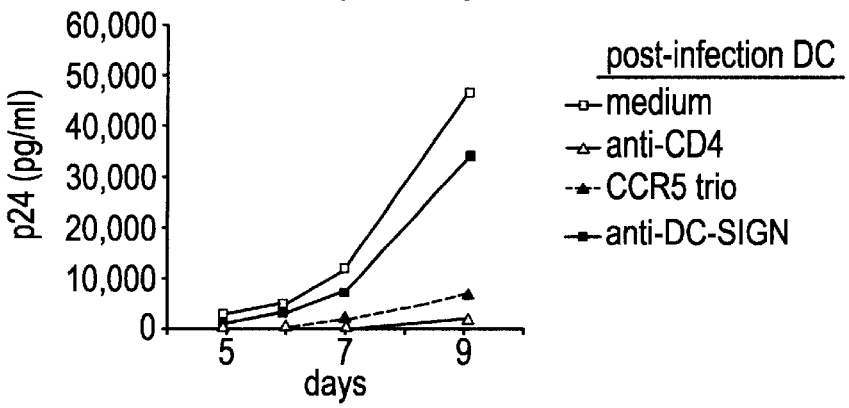

Since DC-SIGN binds to ICAM-3 on T cells, it is possible that antibodies against DC-SIGN could interfere with the DC-T cell interaction and thereby prevent HIV-1 transmission. To examine this possibility, antibodies agnst DC-SIGN were added after exposure of DC to HIV-1, but prior to the addition of activated T cells. In this setting, only CCR5-specific chemokines and anti-CD4 antibody strongly inhibited HIV-1 infection of T cells, while antibodies against DC-SIGN had no effect (FIG. 2C). These results thus suggest that DC-SIGN has an important function in propagation of HIV-1 in DC-T cell co-cultures and that this function is related to the ability of DC-SIGN to bind to gp120 and not to its interaction with ICAM-3.

Figure 3A:
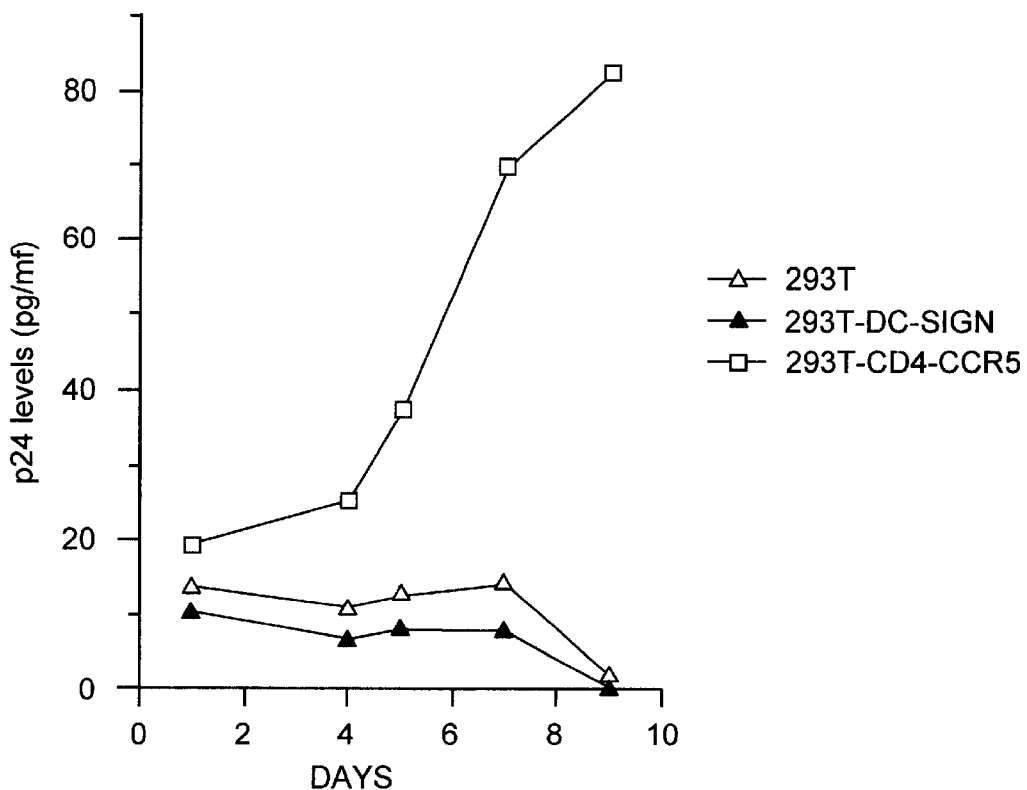
FIGS. 3A–3B show that DC-SIGN expressed on target cells does not mediate HIV-1 entry.

DC-SIGN does not mediate HIV-1 entry: To investigate whether DC-SIGN acts as a receptor that permits HIV-1 entry, similar to CD4 plus CCR5, HIV-1 entry into 293T cells that expressed either DC-SIGN (293T-DC-SIGN) or CD4 and CCR5 (293T-CD4-CCR5) was examined. Cells were pulsed overnight with $HIV_{BA-L}$, washed the next day, and p24 levels were determined. There was no detectable p24 protein in the culture supernatants harvested from 293-DC-SIGN cells several days after the HIV-1 pulse, whereas the 293T-CD4-CCR5 cells were readily infected (FIG. 3A).

Figure 3B:
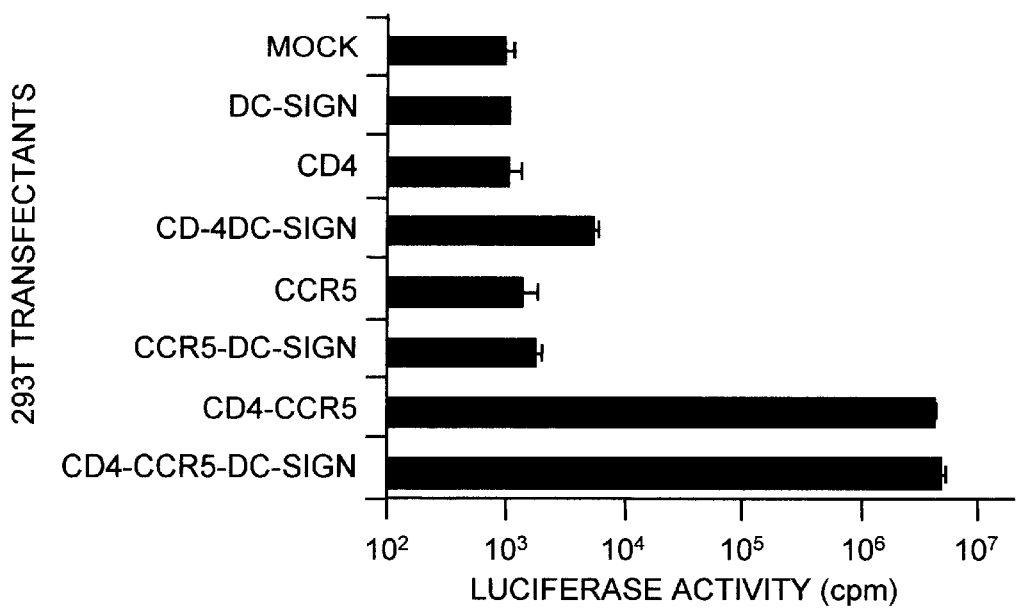

To examine the possibility that DC-SIGN may work in conjunction with either CD4 or CCR5 to permit viral entry, the studies were extended by using HIV-1 pseudotyped with the envelope glycoprotein of the R5 isolate $HIV-1_{ADA}$. A replication-defective HIV-1 genome that encoded a luciferase reporter gene was employed which allows a quantitative measure of the levels of single-round infection (FIG. 3B) [Deng et al., *Nature*, 381(6584):661–666. Transiently transfected 293T cells expressing either CCR5 (293T-CCR5), CD4 (293T-CD4), or both (293T-CD4-CCR5), in the presence or absence of DC-SIGN, were infected with the reporter virus, and luciferase levels were determined after two days. As observed with replicating virus, HIV-1 entry was not detected in 293T cells that expressed only DC-SIGN (FIG. 3B). No infection was observed if DC-SIGN was expressed with either CD4 or CCR5, indicating that DC-SIGN does not form a complex with these molecules to permit viral entry. In contrast, high luciferase activity was obtained after infection of 293T cells expressing both CD4 and CCR5, and expression of DC-SIGN did not contribute further to viral entry into these cells (FIG. 3B). Therefore, DC-SIGN cannot substitute for CD4 or CCR5 in the process of HIV-1 entry.

Figure 4A:
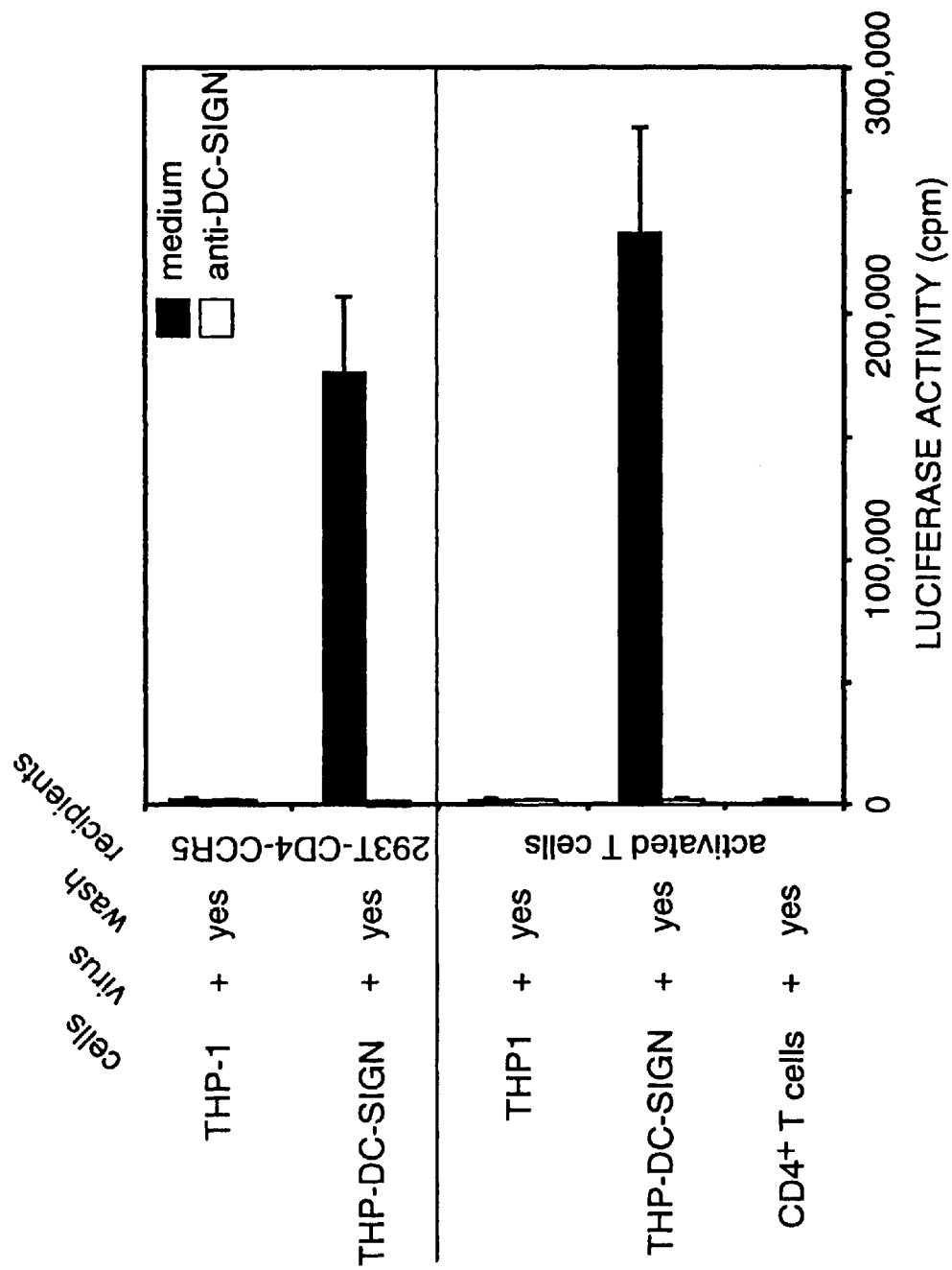
FIGS. 4A–4C show that DC-SIGN captures HIV-1 that retains infectivity for CD4+ T cells.
Figure 4B:
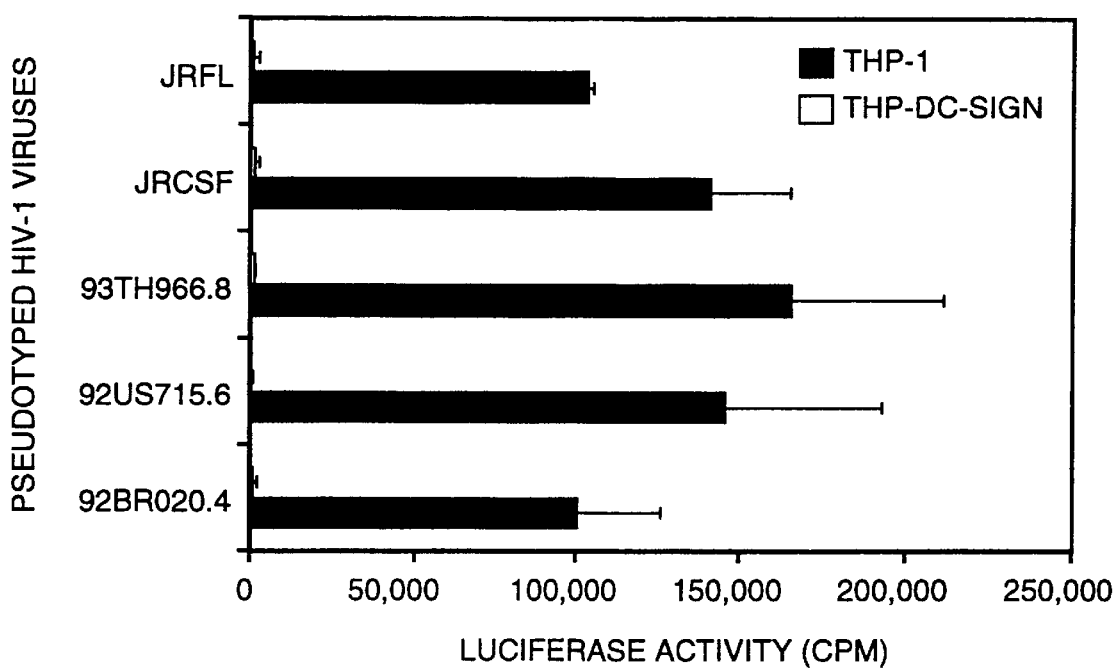

DC-SIGN captures HIV-1 and facilitates infection of HIV-1 permissive cells in trans: Because DC-SIGN did not appear to mediate virus entry into target cells, it seemed possible that in a DC-T cell co-culture (FIG. 2A) DC-SIGN might facilitate both capture of HIV-1 on DC, independent from CD4 and CCR5, and the subsequent transmission of HIV-1 to the CD4/CCR5-positive T cells. To test this, THP-DC-SIGN transfectants, which do not express CD4 or CCR5 (FIG. 1C) and which cannot be infected by HIV-1, were pulsed with single-round HV-luciferase virus pseudotyped with the $HIV-1_{ADA}$ envelope glycoprotein. After washing to remove unbound virus, the cells were co-cultured with CD4/CCR5-expressing 293 T cells, which are permissive for HIV-1 infection, or activated T lymphocytes. THP-DC-SIGN cells were able to capture the pseudotyped virus and transmit it to the target cells that expressed the receptors required for viral entry (FIG. 4A). HIV-1 capture was completely DC-SIGN dependent, as antibodies against DC-SIGN inhibited HIV-1 infection (FIG. 4A) and DC-SIGN-negative parental THP-1 cells were unable to capture and transmit HIV-1 (FIGS. 4A and 4B). DC-SIGN-mediated infection of the target cells was not due to DC-SIGN binding to ICAM-3, since 293T cells are ICAM-3-negative. These findings indicate that DC-SIGN expressed at the surface of heterologous cells can capture HIV-1 in a form that retains its capacity to subsequently infect HIV-1-permissive cells. The ability of DC-SIGN to capture and transmit HIV-1 was also observed with HIV-luciferase viruses pseudotyped with envelope glycoproteins from an additional five CCR5-tropic isolates, including three primary isolates (FIG. 4B) and from with HIV-luciferase viruses pseudotyped with envelope glycoproteins from CXCR4-tropic isolates.

Figure 4C:
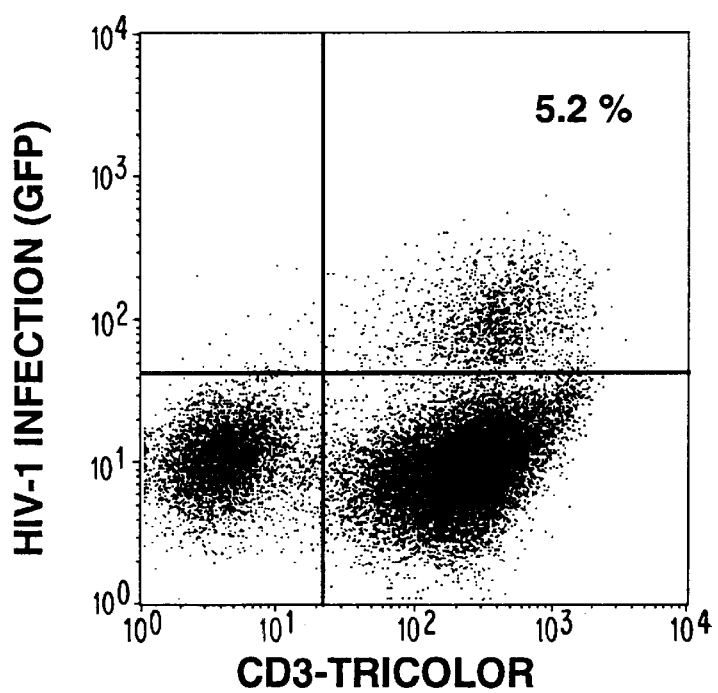

Analysis of luciferase activity in both adherent (293T-CD4-CCR5) and non-adherent (THP-DC-SIGN) cell fractions after 2 days of co-culture demonstrated that productive HIV-1 infection occured only in the HIV-1 permissive 293T-CD4-CCR5 cells. Similarly, by using a pseudotyped HIV-1 vector with the green fluorescent protein gene in place of Nef (HIV-eGFP), it was demonstrated that cells expressing D4/CCR5 and not those expressing DC-SIGN were infected in co-cultures. Thus, after co-culture of virus-pulsed THP-DC-SIGN cells with T cells, only the $CD3^+$ T cells expressed virus-encoded GFP (FIG. 4C).

Figure 5B:
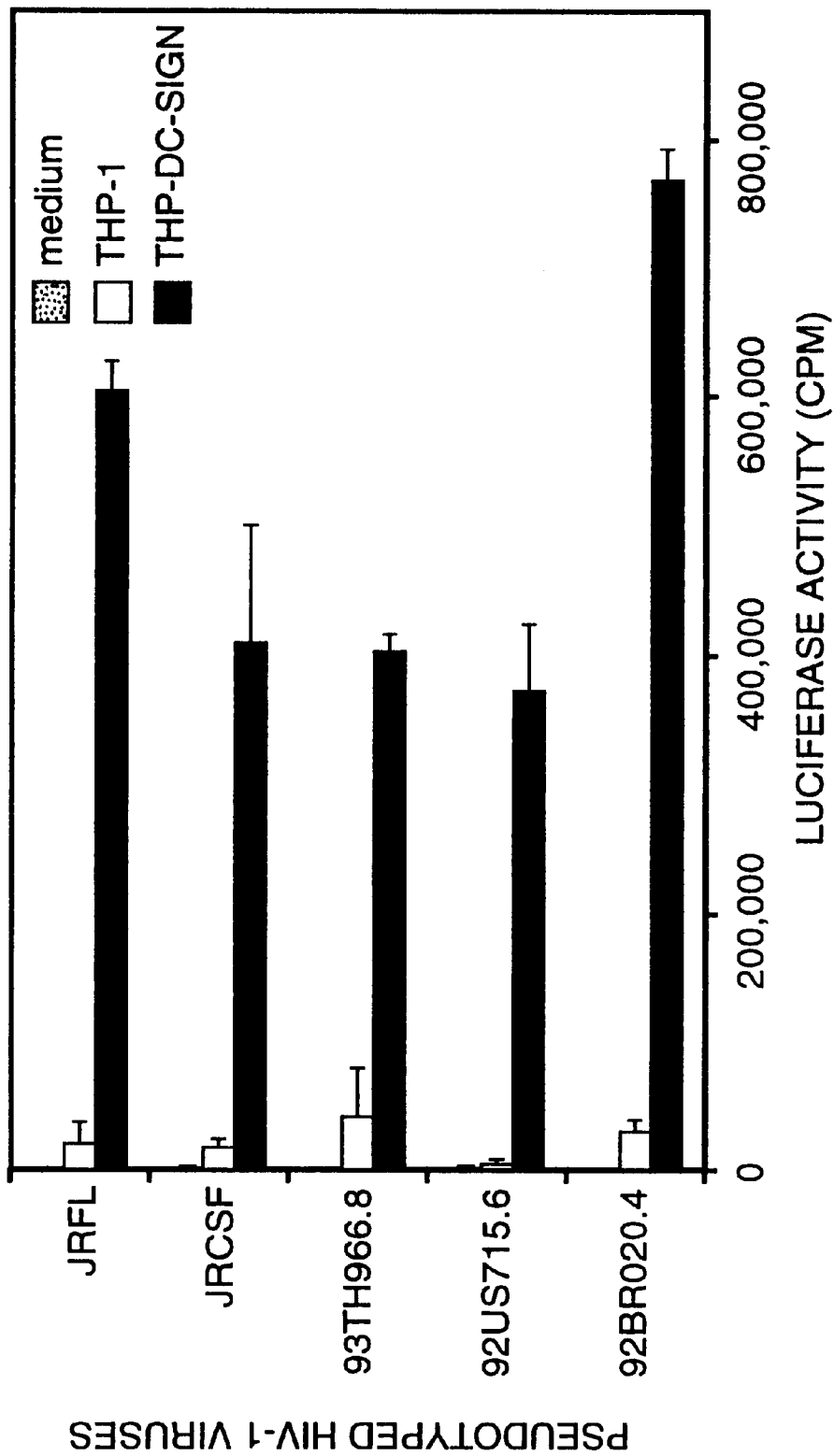

Sexual transmission of HIV-1 is likely to require a means for small amounts of virus to gain access to cells that are permissive for viral replication. This may be achieved because of the ability of virus to interact with DC, which can capture HIV-1 and present it to the permissive cells. To mimic in-vivo conditions in which HIV-1 levels are likely to be limiting, THP-1 transfectants were challenged with low titers of pseudotyped HIV-1 and subsequently co-cultured these cells with HIV-1 permissive cells, without washing away unbound virus (FIG. 5A). As expected, neither 293T-CD4-CCR5 cells nor activated T cells were efficiently infected with the low titers of pseudotyped HIV-1 (FIG. 5A). Strikingly, when these permissive cells were challenged with an identical amount of HIV-1 in the presence of THP-DC-SIGN, but not of the parental THP-1 cells, efficient HIV-1 infection was observed in trans (FIG. 5A). The enhancement of HIV-1 infection of 293-CD4-CCR5 by DC-SIGN was also observed with HIV-luciferase viruses pseudotyped with five other R5 envelopes, including three from primary virus isolates (FIG. 5B). These results indicate that DC-SIGN not only sequesters HIV-1, but also enhances CD4-CCR5 mediated HIV-1 entry by presentation in trans to the HIV-1 receptor complex. Antibodies against DC-SIGN completely inhibited infection (FIG. SA), demonstrating that the efficient enhancement of HIV-1 entry into CD4/CCR5 positive cells is DC-SIGN dependent.

DC present in mucosal tissues at sites of HIV-1 exposure express DC-SIGN and are CCR5-negative: Demonstration that cells which express DC-SIGN can capture HIV-1 and efficiently transmit the virus to other cells in trans suggested that DC that express this C-type lectin have a key role in viral infection in vivo. To determine whether such cells are indeed present in vivo, immunohistochemical analyses of mucosal tissues were performed that are the sites of first exposure during sexual transmission of HIV-1 (FIGS. 6A–6C). DC-SIGN was expressed on DC-like cells with large and very irregular morphology that were present in the mucosal tissues, such as rectum, cervix and uterus (FIGS. 6A–6C respectively), in regions beneath the stratified squamous epithelium in the lamina propria. Analyses of serial sections stained for CD3, CD20, CD14 and CD68 confirmed that DC-SIGN expressing cells were distinct from T cells, B cells, monocytes and macrophages. Similarly, staining of lymph nodes and skin shows DC-restricted expression of DC-SIGN. The comparison of the expression of DC-SIGN, CD4 and CCR5 on DC in the mucosa of the uterus and rectum was made, and it was found that in serial sections that the majority of DC-SIGN-positive DC in these tissues co-expressed CD4 but lacked CCR5 (FIGS. 6D–6F). This indicates that DC present at mucosal sites that have first contact with HIV-1 during sexual transmission, are not infected with HIV-1 through usage of CD4/CCR5. This observation is consistent with the recent demonstration that DC at sites of mucosal infection of non-human primates do not become infected [Stahl-Hennig et al., Science, 285 (5431):1261–1265 (1999)].

DC-SIGN-bound HIV-1 retains infectivity after long-term culture: If HIV-1 gains access to secondary lymphoid organs by way of binding to DC, then virus would have to retain infectivity during the transport from the mucosal tissues to the T cell zones in draining lymph nodes. To determine if virus bound to DC-SIGN retains its infectivity for a prolonged period of time, a time-course experiment was first conducted to determine the length of time that HIV-1 gp120 remains bound to DC-SIGN that was expressed on transfected THP-1 cells. gp120-coated beads was observed to remain bound to DC-SIGN for more than 60 hours (FIG. 7A). Next, the length of time during which HIV-1-pulsed THP-DC-SIGN cells could retain infectious virus was investigated. The DC-SIGN expressing transfectants were pulsed with pseudotyped HIV-1 for 4 hours and then washed extensively. The pulsed cells were subsequently placed in culture and were removed at defined intervals and co-cultured with activated T cells (FIG. 7B). Unexpectedly, after four days the HIV-1 pulsed cells were still able to efficiently infect target cells. In contrast, virus in the absence of DC-SIGN positive cells lost its infectivity after one day (see also FIG. 12). These findings support the hypothesis that limiting numbers of HIV-1 particles, captured by mucosal DC that express DC-SIGN and CD4 but not CCR5, retain infectivity during and after migration to regional lymphoid tissues. T cells, which express CD4 and CCR5, would then be productively infected due to DC-SIGN-mediated enhanced trans-infectivity of the small numbers of HIV-1 particles (FIG. 7C).

Figure 9:
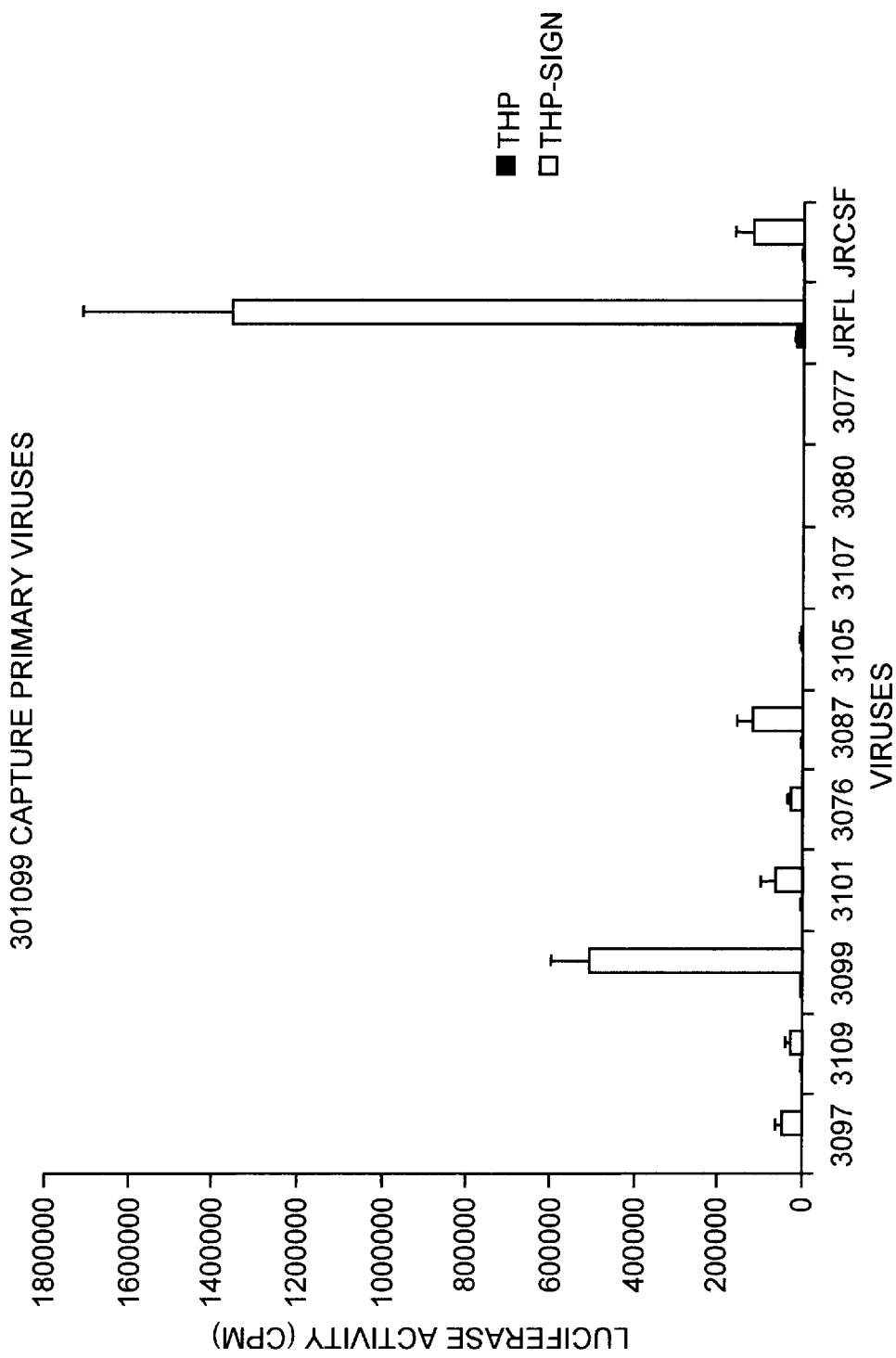
FIG. 9 shows that DC-SIGN mediates capture of HIV pseudotyped with envelopes from primary viral strains. (See FIG. 8 for assay conditions; the same assay was performed except different viruses were examined).

The results described above have general applicability to all HIV strains and T cell types. Thus, FIG. 8 shows that DC-SIGN mediates capture of SIV, CCR5, CXR4, and dual tropic HIV. Viruses encoding the reporter gene luciferase were pseudotyped with envelopes from the CCR5 tropic strains JRFL, ADA, and JRCSF; the CXR4 tropic strains HxB2 and LAI; the dual tropic strain 89.6; and SIV lAl 1. THP or THP-DCSIGN cells were pulsed with these viruses, washed, and then added to target cells. Luciferase activity was measured as an indicator of viral infection of targets (FIG. 8). As is readily apparent, in all cases a striking increase in luciferase activity was observed when the HIV capture was performed in the presence of a facilitator cell that expressed DC-SIGN. The same result was observed with HIV pseudotyped with envelopes from primary viral strains (FIG. 9).

FIG. 10 shows the enhancement of CXR4-tropic HIV infection of activated T cells. THP, THP-DCSIGN cells, DC, or DC preincubated with anti-DCSIGN antibody, were incubated with HxB2 pseudotyped virus encoding the luciferase reporter gene, followed by addition of activated T cell targets. These results further confirm that the enhancement due to dendritic cells is DC-SIGN dependent even when the co-receptor, i.e., the translocating promoter, is CXR4. The enhancement of CXR4-tropic HIV infection is also found for unactivated T cells, albeit to a lessor extant than in activated T cells. Indeed, there is an almost twenty-fold increase in luciferase activity related to HIV capture by naive cells performed in the presence of THP-SIGN cells relative to that performed in the presence of THP cells that do not express DC-SIGN. FIG. 12 shows that binding to cells expressing DC-SIGN significantly extends the longevity of HxB2, a CXR4-tropic virus. In this case, whereas the infectivity of virus rapidly decreases after one day, in the absence of a cell expressing DC-SIGN, in the presence of a cell expressing DC-SIGN the infectivity of the virus reaches a peak at three days and remains significant at least until five days.

Discussion

A novel dendritic cell-specific adhesion receptor, DC-SIGN, has been identified that is identical to the high affinity HIV-1 gp120 binding C-type lectin cloned from a human placental cDNA library [Curtis et al., Proc. Natl. Acad. Sci. U.S.A., 89:8356–8360 (1992)]. However, the present results indicate that contrary to the prior observation, DC-SIGN is specifically expressed in dendritic cells (DC). Furthermore, DC that express both DC-SIGN and CD4 preferentially use DC-SIGN to capture HIV-1 via its high affinity for HIV-1 gp120. DC-SIGN not only efficiently recruits HIV-1 but also facilitates HIV-1 infection of CD4$^+$T cells by a novel in trans mechanism. These findings indicate that HIV-1 utilizes a novel receptor strategy which has not been previously described in other viral systems, and suggest that the virus exploits multiple cell surface receptor systems to ensure that it can establish a productive infection in its host organism.DC localized in the skin and mucosal tissues such as the rectum, uterus, and cervix have been proposed to play a role in initial HIV-1 infection. DC constitute a heterogeneous population of cells that are present in minute numbers in various tissues just beneath the dermis or mucosal layer, and form a first-line defense against viruses and other pathogens. DC have previously been shown to sequester HIV-1 and efficiently transmit the virus to CD4+ T cells. This property of DC, as disclosed herein, can be ascribed to the ability of HIV-1 to bind specifically to these cells through the interaction of gp120 with DC-SIGN. DC thus efficiently capture HIV-1 through a specific interaction that is independent from binding of virus to CD4 and CCR5. DC-SIGN cannot mediate HIV-1 entry, but rather functions as a unique HIV-1 trans-receptor facilitating HIV-1 infection of CD4/CCR5-positive T cells (FIGS. 4 and 5). At low virus titer, CD4/CCR5-expressing cells are not detectably infected without the help of DC-SIGN in trans (FIG. 5A). Conditions in which the number of HIV-1 particles is limiting are likely to resemble those found in vivo, and the results thus suggest that DC-SIGN may be required for viruses to be transmitted from mucosa to T cells that express CD4 and chemokine receptors. In addition, the present results demonstrate that virus bound to DC-SIGN is remarkably stable, and can thus retain infectivity for the prolonged periods of time required for DC to traffic via lymphatics from mucosa to regional lymph nodes (FIGS. 7A and 7B).

Mechanism of DC-SIGN-mediated enhancement of HIV-1 infectivity: The mechanisms by which HIV-1 exploits the machinery of DC and the properties of DC-SIGN to achieve efficient infection of cells that are competent for viral replication remain unclear. The process through which DC-SIGN promotes efficient infection in trans of cells through their CD4/chemokine receptor complex is of particular interest. Binding of the viral envelope glycoprotein to DC-SIGN may induce a conformational change that enables a more efficient interaction with CD4 and/or the chemokine receptor. As multiple conformational transitions are required before the envelope glycoprotein initiates fusion with target membranes [Chan and Kim, *Cell*, 93(5): 681–684 (1997)], the binding of DC-SIGN to gp120 may facilitate or stabilize one of these transitions. Anti-gp120 antibodies that increase infectivity of viral particles have been described [Lee et al., *J. Virol.*, 71(8):6037–6043 (1997)], and it is likely that DC-SIGN has a similar effect upon binding to the envelope glycoprotein. Alternatively, binding of viral particles to DC-SIGN may focus or concentrate them at the surface of the DC, and could thus increase the probability that entry will occur after they bind to the receptor complex on target cells. In any case, it is clear that DC-SIGN enhances the infection of T cells since at low multiplicity of infection (MOI) T cells are not infected in the absence of DC-SIGN.

Whether a transient quaternary complex is formed between DC-SIGN, HIV-1 Env, CD4 and CCR5 remains to be determined. Elucidation of the crystal structure of a gp120-CD4 complex has revealed that most glycosylation sites within gp120 reside in a ridge that flanks the CD4 binding pocket [Kwong et al., *Nature*, 393(6686), 648–659 (1998)]. Since mannans block the binding of gp120 to DC-SIGN, it is likely that this C-type lectin binds to one or more carbohydrate moieties in gp120. It remains possible, however, that the lectin domain of DC-SIGN interacts with the polypeptide backbone of gp120. Mutant forms of gp120 and soluble DC-SIGN will aid in the elucidation of the mechanism of enhanced infectivity in trans.

DC-SIGN, as disclosed herein, binds to ICAM-3, which is expressed constitutively on the surface of T lymphocytes. Enhancement of target cell infectivity by DC-SIGN-bound HIV-1 is not dependent on the presence of ICAM-3 on target cells. However, enhancement of infectivity was consistently better when target cells were T cells rather than 293-CD4-CCR5 cells. It remains possible that the efficiency of viral transmission from carrier DC to target T cells may also be enhanced by specific adhesive interactions other than the DC-SIGN-ICAM 3 interaction, such as LFA-1-ICAM-1 which predominates the adhesion between DC and activated T cells. Therefore, antibodies raised against DC-SIGN do not inhibit the DC-T cell transmission of HIV-1 post-infection (FIG. 2C).

Role of DC in HIV infection in vivo: The only HIV-1 receptors previously known to have a role in HIV-1 entry were CD4 and a subset of the G-protein coupled chemokine receptors, such as CCR5 and CXCR4. CCR5 functions as the major receptor for strains of virus previously classified as "macrophage-tropic", and only those strains that can utilize this chemokine receptor can be efficiently transmitted between individuals [Littman, *Cell*, 93:677–80 (1998)]. Other gp120 binding receptors had been previously identified, including DC-SIGN and galactosyl ceramide [Harouse et al., *Science*, 253(5017):320–323 (1991)], but these had not been shown to be involved in viral entry. The present disclosure shows that DC-SIGN not only binds HIV-1, but also sequesters HIV-1 and thereby catalyzes its entry into cells that express CD4 and a chemokine receptor (s). The present results and the pattern of expression of the different receptors in mucosal tissues are consistent with DC-SIGN having a key function in the early stages of viral infection. Remarkably, the immunohistochemical analyses, disclosed herein, clearly demonstrate that CCR5 is not expressed in the lamina propria of HIV-1 related mucosal tissue FIG. 6), whereas DC-SIGN is abundantly expressed. This observation confirms and extends the findings of Hladik et al., who showed that DC present in the genital tract also lack CCR5 [Hladik et al., *J. Virol.*, 73(7):5833–42], and the present results indicate that HIV-1 cannot infect DC present at mucosal sites.

DC-SIGN therefore plays a crucial role in initial HIV-1 exposure by mediating viral binding to DC present in mucosal tissues, rather than infection of these cells. The high level of expression of DC-SIGN on immature DC and its high affinity for gp120, which exceeds that of CD4 [Curtis et al., *Proc. Natl. Acad. Sci. U.S.A.*, 89:8356–8360 (1992)], indicate that DC-SIGN is endowed with the ability to efficiently capture HIV-1, even when the virus is present in minute amounts. HIV-1 may subsequently exploit the migratory capacity of the DC to gain access to the T cell compartment in lymphoid tissues. DC must be activated to commence their migration, and it is hence possible that multimerization of DC-SIGN on the cell surface of DC by interaction with the multivalent virus particles may initiate this process. Interestingly, the time course of HIV-1 stability when associated with DC-SIGN shows that DC-SIGN is able to capture and bind to HIV-1 for more than 4 days, after which the virus can still infect permissive cells. This long-term preservation of HIV-1 in an infectious state would appear to allow sufficient time for it to be transported by DC trafficking from mucosal surfaces to lymphoid compartments, where virus can be transmitted (FIG. 7C) [see also Steinman et al., *Immunol. Rev.*, 156:25–37 (1997)]. Several groups have reported that DC can migrate from the periphery to draining lymph nodes within two days after antigen exposure or HIV-1 challenge [Barratt-Boyes et al., *J. Immunol.*, 158(10): 4543–7 (1997); Stahl-Hennig et al., *Science*, 285(5431):1261–5 (1999)]. Viral particles have also been reported within endocytic vesicles of DC. This observation suggests that DC-SIGN-bound HIV-1 may be internalized and protected during the time required for the cells to complete their journey to the regional lymph nodes.

The present results indicate that after HIV-1 has been ferried by DC to the lymphoid compartment, DC-SIGN presents the bound viral particles to the CD4/CCR5 complex present on T cells and greatly enhances their entry into these cells (see schematic in FIG. 7C). Monoclonal antibodies directed against DC-SIGN have been shown to block productive infection occurring in the T cell co-cultures with CD4/CCR5-positive monocyte-derived DC. Therefore, even in the presence of obligatory HIV-1 receptors present in cis on target cells, DC-SIGN functions as a trans-receptor for HIV-1 infection of T cells and is critical in the primary co-cultures. This is the first example of such a receptor that works primarily in trans. Interestingly, CD4 can also facilitate HIV-1 infection of CD4-negative cells that express CCR5 by a trans-receptor mechanism, although it remains unclear whether this is an important route of infection in vivo [Speck et al, Curr. Biol., 9(10):547–50 (1999)]. In that case, interaction of envelope glycoprotein with CD4 results in a conformational change that permits binding of the virus to CCR5 on CD4-negative cells. Together with the results presented here, these studies indicate that HIV-1 can use receptors in trans to facilitate infection of cells which otherwise may be difficult to infect either because of lack of proper receptors or because of their anatomical distribution relative to the sites of HIV-1 exposure. The discovery of the role of DC-SIGN in HIV-1 infection may have significant implications for understanding the mechanism of HIV-1 transmission and for developing strategies to prevent or block viral infection.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are all incorporated by references in their entireties.

What is claimed is:

1. A method of identifying a compound that inhibits the trans-enhancement of Human Immunodeficiency Virus (HIV) entry into a cell comprising:

(a) contacting a first cell in vitro with a vector in the presence of a test compound, wherein the vector comprises an HIV envelope protein that binds dendritic cell-specific C-type lectin (DC-SIGN), wherein the first cell expresses DC-SIGN, and wherein a DC-SIGN-HIV envelope protein complex forms between the first cell and the vector in the absence of the test compound;

(b) removing unbound vector and test compound from the first cell;

(c) contacting a second cell in vitro with the first cell; wherein the second cell is susceptible to entry of vectors comprising the HIV envelope protein; and enhancement of HIV entry into a cell when the amount of vector entry is less when the test compound is present in step (a) than when it is absent in step (a).

2. The method of claim 1 wherein said removing of step (b) comprises washing the unbound vector and the test compound away from first cell.

3. The method of claim 1 wherein the second cell is a T cell or macrophage.

4. The method of claim 1 wherein the second cell expresses CD4 and a translocation promoting agent selected from the group consisting of CCR5, CXCR4, CCR2b, CCR3, Bonzo, and BOB.

5. The method of claim 4 wherein the translocation promoting agent is CCR5 and the HIV envelope protein is from the Human Immunodeficiency Viral Strain JRFL.

6. The method of claim 1 wherein the vector contains a marker protein and step (d) is performed by determining the amount of marker protein expressed in the cell.

7. The method of claim 6 wherein the marker protein is selected from the group consisting of luciferase and green fluorescent protein.

8. A method of identifying a compound that inhibits the trans-enhancement of Human Immunodeficiency Virus (HIV) entry into a cell comprising:
(a) contacting a first cell in vitro with a vector and a second cell in vitro in the presence of a test compound, wherein the vector comprises an HIV envelope protein that binds dendritic cell-specific C-type lectin (DC-SIGN), wherein the first cell expresses DC-SIGN, wherein a DC-SIGN-HIV envelope protein complex forms between the first cell and the vector in the absence of the test compound; and wherein the second cell is susceptible to entry of vectors comprising the HIV envelope protein; and
(b) determining the amount of vector that has entered the second cell; wherein a test compound is identified as a compound that inhibits with the trans-enhancement of HIV entry.

9. The method of claim 8 wherein the second cell is a T cell or macrophage.

10. The method of claim 8 wherein the second cell expresses CD4 and a translocation promoting agent selected from the group consisting of CCR5, CXCR4, CCR2b, CCR3, Bonzo, and BOB.

11. The method of claimswherein the translocation promoting agent is CCR5 and the HIV envelope protein is from the Human Immunodeficiency Viral Strain JRFL.

12. The method of claim 1 wherein the vector contains a marker protein and step (d) is performed by determining the amount of marker protein expressed in the cell.

13. The method of claim 6 wherein the marker protein is selected from the group consisting of luciferase and green fluorescent protein.

* * * * *

SEQUENCE LISTING

```
<160> NUMBER OF SEQ ID NOS: 17

<210> SEQ ID NO 1
<211> LENGTH: 1312
<212> TYPE: DNA
<213> ORGANISM: Homo sapiens
<220> FEATURE:
<221> NAME/KEY: CDS
<222> LOCATION: (42)..(1253)

<400> SEQUENCE: 1
ctaaagcagg agttctggac actggggag agtggggtga c atg agt gac tcc aag         56
                                            Met Ser Asp Ser Lys
                                             1               5 gaa cca aga ctg cag cag ctg ggc ctc ctg gag gag gaa cag ctg aga        104
Glu Pro Arg Leu Gln Gln Leu Gly Leu Leu Glu Glu Glu Gln Leu Arg
            10                  15                  20 ggc ctt gga ttc cga cag act cga gga tac aag agc tta gca ggg tgt        152
Gly Leu Gly Phe Arg Gln Thr Arg Gly Tyr Lys Ser Leu Ala Gly Cys
        25                  30                  35 ctt ggc cat ggt ccc ctg gtg ctg caa ctc ctc tcc ttc acg ctc ttg        200
Leu Gly His Gly Pro Leu Val Leu Gln Leu Leu Ser Phe Thr Leu Leu
    40                  45                  50 gct ggg ctc ctt gtc caa gtg tcc aag gtc ccc agc tcc ata agt cag        248
Ala Gly Leu Leu Val Gln Val Ser Lys Val Pro Ser Ser Ile Ser Gln
55                  60                  65 gaa caa tcc agg caa gac gcg atc tac cag aac ctg acc cag ctt aaa        296
Glu Gln Ser Arg Gln Asp Ala Ile Tyr Gln Asn Leu Thr Gln Leu Lys
                70                  75                  80                  85 gct gca gtg ggt gag ctc tca gag aaa tcc aag ctg cag gag atc tac        344
Ala Ala Val Gly Glu Leu Ser Glu Lys Ser Lys Leu Gln Glu Ile Tyr
                    90                  95                 100 cag gag ctg acc cag ctg aag gct gca gtg ggt gag ctt cca gag aaa        392
Gln Glu Leu Thr Gln Leu Lys Ala Ala Val Gly Glu Leu Pro Glu Lys
                105                 110                 115 tct aag ctg cag gag atc tac cag gag ctg acc cgg ctg aag gct gca        440
Ser Lys Leu Gln Glu Ile Tyr Gln Glu Leu Thr Arg Leu Lys Ala Ala
            120                 125                 130 gtg ggt gag ctt cca gag aaa tct aag ctg cag gag atc tac cag gag        488
Val Gly Glu Leu Pro Glu Lys Ser Lys Leu Gln Glu Ile Tyr Gln Glu
```

```
Val Gly Glu Leu Pro Glu Lys Ser Lys Leu Gln Glu Ile Tyr Gln Glu
    135                 140                 145 ctg acc tgg ctg aag gct gca gtg ggt gag ctt cca gag aaa tct aag       536
Leu Thr Trp Leu Lys Ala Ala Val Gly Glu Leu Pro Glu Lys Ser Lys
150                 155                 160                 165 atg cag gag atc tac cag gag ctg act cgg ctg aag gct gca gtg ggt       584
Met Gln Glu Ile Tyr Gln Glu Leu Thr Arg Leu Lys Ala Ala Val Gly
                170                 175                 180 gag ctt cca gag aaa tct aag cag cag gag atc tac cag gag ctg acc       632
Glu Leu Pro Glu Lys Ser Lys Gln Gln Glu Ile Tyr Gln Glu Leu Thr
            185                 190                 195 cgg ctg aag gct gca gtg ggt gag ctt cca gag aaa tct aag cag cag       680
Arg Leu Lys Ala Ala Val Gly Glu Leu Pro Glu Lys Ser Lys Gln Gln
        200                 205                 210 gag atc tac cag gag ctg acc cgg ctg aag gct gca gtg ggt gag ctt       728
Glu Ile Tyr Gln Glu Leu Thr Arg Leu Lys Ala Ala Val Gly Glu Leu
    215                 220                 225 cca gag aaa tct aag cag cag gag atc tac cag gag ctg acc cag ctg       776
Pro Glu Lys Ser Lys Gln Gln Glu Ile Tyr Gln Glu Leu Thr Gln Leu
230                 235                 240                 245 aag gct gca gtg gaa cgc ctg tgc cac ccc tgt ccc tgg gaa tgg aca       824
Lys Ala Ala Val Glu Arg Leu Cys His Pro Cys Pro Trp Glu Trp Thr
                250                 255                 260 ttc ttc caa gga aac tgt tac ttc atg tct aac tcc cag cgg aac tgg       872
Phe Phe Gln Gly Asn Cys Tyr Phe Met Ser Asn Ser Gln Arg Asn Trp
            265                 270                 275 cac gac tcc atc acc gcc tgc aaa gaa gtg ggg gcc cag ctc gtc gta       920
His Asp Ser Ile Thr Ala Cys Lys Glu Val Gly Ala Gln Leu Val Val
        280                 285                 290 atc aaa agt gct gag gag cag aac ttc cta cag ctg cag tct tcc aga       968
Ile Lys Ser Ala Glu Glu Gln Asn Phe Leu Gln Leu Gln Ser Ser Arg
    295                 300                 305 agt aac cgc ttc acc tgg atg gga ctt tca gat cta aat cag gaa ggc      1016
Ser Asn Arg Phe Thr Trp Met Gly Leu Ser Asp Leu Asn Gln Glu Gly
310                 315                 320                 325 acg tgg caa tgg gtg gac ggc tca cct ctg ttg ccc agc ttc aag cag      1064
Thr Trp Gln Trp Val Asp Gly Ser Pro Leu Leu Pro Ser Phe Lys Gln
                330                 335                 340 tat tgg aac aga gga gag ccc aac aac gtt ggg gag gaa gac tgc gcg      1112
Tyr Trp Asn Arg Gly Glu Pro Asn Asn Val Gly Glu Glu Asp Cys Ala
            345                 350                 355 gaa ttt agt ggc aat ggc tgg aac gac gac aaa tgt aat ctt gcc aaa      1160
Glu Phe Ser Gly Asn Gly Trp Asn Asp Asp Lys Cys Asn Leu Ala Lys
        360                 365                 370 ttc tgg atc tgc aaa aag tcc gca gcc tcc tgc tcc agg gat gaa gaa      1208
Phe Trp Ile Cys Lys Lys Ser Ala Ala Ser Cys Ser Arg Asp Glu Glu
    375                 380                 385 cag ttt ctt tct cca gcc cct gcc acc cca aac ccc cct cct gcg           1253
Gln Phe Leu Ser Pro Ala Pro Ala Thr Pro Asn Pro Pro Pro Ala
390                 395                 400 tagcagaact tcaccccctt ttaagctaca gttccttctc tccatccttc gacctttag     1312

<210> SEQ ID NO 2
<211> LENGTH: 404
<212> TYPE: PRT
<213> ORGANISM: Homo sapiens

<400> SEQUENCE: 2

Met Ser Asp Ser Lys Glu Pro Arg Leu Gln Gln Leu Gly Leu Leu Glu
  1               5                  10                  15
```

```
Glu Glu Gln Leu Arg Gly Leu Gly Phe Arg Gln Thr Arg Gly Tyr Lys
            20                  25                  30

Ser Leu Ala Gly Cys Leu Gly His Gly Pro Leu Val Leu Gln Leu Leu
            35                  40                  45

Ser Phe Thr Leu Leu Ala Gly Leu Leu Val Gln Val Ser Lys Val Pro
            50                  55                  60

Ser Ser Ile Ser Gln Glu Gln Ser Arg Gln Asp Ala Ile Tyr Gln Asn
65                  70                  75                  80

Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
            115                 120                 125

Arg Leu Lys Ala Ala Val Gly Glu Leu Pro Glu Lys Ser Lys Leu Gln
            130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
            165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
            195                 200                 205

Lys Ser Lys Gln Gln Glu Ile Tyr Gln Glu Leu Thr Arg Leu Lys Ala
            210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
            245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
            275                 280                 285

Ala Gln Leu Val Val Ile Lys Ser Ala Glu Glu Gln Asn Phe Leu Gln
            290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
            325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys
            355                 360                 365

Cys Asn Leu Ala Lys Phe Trp Ile Cys Lys Lys Ser Ala Ala Ser Cys
            370                 375                 380

Ser Arg Asp Glu Glu Gln Phe Leu Ser Pro Ala Pro Ala Thr Pro Asn
385                 390                 395                 400

Pro Pro Pro Ala

<210> SEQ ID NO 3
<211> LENGTH: 458
<212> TYPE: PRT
```

-continued

```
<213> ORGANISM: Homo sapiens

<400> SEQUENCE: 3

Met Asn Arg Gly Val Pro Phe Arg His Leu Leu Leu Val Leu Gln Leu
 1               5                  10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
         50                  55                  60

Gln Gly Ser Phe Leu Thr Lys Gly Pro Ser Lys Leu Asn Asp Arg Ala
 65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Trp Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400
```

```
Val Leu Gly Gly Val Ala Gly Leu Leu Phe Ile Gly Leu Gly Ile
                405                 410                 415

Phe Phe Cys Val Arg Cys Arg His Arg Arg Gln Ala Glu Arg Met
            420                 425                 430

Ser Gln Ile Lys Arg Leu Leu Ser Glu Lys Thr Cys Gln Cys Pro
        435                 440                 445

His Arg Phe Gln Lys Thr Cys Ser Pro Ile
        450                 455

<210> SEQ ID NO 4
<211> LENGTH: 352
<212> TYPE: PRT
<213> ORGANISM: Homo sapiens

<400> SEQUENCE: 4

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320
```

-continued

Ser Arg Gly Ser Ser Leu Lys Ile Leu Ser Lys Gly Lys Arg Gly Gly
              325                 330                 335

His Ser Ser Val Ser Thr Glu Ser Glu Ser Ser Ser Phe His Ser Ser
              340                 345                 350

<210> SEQ ID NO 5
<211> LENGTH: 352
<212> TYPE: PRT
<213> ORGANISM: Homo sapiens

<400> SEQUENCE: 5

Met Asp Tyr Gln Val Ser Ser Pro Thr Tyr Asp Ile Asp Tyr Asp Thr
 1               5                  10                  15

Ser Glu Pro Cys Gln Lys Ile Asn Val Lys Gln Ile Ala Ala Arg Leu
             20                  25                  30

Leu Pro Pro Leu Tyr Ser Leu Val Phe Ile Phe Gly Phe Val Gly Asn
         35                  40                  45

Met Leu Val Ile Leu Val Leu Ile Asn Cys Lys Arg Leu Lys Ser Met
 50                  55                  60

Thr Asp Ile Tyr Leu Leu Asn Leu Ala Ile Ser Asp Leu Phe Phe Leu
 65                  70                  75                  80

Leu Thr Val Pro Phe Trp Ala His Tyr Ala Ala Ala Gln Trp Asp Phe
                 85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Ile Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys His Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu

```
            340             345             350

<210> SEQ ID NO 6
<211> LENGTH: 726
<212> TYPE: PRT
<213> ORGANISM: Homo sapiens

<400> SEQUENCE: 6

Met Glu Gly Glu Arg Lys Asn Asn Asn Lys Arg Trp Tyr Phe Thr Arg
  1               5                  10                  15

Glu Gln Leu Glu Asn Ser Pro Ser Arg Arg Phe Gly Val Asp Pro Asp
             20                  25                  30

Lys Glu Leu Ser Tyr Arg Gln Gln Ala Ala Asn Leu Leu Gln Asp Met
         35                  40                  45

Gly Gln Arg Leu Asn Val Ser Gln Leu Thr Ile Asn Thr Ala Ile Val
     50                  55                  60

Tyr Met His Arg Phe Tyr Met Ile Gln Ser Phe Thr Gln Phe Pro Gly
 65                  70                  75                  80

Asn Ser Val Ala Pro Ala Ala Leu Phe Leu Ala Ala Lys Val Glu Glu
                 85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
        115                 120                 125

Gln Val Gln Asp Leu Val Ile Leu Glu Ser Ile Ile Leu Gln Thr Leu
    130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
            180                 185                 190

Pro Pro Val Val Ala Cys Val Cys Ile His Leu Ala Cys Lys Trp Ser
        195                 200                 205

Asn Trp Glu Ile Pro Val Ser Thr Asp Gly Lys His Trp Trp Glu Tyr
    210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
            260                 265                 270

Gly Thr Asp Glu Lys Thr Ser Glu Gln Thr Ile Leu Asn Met Ile Ser
        275                 280                 285

Gln Ser Ser Asp Thr Thr Ile Ala Gly Leu Met Ser Met Ser Thr
    290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335

Ser Gln Pro Ser Phe Lys Leu Glu Pro Thr Gln Gly His Arg Thr Ser
            340                 345                 350

Glu Asn Leu Ala Leu Thr Gly Val Asp His Ser Leu Pro Gln Asp Gly
        355                 360                 365
```

```
Ser Asn Ala Phe Ile Ser Gln Lys Gln Asn Ser Lys Ser Val Pro Ser
    370                 375                 380

Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
                405                 410                 415

Gln Tyr Ala Tyr Ala Ala Gln Asn Leu Leu Ser His His Asp Ser His
                420                 425                 430

Ser Ser Val Ile Leu Lys Met Pro Ile Glu Gly Ser Glu Asn Pro Glu
            435                 440                 445

Arg Pro Phe Leu Glu Lys Ala Asp Lys Thr Ala Leu Lys Met Arg Ile
        450                 455                 460

Pro Val Ala Gly Gly Asp Lys Ala Ala Ser Lys Pro Glu Glu Ile
465                 470                 475                 480

Lys Met Arg Ile Lys Val His Ala Ala Asp Lys His Asn Ser Val
                485                 490                 495

Glu Asp Ser Val Thr Lys Ser Arg Glu His Lys Glu Lys His Lys Thr
                500                 505                 510

His Pro Ser Asn His His His His Asn His His Ser His Lys His
            515                 520                 525

Ser His Ser Gln Leu Pro Val Gly Thr Gly Asn Lys Arg Pro Gly Asp
    530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Thr Arg Lys Arg Gly Pro
                565                 570                 575

Ser Glu Glu Thr Gly Gly Ala Val Phe Asp His Pro Ala Lys Ile Ala
                580                 585                 590

Lys Ser Thr Lys Ser Ser Ser Leu Asn Phe Ser Phe Pro Ser Leu Pro
            595                 600                 605

Thr Met Gly Gln Met Pro Gly His Ser Ser Asp Thr Ser Gly Leu Ser
    610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
                645                 650                 655

Tyr Gln Asp Thr Val Asn Met Leu His Ser Leu Leu Ser Ala Gln Gly
                660                 665                 670

Val Gln Pro Thr Gln Pro Thr Ala Phe Glu Phe Val Arg Pro Tyr Ser
            675                 680                 685

Asp Tyr Leu Asn Pro Arg Ser Gly Gly Ile Ser Ser Arg Ser Gly Asn
        690                 695                 700

Thr Asp Lys Pro Arg Pro Pro Leu Pro Ser Glu Pro Pro Pro
705                 710                 715                 720

Leu Pro Pro Leu Pro Lys
                725

<210> SEQ ID NO 7
<211> LENGTH: 1742
<212> TYPE: DNA
<213> ORGANISM: Homo sapiens

<400> SEQUENCE: 7
caagcccaga gccctgccat ttctgtgggc tcaggtccct actgctcagc cccttcctcc      60
```

-continued

| | |
|---|---|
| ctcggcaagg ccacaatgaa ccggggagtc ccttttaggc acttgcttct ggtgctgcaa | 120 |
| ctggcgctcc tcccagcagc cactcaggga agaaagtgg tgctgggcaa aaaggggat | 180 |
| acagtggaac tgacctgtac agcttcccag aagaagagca tacaattcca ctggaaaaac | 240 |
| tccaaccaga taaagattct gggaaatcag ggctccttct taactaaagg tccatccaag | 300 |
| ctgaatgatc gcgctgactc aagaagaagc ctttgggacc aaggaaactt cccctgatc | 360 |
| atcaagaatc ttaagataga agactcagat acttacatct gtgaagtgga ggaccagaag | 420 |
| gaggaggtgc aattgctagt gttcggattg actgccaact ctgacaccca cctgcttcag | 480 |
| ggcagagcc tgaccctgac cttggagagc ccccctggta gtagcccctc agtgcaatgt | 540 |
| aggagtccaa ggggtaaaaa catacagggg ggaagaccc tctccgtgtc tcagctggag | 600 |
| ctccaggata gtggcacctg gacatgcact gtcttgcaga accagaagaa ggtggagttc | 660 |
| aaaatagaca tcgtggtgct agcttttccag aaggcctcca gcatagtcta taagaaagag | 720 |
| ggggaacagg tggagttctc cttcccactc gcctttacag ttgaaaagct gacgggcagt | 780 |
| ggcgagctgt ggtggcaggc ggagagggct tcctcctcca agtcttggat caccttgac | 840 |
| ctgaagaaca aggaagtgtc tgtaaaatgg gttacccagg accctaagct ccagatgggc | 900 |
| aagaagctcc cgctccacct caccctgccc caggccttgc ctcagtatgc tggctctgga | 960 |
| aacctcaccc tggcccttga agcgaaaaca ggaaagttgc atcaggaagt gaacctggtg | 1020 |
| gtgatgagag ccactcagct ccagaaaaat ttgacctgtg aggtgtgggg acccacctcc | 1080 |
| cctaagctga tgctgagctt gaaactggag aacaaggagg caaaggtctc gaagcgggag | 1140 |
| aaggcggtgt gggtgctgaa ccctgaggcg gggatgtggc agtgtctgct gagtgactcg | 1200 |
| ggacaggtcc tgctggaatc caacatcaag gttctgccca tggtccac ccggtgcag | 1260 |
| ccaatggccc tgattgtgct gggggcgtc gccggcctcc tgcttttcat tgggctaggc | 1320 |
| atcttcttct gtgtcaggtg ccggcaccga aggcgccaag cagagcggat gtctcagatc | 1380 |
| aagagactcc tcagtgagaa gaagacctgc cagtgccctc accggtttca gaagacatgt | 1440 |
| agccccattt gaggcacgag gccaggcaga tcccacttgc agcctcccca ggtgtctgcc | 1500 |
| ccgcgtttcc tgcctgcgga ccagatgaat gtagcagatc ccacgctctg gcctcctgtt | 1560 |
| cgtcctccct acaatttgcc attgtttctc ctgggttagg ccccggcttc actggttgag | 1620 |
| tgttgctctc tagtttccag aggcttaatc acaccgtcct ccacgccatt ccttttcct | 1680 |
| tcaagcctag cccttctctc attatttctc tctgaccctc tccccactgc tcatttggat | 1740 |
| cc | 1742 |

<210> SEQ ID NO 8
<211> LENGTH: 1059
<212> TYPE: DNA
<213> ORGANISM: Homo sapiens

<400> SEQUENCE: 8

| | |
|---|---|
| atggattatc aagtgtcaag tccaacctat gacatcgatt atgatacatc ggagccctgc | 60 |
| caaaaaatca atgtgaagca atcgcagcc cgcctcctgc ctccactcta ctcactggtg | 120 |
| ttcatctttg gttttgtggg caacatgctg gtcatcctcg tcctgataaa ctgcaaaagg | 180 |
| ctgaagagca tgactgacat ctacctgctc aacctggcca tctctgacct gttttttcctt | 240 |
| cttactgtcc ccttctgggc tcactacgct gctgcccagt gggactttgg aaatacaatg | 300 |
| tgtcaactct tgacagggct ctattttata ggcttcttct ctggaatctt cttcatcatc | 360 |
| ctcctgacaa tcgatagata cctagctatc gtccatgctg tgtttgcttt aaaagccagg | 420 |

```
acggtcacct ttggggtagt gacaagtgtg atcacttggg tggtggctgt gtttgcatct      480
ctcccaggaa tcatctttac cagatctcaa aaagaaggtc ttcattacac ctgcagctct      540
cattttccat acagtcagta tcaattctgg aagaatttcc agacattaaa gatagtcatc      600
ttggggctgg tcctgccgct gcttgtcatg gtcatctgct actcgggaat cctaaaaact      660
ctgcttcggt gtcgaaacga gaagaagagg cacagggctg tgaggcttat cttcaccatc      720
atgattgttt attttctctt ctgggctccc tacaacattg tccttctcct gaacaccttc      780
caggaattct ttggcctgaa taattgcagt agctctaaca ggttggacca agccatgcag      840
gtgacagaga ctcttgggat gacgcactgc tgcatcaacc ccatcatcta tgcctttgtt      900
ggggagaagt tcagaaacta cctcttagtc ttcttccaaa agcatattgc caaacacttc      960
tgcaaatgct gttctatttt ccagcaagag gctcccgagc gagcaagctc agtttacact     1020
cgatccactg gggagcagga aatatcggtg ggcttgtga                            1059
```

<210> SEQ ID NO 9
<211> LENGTH: 342
<212> TYPE: PRT
<213> ORGANISM: Homo sapiens

<400> SEQUENCE: 9

```
Met Ala Glu His Asp Tyr His Glu Asp Tyr Gly Phe Ser Ser Phe Asn
 1               5                  10                  15

Asp Ser Ser Gln Glu Glu His Gln Asp Phe Leu Gln Phe Ser Lys Val
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255
```

-continued

```
His Trp Glu Tyr Tyr Ala Met Thr Ser Phe His Tyr Thr Ile Met Val
                260                 265                 270

Thr Glu Ala Ile Ala Tyr Leu Arg Ala Cys Leu Asn Pro Val Leu Tyr
            275                 280                 285

Ala Phe Val Ser Leu Lys Phe Arg Lys Asn Phe Trp Lys Leu Val Lys
        290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340
```

<210> SEQ ID NO 10
<211> LENGTH: 360
<212> TYPE: PRT
<213> ORGANISM: Homo sapiens

<400> SEQUENCE: 10

```
Met Asp Pro Glu Glu Thr Ser Val Tyr Leu Asp Tyr Tyr Tyr Ala Thr
  1               5                  10                  15

Ser Pro Asn Ser Asp Ile Arg Glu Thr His Ser His Val Pro Tyr Thr
                20                  25                  30

Ser Val Phe Leu Pro Val Phe Tyr Thr Ala Val Phe Leu Thr Gly Val
            35                  40                  45

Leu Gly Asn Leu Val Leu Met Gly Ala Leu His Phe Lys Pro Gly Ser
        50                  55                  60

Arg Arg Leu Ile Asp Ile Phe Ile Ile Asn Leu Ala Ala Ser Asp Phe
 65                  70                  75                  80

Ile Phe Leu Val Thr Leu Pro Leu Trp Val Asp Lys Glu Ala Ser Leu
                 85                  90                  95

Gly Leu Trp Arg Thr Gly Ser Phe Leu Cys Lys Gly Ser Ser Tyr Met
            100                 105                 110

Ile Ser Val Asn Met His Cys Ser Val Leu Leu Leu Thr Cys Met Ser
        115                 120                 125

Val Asp Arg Tyr Leu Ala Ile Val Trp Pro Val Val Ser Arg Lys Phe
    130                 135                 140

Arg Arg Thr Asp Cys Ala Tyr Val Val Cys Ala Ser Ile Trp Phe Ile
145                 150                 155                 160

Ser Cys Leu Leu Gly Leu Pro Thr Leu Leu Ser Arg Glu Leu Thr Leu
                165                 170                 175

Ile Asp Asp Lys Pro Tyr Cys Ala Glu Lys Lys Ala Thr Pro Ile Lys
            180                 185                 190

Leu Ile Trp Ser Leu Val Ala Leu Ile Phe Thr Phe Phe Val Pro Leu
        195                 200                 205

Leu Ser Ile Val Thr Cys Tyr Cys Cys Ile Ala Arg Lys Leu Cys Ala
    210                 215                 220

His Tyr Gln Gln Ser Gly Lys His Asn Lys Leu Lys Ser Ile
225                 230                 235                 240

Lys Ile Ile Phe Ile Val Val Ala Ala Phe Leu Val Ser Trp Leu Pro
                245                 250                 255

Phe Asn Thr Phe Lys Phe Leu Ala Ile Val Ser Gly Leu Arg Gln Glu
            260                 265                 270

His Tyr Leu Pro Ser Ala Ile Leu Gln Leu Gly Met Glu Val Ser Gly
        275                 280                 285
```

```
Pro Leu Ala Phe Ala Asn Ser Cys Val Asn Pro Phe Ile Tyr Tyr Ile
    290                 295                 300

Phe Asp Ser Tyr Ile Arg Arg Ala Ile Val His Cys Leu Cys Pro Cys
305                 310                 315                 320

Leu Lys Asn Tyr Asp Phe Gly Ser Ser Thr Glu Thr Ser Asp Ser His
                325                 330                 335

Leu Thr Lys Ala Leu Ser Thr Phe Ile His Ala Glu Asp Phe Ala Arg
                340                 345                 350

Arg Arg Lys Arg Ser Val Ser Leu
            355                 360

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
agagtggggt gacatgagtg                                            20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
gaagttctgc tacgcaggag                                            20

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 13
gagttctgga cactggggga gagtgggtg acat                             34

<210> SEQ ID NO 14
<211> LENGTH: 1679
<212> TYPE: DNA
<213> ORGANISM: Homo sapiens

<400> SEQUENCE: 14
gtttgttggc tgcggcagca ggtagcaaag tgacgccgag ggcctgagtg ctccagtagc    60
caccgcatct ggagaaccag cggttaccat ggagggatc agtatataca cttcagataa   120
ctacaccgag gaaatgggct caggggacta tgactccatg aaggaaccct gtttccgtga   180 agaaatgct aatttcaata aaatcttcct gcccaccatc tactccatca tcttcttaac   240
tggcattgtg ggcaatggat tggtcatcct ggtcatgggt taccagaaga aactgagaag   300
catgacggac aagtacaggc tgcacctgtc agtggccgac tcctctttg tcatcacgct   360 tcccttctgg gcagttgatg ccgtggcaaa ctggtacttt gggaacttcc tatgcaaggc   420
agtccatgtc atctacacag tcaacctcta cagcagtgtc ctcatcctgg ccttcatcag   480
tctggaccgc tacctggcca tcgtccacgc caccaacagt cagaggccaa ggaagctgtt   540
ggctgaaaag gtggtctatg ttggcgtctg gatccctgcc ctcctgctga ctattcccga   600
```

-continued

```
cttcatcttt gccaacgtca gtgaggcaga tgacagatat atctgtgacc gcttctaccc    660
caatgacttg tgggtggttg tgttccagtt tcagcacatc atggttggcc ttatcctgcc    720
tggtattgtc atcctgtcct gctattgcat tatcatctcc aagctgtcac actccaaggg    780
ccaccagaag cgcaaggccc tcaagaccac agtcatcctc atcctggctt tcttcgcctg    840
ttggctgcct tactacattg ggatcagcat cgactccttc atcctcctgg aaatcatcaa    900
gcaagggtgt gagtttgaga acactgtgca caagtggatt tccatcaccg aggccctagc    960
tttcttccac tgttgtctga accccatcct ctatgctttc cttggagcca aatttaaaac   1020
ctctgcccag cacgcactca cctctgtgag cagagggtcc agcctcaaga tcctctccaa   1080
aggaaagcga ggtggacatt catctgtttc cactgagtct gagtcttcaa gttttcactc   1140
cagctaacac agatgtaaaa gacttttttt tatacgataa ataactttt tttaagttac   1200
acattttca gatataaaag actgaccaat attgtacagt ttttattgct tgttggattt   1260
ttgtcttgtg tttctttagt ttttgtgaag tttaattgac ttatttatat aaattttttt   1320
tgtttcatat tgatgtgtgt ctaggcagga cctgtggcca agttcttagt tgctgtatgt   1380
ctcgtggtag gactgtagaa aagggaactg aacattccag agcgtgtagt gaatcacgta   1440
aagctagaaa tgatccccag ctgtttatgc atagataatc tctccattcc cgtgaacgt    1500
ttttcctgtt cttaagacgt gattttgctg tagaagatgg cacttataac caaagcccaa   1560
agtggtatag aaatgctggt ttttcagttt tcaggagtgg gttgatttca gcacctacag   1620
tgtacagtct tgtattaagt tgttaataaa agtacatgtt aaacttactt agtgttatg    1679
```

<210> SEQ ID NO 15
<211> LENGTH: 2181
<212> TYPE: DNA
<213> ORGANISM: Homo sapiens

<400> SEQUENCE: 15

```
atggagggag agaggaagaa caacaacaaa cggtggtatt tcactcgaga acagctggaa     60
aatagcccat cccgtcgttt tggcgtggac ccagataaag aactttctta tcgccagcag    120
gcggccaatc tgcttcagga catggggcag cgtcttaacg tctcacaatt gactatcaac    180
actgctatag tatacatgca tcgattctac atgattcagt ccttcacaca gttccctgga    240
aattctgtgg ctccagcagc cttgtttcta gcagctaaag tggaggagca gcccaaaaaa    300
ttggaacatg tcatcaaggt agcacatact tgtctccatc ctcaggaatc ccttcctgat    360
actagaagtg aggcttattt gcaacaagtt caagatctgg tcattttaga aagcataatt    420
ttgcagactt taggctttga actaacaatt gatcacccac atactcatgt agtaaagtgc    480
actcaacttg ttcgagcaag caaggactta gcacagactt cttacttcat ggcaaccaac    540
agcctgcatt tgaccacatt tagcctgcag tacacacctc tgtggtggc ctgtgtctgc    600
attcacctgg cttgcaagtg gtccaattgg gagatcccag tctcaactga cgggaagcac    660
tggtgggagt atgttgacgc cactgtgacc ttggaacttt tagatgaact gacacatgag    720
tttctacaga ttttggagaa aactcccaac aggctcaaac gcatttggaa ttggagggca    780
tgcgaggctg ccaagaaaac aaaagcagat gaccgaggaa cagatgaaaa gacttcagag    840
cagacaatcc tcaatatgat ttcccagagc tcttcagaca caaccattgc aggtttaatg    900
agcatgtcaa cttctaccac aagtgcagtg ccttccctgc cagtctccga agagtcatcc    960
agcaacttaa ccagtgtgga gatgttgccg ggcaagcgtt ggctgtcctc ccaaccttct   1020
```

-continued

```
ttcaaactag aacctactca gggtcatcgg actagtgaga atttagcact tacaggagtt    1080
gatcattcct taccacagga tggttcaaat gcatttattt cccagaagca gaatagtaag    1140
agtgtgccat cagctaaagt gtcactgaaa gaataccgcg cgaagcatgc agaagaattg    1200
gctgcccaga agaggcaact ggagaacatg gaagccaatg tgaagtcaca atatgcatat    1260
gctgcccaga atctcctttc tcatcatgat agccattctt cagtcattct aaaaatgccc    1320
atagagggtt cagaaaaccc cgagcggcct tttctggaaa aggctgacaa acagctctc    1380 aaaatgagaa tcccagtggc aggtggagat aaagctgcgt cttcaaaacc agaggagata    1440
aaaatgcgca taaagtcca tgctgcagct gataagcaca attctgtaga ggacagtgtt    1500
acaaagagcc gagagcacaa agaaaagcac aagactcacc catctaatca tcatcatcat    1560
cataatcacc actcacacaa gcactctcat tcccaacttc cagttggtac tgggaacaaa    1620
cgtcctggtg atccaaaaca tagtagccag acaagcaact tagcacataa aacctatagc    1680
ttgtctagtt ctttttcctc ttccagttct actcgtaaaa ggggaccctc tgaagagact    1740 ggagggctg tgtttgatca tccagccaag attgccaaga gtactaaatc ctcttcccta    1800
aatttctcct tcccttcact tcctacaatg ggtcagatgc ctgggcatag ctcagacaca    1860
agtggccttt cctttcaca gcccagctgt aaaactcgtg tccctcattc gaaactggat    1920
aaagggccca ctggggccaa tggtcacaac acgacccaga caatagacta tcaagacact    1980
gtgaatatgc ttcactccct gctcagtgcc caggtgttc agcccactca gcctactgca    2040
tttgaatttg ttcgtcctta tagtgactat ctgaatcctc ggtctggtgg aatctcctcg    2100
agatctggca atacagacaa accccggcca ccacctctgc catcagaacc tcctccacca    2160
cttccacccc ttcctaagta a                                            2181
```

<210> SEQ ID NO 16
<211> LENGTH: 1643
<212> TYPE: DNA
<213> ORGANISM: Homo sapiens
<220> FEATURE:
<221> NAME/KEY: CDS
<222> LOCATION: (25)..(915)

<400> SEQUENCE: 16

```
aacatctggg gacagcggga aaac atg agt gac tcc aag gaa cca agg gtg         51
                              Met Ser Asp Ser Lys Glu Pro Arg Val
                                1               5 cag cag ctg ggc ctc ctg ggg tgt ctt ggc cat ggc gcc ctg gtg ctg        99
Gln Gln Leu Gly Leu Leu Gly Cys Leu Gly His Gly Ala Leu Val Leu
 10              15                  20                  25 caa ctc ctc tcc ttc atg ctc ttg gct ggg gtc ctg gtg gcc atc ctt       147
Gln Leu Leu Ser Phe Met Leu Leu Ala Gly Val Leu Val Ala Ile Leu
                 30                  35                  40 gtc caa gtg tcc aag gtc ccc agc tcc cta agt cag gaa caa tcc gag       195
Val Gln Val Ser Lys Val Pro Ser Ser Leu Ser Gln Glu Gln Ser Glu
             45                  50                  55 caa gac gca atc tac cag aac ctg acc cag ctt aaa gct gca gtg ggt       243
Gln Asp Ala Ile Tyr Gln Asn Leu Thr Gln Leu Lys Ala Ala Val Gly
         60                  65                  70 gag ctc tca gag aaa tcc aag ctg cag gag atc tac cag gag ctg acc       291
Glu Leu Ser Glu Lys Ser Lys Leu Gln Glu Ile Tyr Gln Glu Leu Thr
 75                  80                  85 cag ctg aag gct gca gtg ggt gag ttg cca gag aaa tcc aag ctg cag       339
Gln Leu Lys Ala Ala Val Gly Glu Leu Pro Glu Lys Ser Lys Leu Gln
 90                  95                 100                 105
```

| | | |
|---|---|---|
| gag atc tac cag gag ctg acc cgg ctg aag gct gca gtg ggt gag ttg<br>Glu Ile Tyr Gln Glu Leu Thr Arg Leu Lys Ala Ala Val Gly Glu Leu<br>110                             115                    120 | 387 | |
| cca gag aaa tcc aag ctg cag gag atc tac cag gag ctg acc cgg ctg<br>Pro Glu Lys Ser Lys Leu Gln Glu Ile Tyr Gln Glu Leu Thr Arg Leu<br>125                           130                    135 | 435 | |
| aag gct gca gtg ggt gag ttg cca gag aaa tcc aag ctg cag gag atc<br>Lys Ala Ala Val Gly Glu Leu Pro Glu Lys Ser Lys Leu Gln Glu Ile<br>140                          145                    150 | 483 | |
| tac cag gag ctg acc cgg ctg aag gct gca gtg ggt gag ttg cca gag<br>Tyr Gln Glu Leu Thr Arg Leu Lys Ala Ala Val Gly Glu Leu Pro Glu<br>155                       160                    165 | 531 | |
| aaa tcc aag ctg cag gag atc tac cag gag ctg acg gag ctg aag gct<br>Lys Ser Lys Leu Gln Glu Ile Tyr Gln Glu Leu Thr Glu Leu Lys Ala<br>170                      175                    180                    185 | 579 | |
| gca gtg ggt gag ttg cca gag aaa tcc aag ctg cag gag atc tac cag<br>Ala Val Gly Glu Leu Pro Glu Lys Ser Lys Leu Gln Glu Ile Tyr Gln<br>                    190                    195                    200 | 627 | |
| gag ctg acc cag ctg aag gct gca gtg ggt gag ttg cca gac cag tcc<br>Glu Leu Thr Gln Leu Lys Ala Ala Val Gly Glu Leu Pro Asp Gln Ser<br>205                           210                    215 | 675 | |
| aag cag cag caa atc tat caa gaa ctg acc gat ttg aag act gca ttt<br>Lys Gln Gln Gln Ile Tyr Gln Glu Leu Thr Asp Leu Lys Thr Ala Phe<br>220                           225                    230 | 723 | |
| gaa cgc ctg tgc cgc cac tgt ccc aag gac tgg aca ttc ttc caa gga<br>Glu Arg Leu Cys Arg His Cys Pro Lys Asp Trp Thr Phe Phe Gln Gly<br>235                         240                    245 | 771 | |
| aac tgt tac ttc atg tct aac tcc cag cgg aac tgg cac gac tcc gtc<br>Asn Cys Tyr Phe Met Ser Asn Ser Gln Arg Asn Trp His Asp Ser Val<br>250                    255                   260                    265 | 819 | |
| acc gcc tgc cag gaa gtg agg gcc cag ctc gtc gta atc aaa act gct<br>Thr Ala Cys Gln Glu Val Arg Ala Gln Leu Val Val Ile Lys Thr Ala<br>                    270                    275                    280 | 867 | |
| gag gag cag ctt cca gcg gta ctg gaa cag tgg aga acc caa caa tag<br>Glu Glu Gln Leu Pro Ala Val Leu Glu Gln Trp Arg Thr Gln Gln<br>285                           290                    295 | 915 | |
| cgggaatgaa gactgtgcgg aatttagtgg cagtggctgg aacgacaatc gatgtgacgt | 975 | |
| tgacaattac tggatctgca aaaagcccgc agcctgcttc agagacgaat agttgtttcc | 1035 | |
| ctgctagcct cagcctccat tgtggtatag cagaacttca cccacttgta agccagcgct | 1095 | |
| tcttctctcc atccttggac cttcacaaat gccctgagac ggttctctgt tcgattttc | 1155 | |
| atcccctatg aacctgggtc ttattctgtc cttctgatgc ctccaagttt ccctggtgta | 1215 | |
| gagcttgtgt tcttggccca tccttggagc tttataagtg acctgagtgg gatgcattta | 1275 | |
| gggggcgggc ttggtatgtt gtatgaatcc actctctgtt ccttttggag attagactat | 1335 | |
| ttggattcat gtgtagctgc cctgtcccct gggctttat ctcatccatg caaactacca | 1395 | |
| tctgctcaac ttccagctac accccgtgca ccctttgac tggggacttg ctggttgaag | 1455 | |
| gagctcatct tgcaggctgg aagcaccagg gaattaattc ccccagtcaa ccaatggcat | 1515 | |
| ccagagaggg catggaggct ccatacaacc tcttccaccc ccacatcttt ctttgtccta | 1575 | |
| tacatgtctt ccatttggct gtttctgagt tgtagccttt ataataaagt ggtaaatgtt | 1635 | |
| gtaactgc | 1643 | |

<210> SEQ ID NO 17
<211> LENGTH: 296
<212> TYPE: PRT
<213> ORGANISM: Homo sapiens

```
<400> SEQUENCE: 17

Met Ser Asp Ser Lys Glu Pro Arg Val Gln Gln Leu Gly Leu Leu Gly
 1               5                  10                  15

Cys Leu Gly His Gly Ala Leu Val Leu Gln Leu Leu Ser Phe Met Leu
            20                  25                  30

Leu Ala Gly Val Leu Val Ala Ile Leu Val Gln Val Ser Lys Val Pro
        35                  40                  45

Ser Ser Leu Ser Gln Gln Ser Gln Asp Ala Ile Tyr Gln Asn
    50                  55                  60

Leu Thr Gln Leu Lys Ala Ala Val Gly Glu Leu Ser Glu Lys Ser Lys
 65                 70                  75                  80

Leu Gln Glu Ile Tyr Gln Glu Leu Thr Gln Leu Lys Ala Ala Val Gly
                85                  90                  95

Glu Leu Pro Glu Lys Ser Lys Leu Gln Glu Ile Tyr Gln Glu Leu Thr
            100                 105                 110

Arg Leu Lys Ala Ala Val Gly Glu Leu Pro Glu Lys Ser Lys Leu Gln
        115                 120                 125

Glu Ile Tyr Gln Glu Leu Thr Arg Leu Lys Ala Ala Val Gly Glu Leu
130                 135                 140

Pro Glu Lys Ser Lys Leu Gln Glu Ile Tyr Gln Glu Leu Thr Arg Leu
145                 150                 155                 160

Lys Ala Ala Val Gly Glu Leu Pro Glu Lys Ser Lys Leu Gln Glu Ile
                165                 170                 175

Tyr Gln Glu Leu Thr Glu Leu Lys Ala Ala Val Gly Glu Leu Pro Glu
            180                 185                 190

Lys Ser Lys Leu Gln Glu Ile Tyr Gln Glu Leu Thr Gln Leu Lys Ala
        195                 200                 205

Ala Val Gly Glu Leu Pro Asp Gln Ser Lys Gln Gln Gln Ile Tyr Gln
    210                 215                 220

Glu Leu Thr Asp Leu Lys Thr Ala Phe Glu Arg Leu Cys Arg His Cys
225                 230                 235                 240

Pro Lys Asp Trp Thr Phe Phe Gln Gly Asn Cys Tyr Phe Met Ser Asn
                245                 250                 255

Ser Gln Arg Asn Trp His Asp Ser Val Thr Ala Cys Gln Glu Val Arg
            260                 265                 270

Ala Gln Leu Val Val Ile Lys Thr Ala Glu Glu Gln Leu Pro Ala Val
        275                 280                 285

Leu Glu Gln Trp Arg Thr Gln Gln
    290                 295
```